(12) United States Patent
Davies et al.

(10) Patent No.: US 7,794,948 B2
(45) Date of Patent: Sep. 14, 2010

(54) BIOMARKERS FOR ALZHEIMER'S DISEASE

(75) Inventors: Huw Alun Davies, Epson Downs (GB); James McGuire, Virum (DK); Anja Hviid Simonsen, Frederiksberg (DK); Kaj Blennow, Molndal (SE); Vladimir Podust, Fremont, CA (US)

(73) Assignee: Vermilllion, Inc., Fremont, CA (US)

( * ) Notice: Subject to any disclaimer, the term of this patent is extended or adjusted under 35 U.S.C. 154(b) by 398 days.

(21) Appl. No.: 10/982,545

(22) Filed: Nov. 6, 2004

(65) Prior Publication Data

US 2005/0244890 A1 Nov. 3, 2005

Related U.S. Application Data

(60) Provisional application No. 60/586,503, filed on Jul. 8, 2004, provisional application No. 60/572,617, filed on May 18, 2004, provisional application No. 60/558,896, filed on Apr. 2, 2004, provisional application No. 60/547,250, filed on Feb. 23, 2004, provisional application No. 60/546,423, filed on Feb. 19, 2004, provisional application No. 60/526,753, filed on Dec. 2, 2003, provisional application No. 60/518,360, filed on Nov. 7, 2003.

(51) Int. Cl.
*G01N 33/50* (2006.01)
(52) U.S. Cl. .......................................... 435/7.1; 702/19
(58) Field of Classification Search ........................ None
See application file for complete search history.

(56) References Cited

U.S. PATENT DOCUMENTS

2002/0138208 A1* 9/2002 Paulse et al. .................. 702/22

FOREIGN PATENT DOCUMENTS

| WO | WO 00/25138 A2 | 5/2000 |
|---|---|---|
| WO | WO 0025138 A2 * | 5/2000 |
| WO | WO 02/02824 A1 | 1/2002 |
| WO | WO 03/045991 A2 | 6/2003 |
| WO | WO 2004/019043 A2 | 3/2004 |

OTHER PUBLICATIONS

Martin. Molecular mechanisms of late life dementias. Experimental Gerontology 35(4):Jul. 1, 2000, pp. 439-443.*
Kasa et al. The cholinergic system in Alzheimer's disease. Progress in Neurobiology 52(6): Aug. 1997, pp. 511-535.*
Asgeirsson et al. Hereditary cystatin C amyloid angiopathy: monitoring the presence of the Leu-68→,Gln cystatin C variant in cerebrospinal fluids and monocyte cultures by MS. Biochem J. Feb 1, 1998;329 ( Pt 3):497-503.*
Wang et al. Microvascular degeneration in hereditary cystatin C amyloid angiopathy of the brain. APMIS Jan. 1997;105(1):41-7.*
Rachakonda et al. Biomarkers of neurodegenerative disorders: how good are they? Cell Res. Oct. 2004;14(5):349-360.*
Pleines et al. S-100 beta reflects the extent of injury and outcome, whereas neuronal specific enolase is a better indicator of neuroinflammation in patients with severe traumatic brain injury. J Neurotrauma. May 2001;18(5):491-8.*
Trof et al. Biomarkers of acute renal injury and renal failure. Shock. Sep. 2006;26(3):245-53.*
Blennow et al. Chromogranin A in cerebrospinal fluid: a biochemical marker for synaptic degeneration in Alzheimer's disease? Dementia, vol. 6, (1995), pp. 306-311.
Carrett et al. "A panel of cerebrospinal fluid potential biomarkers for the diagnosis of Alzheimer's disease" Proteomics vol. 3, (Aug. 2003), pp. 1486-1494.
Davidson et al. "Proteome analysis of cerebrospinal fluid proteins in Alzheimer patients" Clinical Nueroscience and Nueropathology (Apr. 2002), vol. 13, No. 5, pp. 611-615.
Elovaara "Proteins in serum and cerebrospinal fluid in demented patients with Down's syndrome" Acta Nuerological Scand., vol. 69, (1984) pp. 302-305.
Harigaya et al. "Alpha 1-antichymotrypsin level in cerebrospinal fluid is closely associated with late onset Alzheimer's disease" Internal Medicine, vol. 34, No. 6 (Jun. 1995), pp. 481-484.
Hoekman, et al. "The significance of beta-2 microglobulin in clinical medicine" Neth. J. Med. vol. 28, (1985) pp. 551-557.
Iqbal et al. "Mechanisms of nuerofibrillary degeneration and the formation of nuerofibrillary tangles" J. Neural Transm vol. 53, (1998) pp. 169-180.
Kodo et al. "Alzheimer disease: correlation of cerebro-spinal fluid and brain ubiquitin levels" Brain Research, vol. 639, (Mar. 1994), pp. 1-7.
Levy et al. " Codeposition of cystatin C with amyloid-β protein in the brain of Alzheimer disease patients", Journal of Neuropathology and Experimental Nuerology, vol. 60, No. 1 (Jan. 2001) pp. 94-104.
Matsubara et al. "α1-Antichymotrypsin as a possible biochemical marker for Alzheimer-type dementia" Annals of Neurology vol. 28, No. 4 (Oct. 1990) pp. 561-567.
Merched et al. "Apolipoprotein E, transthyretin and actin in the CSF of Alzheimer's patients: relation with the senile plaques and cytoskeleton biochemistry" FEBS Letters; vol. 425, No. 2, (1998) pp. 225-228.
Potter et al. " The inflammation-induced pathological chaperones ACT and apo-E are necessary catalysts of Alzheimer amyloid formation" Neurobology of Aging, vol. 22, (2001) pp. 923-930.

(Continued)

*Primary Examiner*—Daniel E Kolker
*Assistant Examiner*—Gregory S Emch
(74) *Attorney, Agent, or Firm*—Edwards Angell Palmer & Dodge LLP; Peter F. Corless; Jonathan M. Sparks

(57) ABSTRACT

The present invention provides protein-based biomarkers and biomarker combinations that are useful in qualifying Alzheimer's disease status in a patient. In particular, the biomarkers of this invention are useful to classify a subject sample as Alzheimer's or non-Alzheimer's dementia or normal. The biomarkers can be detected by SELDI mass spectrometry. In addition, the invention provides appropriate treatment interventions and methods for measuring response to treatment. Certain biomarkers of the invention may also be suitable for employment as radio-labeled ligands in non-invasive imaging techniques such as Positron Emission Tomography (PET).

21 Claims, 57 Drawing Sheets

OTHER PUBLICATIONS

Riisøen, "Reduced prealbumin (transthyretin) in CSF of severely demented patients with Alzheimer's disease" Acta Nuerolgoical Scand. vol. 78, (1988) pp. 455-459.

Serot et al. "Cerebrospinal fluid transthyretin: aging and late onset Alzheimer's disease", J Neurol Neurosurg Psychiatry; vol. 63 (Oct. 1997) pp. 506-508.

Skoog et al. "A population study on blood-brain barrier function in 85-year-olds" Neurology vol. 50, (1998) pp. 961-971.

Tsuzuki et al. "Transthyretin binds amyloid β peptides, Aβ1-42 and Aβ1-40 to form complex in the autopsied human kidney—possible role of transthyretin for Aβ sequestration" Nueroscience Letters, vol. 281. (2000) pp. 171-174.

Wang et al. "Alzheimer's disease: paired helical filament immunoreactivity in cerebrospinal fluid" Acta Neuropathol vol. 82, No. 1, (1991) pp. 6-12.

Lüthi, U., "Proteolytic Enzymes as Therapeutic Targets," ESBA tech, 2002, 5 pp.

Mares, J., et al., " Use of Cystatin C Determination in Clinical Diagnostics," Biomed. Papers, 2003, vol. 147., No. 2, pp. 177-180.

Popović, T. et al., "Different Forms of Human Cycstatin C." Biol. Chem., 1990, vol. 371, pp. 575-580.

Carrette, Odile et al.; "A new sensitive and highly specific test for the diagnosis of Alzheimer Disease using the ProteinChip® technology"; 2003, *FASEB Journal*, 1 page abstract.

Deng, Amy et al.; "Elevation of Cystatin C in Susceptible Neurons in Alzheimer's Disease"; 2001, *American Journal of Pathology*, vol. 159, No. 3, pp. 1061-1068.

Ghiso, Jorge et al.; "Amyloid fibrils in hereditary cerebral hemorrhage with amyloidosis of Icelandic type is a variant of gamma-trace basic protein (cystatin C)"; 1986, *Proceedings of the National Academy of Science*, vol. 83, pp. 2974-2978.

Tack, J. Leung et al.; "Modulation of Phagocytosis-Associated Respiratory Burst by Human Cystatin C: Role of the *N*-Terminal Tetrapeptide Lys-Pro-Pro-Arg" 1990, *Experimental Cell Research*, vol. 188, pp. 16-22.

\* cited by examiner

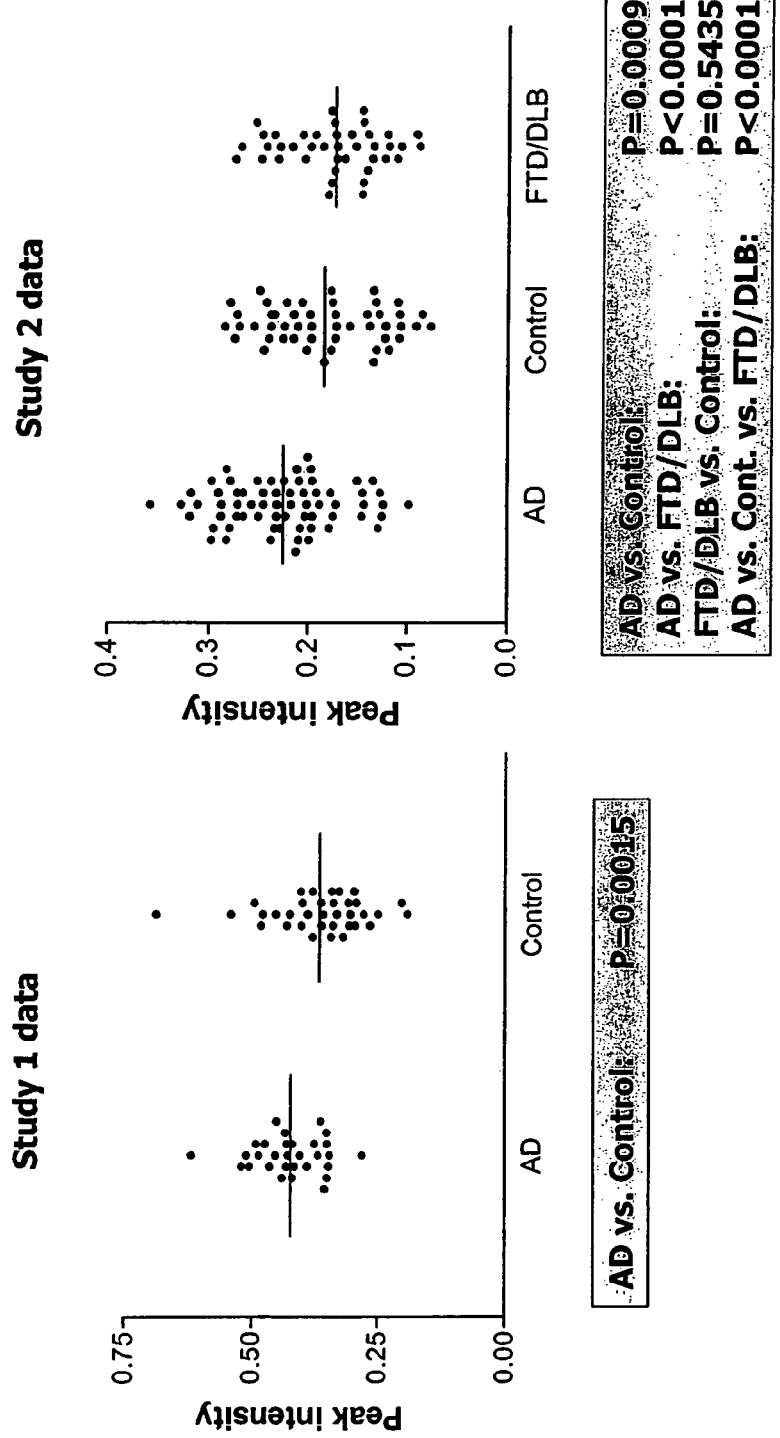

Hemopexin:

7B2 CT fragment:

Ubiquitin -3aa from CT:

Beta-2-microglobulin:

Transthyretin S-glutathyonylated and Transthyretin S-Cys /S-CysGly:

Cystatin C -8aa from NT:

Ubiquitin -4aa:

Secretoneurin:

Secretoneurin:

Transferrin:

Chromogranin B peptide 6.5 kDa:

A-beta 1-40:

Chromogranin B peptide 7.2 kDa:

Apo A-II dimmer:

C3a des-Arg:

Cys C:

Prostaglandin-D synthase:

Alpha-1-antichymotrypsin CT fragment:

Osteopontin CT fragment:

VGF (NCBI) peptide:

Thymosin beta-4 acetylated:

Albumin:

Osteopontin CT fragment phospho:

Ubiquitin:

5.0 kDa:

9.7, 9.9, 10.2 and 10.3 kDa:

EA-92 Chromogranin A peptide:

Pancreatic ribonuclease:

5.2 kDa:

3.8 kDa:

8.9kDa:

5.2 kDa:

14.5 kDa:

20.8 kDa:

6.6 kDa:

7.8 kDa:

92 kDa:

3.9 kDa:

89 kDa:

11.5 kDa:

4.4 kDa:

Marker validation

12583.8 Da marker

| Kruskal Wallis p value | Mann Whitney p value | | |
|---|---|---|---|
| A/C/N | A-C | A-N | C-N |
| 0.0001 | 0.0649 | <0.0001 | 0.0085 |

P = 0.0001

13391.9 Da marker

| Kruskal Wallis p value | Mann Whitney p value | | |
|---|---|---|---|
| A/C/N | A-C | A-N | C-N |
| 0.148 | 0.0527 | 0.8451 | 0.1896 |

P = 0.148

SEQUENCE LISTING

```
<160> NUMBER OF SEQ ID NOS: 16

<210> SEQ ID NO 1
<211> LENGTH: 76
<212> TYPE: PRT
<213> ORGANISM: Homo sapiens
<220> FEATURE:
<223> OTHER INFORMATION: biomarker peptide M8623.24, C4ades-Arg protein
      cleavage product of anaphylatoxin C4a from
      complement component C4 precursor

<400> SEQUENCE: 1

Asn Val Asn Phe Gln Lys Ala Ile Asn Glu Lys Leu Gly Gln Tyr Ala
 1               5                   10                  15

Ser Pro Thr Ala Lys Arg Cys Cys Gln Asp Gly Val Thr Arg Leu Pro
                20                  25                  30

Met Met Arg Ser Cys Glu Gln Arg Ala Ala Arg Val Gln Gln Pro Asp
            35                  40                  45

Cys Arg Glu Pro Phe Leu Ser Cys Cys Gln Phe Ala Glu Ser Leu Arg
        50                  55                  60

Lys Lys Ser Arg Asp Lys Gly Gln Ala Gly Leu Gln
    65                  70                  75

<210> SEQ ID NO 2
<211> LENGTH: 617
<212> TYPE: PRT
<213> ORGANISM: Homo sapiens
<220> FEATURE:
<223> OTHER INFORMATION: Secretogranin II (Chromogranin C, EM66,
      secretoneurin) precursor
<220> FEATURE:
<221> NAME/KEY: PEPTIDE
<222> LOCATION: (182)..(214)
<223> OTHER INFORMATION: biomarker peptide M3680.7

<400> SEQUENCE: 2

Met Ala Glu Ala Lys Thr His Trp Leu Gly Ala Ala Leu Ser Leu Ile
 1               5                   10                  15

Pro Leu Ile Phe Leu Ile Ser Gly Ala Glu Ala Ala Ser Phe Gln Arg
                20                  25                  30

Asn Gln Leu Leu Gln Lys Glu Pro Asp Leu Arg Leu Glu Asn Val Gln
            35                  40                  45

Lys Phe Pro Ser Pro Glu Met Ile Arg Ala Leu Glu Tyr Ile Glu Asn
        50                  55                  60
```

-continued

```
Leu Arg Gln Gln Ala His Lys Glu Ser Ser Pro Asp Tyr Asn Pro
 65                  70                  75                  80

Tyr Gln Gly Val Ser Val Pro Leu Gln Lys Glu Asn Gly Asp Glu
             85                   90                   95

Ser His Leu Pro Glu Arg Asp Ser Leu Ser Glu Asp Trp Met Arg
            100                  105                  110

Ile Ile Leu Glu Ala Leu Arg Gln Ala Glu Asn Glu Pro Gln Ser Ala
            115                  120                  125

Pro Lys Glu Asn Lys Pro Tyr Ala Leu Asn Ser Glu Lys Asn Phe Pro
            130                  135                  140

Met Asp Met Ser Asp Tyr Glu Thr Gln Gln Trp Pro Glu Arg Lys
145                  150                  155                  160

Leu Lys His Met Gln Phe Pro Pro Met Tyr Glu Glu Asn Ser Arg Asp
                165                  170                  175

Asn Pro Phe Lys Arg Thr Asn Glu Ile Val Glu Glu Gln Tyr Thr Pro
            180                  185                  190

Gln Ser Leu Ala Thr Leu Glu Ser Val Phe Gln Glu Leu Gly Lys Leu
            195                  200                  205

Thr Gly Pro Asn Asn Gln Lys Arg Glu Arg Met Asp Glu Glu Gln Lys
210                  215                  220

Leu Tyr Thr Asp Asp Glu Asp Ile Tyr Lys Ala Asn Asn Ile Ala
225                  230                  235                  240

Tyr Glu Asp Val Val Gly Gly Glu Asp Trp Asn Pro Val Glu Glu Lys
                245                  250                  255

Ile Glu Ser Gln Thr Gln Glu Glu Val Arg Asp Ser Lys Glu Asn Ile
            260                  265                  270

Gly Lys Asn Glu Gln Ile Asn Asp Glu Met Lys Arg Ser Gly Gln Leu
            275                  280                  285

Gly Ile Gln Glu Glu Asp Leu Arg Lys Glu Ser Lys Asp Gln Leu Ser
290                  295                  300

Asp Asp Val Ser Lys Val Ile Ala Tyr Leu Lys Arg Leu Val Asn Ala
305                  310                  315                  320

Ala Gly Ser Gly Arg Leu Gln Asn Gly Gln Asn Gly Glu Arg Ala Thr
                325                  330                  335

Arg Leu Phe Glu Lys Pro Leu Asp Ser Gln Ser Ile Tyr Gln Leu Ile
            340                  345                  350

Glu Ile Ser Arg Asn Leu Gln Ile Pro Pro Glu Asp Leu Ile Glu Met
            355                  360                  365

Leu Lys Thr Gly Glu Lys Pro Asn Gly Ser Val Glu Pro Glu Arg Glu
            370                  375                  380

Leu Asp Leu Pro Val Asp Leu Asp Asp Ile Ser Glu Ala Asp Leu Asp
385                  390                  395                  400

His Pro Asp Leu Phe Gln Asn Arg Met Leu Ser Lys Ser Gly Tyr Pro
                405                  410                  415

Lys Thr Pro Gly Arg Ala Gly Thr Glu Ala Leu Pro Asp Gly Leu Ser
            420                  425                  430

Val Glu Asp Ile Leu Asn Leu Leu Gly Met Glu Ser Ala Ala Asn Gln
            435                  440                  445

Lys Thr Ser Tyr Phe Pro Asn Pro Tyr Asn Gln Glu Lys Val Leu Pro
            450                  455                  460

Arg Leu Pro Tyr Gly Ala Gly Arg Ser Arg Ser Asn Gln Leu Pro Lys
465                  470                  475                  480
```

-continued

```
Ala Ala Trp Ile Pro His Val Glu Asn Arg Gln Met Ala Tyr Glu Asn
            485                 490                 495

Leu Asn Asp Lys Asp Gln Glu Leu Gly Glu Tyr Leu Ala Arg Met Leu
            500                 505                 510

Val Lys Tyr Pro Glu Ile Ile Asn Ser Asn Gln Val Lys Arg Val Pro
            515                 520                 525

Gly Gln Gly Ser Ser Glu Asp Asp Leu Gln Glu Glu Gln Ile Glu
        530                 535                 540

Gln Ala Ile Lys Glu His Leu Asn Gln Gly Ser Ser Gln Glu Thr Asp
545                 550                 555                 560

Lys Leu Ala Pro Val Ser Lys Arg Phe Pro Val Gly Pro Pro Lys Asn
                565                 570                 575

Asp Asp Thr Pro Asn Arg Gln Tyr Trp Asp Glu Asp Leu Leu Met Lys
            580                 585                 590

Val Leu Glu Tyr Leu Asn Gln Glu Lys Ala Glu Lys Gly Arg Glu His
            595                 600                 605

Ile Ala Lys Arg Ala Met Glu Asn Met
            610                 615

<210> SEQ ID NO 3
<211> LENGTH: 266
<212> TYPE: PRT
<213> ORGANISM: Homo sapiens
<220> FEATURE:
<223> OTHER INFORMATION: Integral Membrane Protein 2B (MMP2B,
      transmembrane protein BRI, E3-16)
<220> FEATURE:
<221> NAME/KEY: PEPTIDE
<222> LOCATION: (244)..(266)
<223> OTHER INFORMATION: ABri/ADan amyloid peptide
<220> FEATURE:
<221> NAME/KEY: PEPTIDE
<222> LOCATION: (246)..(266)
<223> OTHER INFORMATION: biomarker peptide M2431.2, truncated ABri/ADan
      amyloid peptide

<400> SEQUENCE: 3

Met Val Lys Val Thr Phe Asn Ser Ala Leu Ala Gln Lys Glu Ala Lys
1               5                   10                  15

Lys Asp Glu Pro Lys Ser Gly Glu Glu Ala Leu Ile Ile Pro Pro Asp
            20                  25                  30

Ala Val Ala Val Asp Cys Lys Asp Pro Asp Asp Val Val Pro Val Gly
            35                  40                  45

Gln Arg Arg Ala Trp Cys Trp Cys Met Cys Phe Gly Leu Ala Phe Met
        50                  55                  60

Leu Ala Gly Val Ile Leu Gly Gly Ala Tyr Leu Tyr Lys Tyr Phe Ala
65                  70                  75                  80

Leu Gln Pro Asp Asp Val Tyr Tyr Cys Gly Ile Lys Tyr Ile Lys Asp
                85                  90                  95

Asp Val Ile Leu Asn Glu Pro Ser Ala Asp Ala Pro Ala Ala Leu Tyr
            100                 105                 110

Gln Thr Ile Glu Glu Asn Ile Lys Ile Phe Glu Glu Glu Val Glu
            115                 120                 125

Phe Ile Ser Val Pro Val Pro Glu Phe Ala Asp Ser Asp Pro Ala Asn
        130                 135                 140

Ile Val His Asp Phe Asn Lys Lys Leu Thr Ala Tyr Leu Asp Leu Asn
145                 150                 155                 160

Leu Asp Lys Cys Tyr Val Ile Pro Leu Asn Thr Ser Ile Val Met Pro
                165                 170                 175
```

-continued

```
Pro Arg Asn Leu Leu Glu Leu Leu Ile Asn Ile Lys Ala Gly Thr Tyr
            180                 185                 190

Leu Pro Gln Ser Tyr Leu Ile His Glu His Met Val Ile Thr Asp Arg
        195                 200                 205

Ile Glu Asn Ile Asp His Leu Gly Phe Phe Ile Tyr Arg Leu Cys His
    210                 215                 220

Asp Lys Glu Thr Tyr Lys Leu Gln Arg Arg Glu Thr Ile Lys Gly Ile
225                 230                 235                 240

Gln Lys Arg Glu Ala Ser Asn Cys Phe Ala Ile Arg His Phe Glu Asn
                245                 250                 255

Lys Phe Ala Val Glu Thr Leu Ile Cys Ser
                260                 265

<210> SEQ ID NO 4
<211> LENGTH: 146
<212> TYPE: PRT
<213> ORGANISM: Homo sapiens
<220> FEATURE:
<223> OTHER INFORMATION: Cystatin C precursor
<220> FEATURE:
<221> NAME/KEY: SIGNAL
<222> LOCATION: (1)..(26)
<223> OTHER INFORMATION: signal peptide
<220> FEATURE:
<221> NAME/KEY: PEPTIDE
<222> LOCATION: (27)..(146)
<223> OTHER INFORMATION: biomarker peptide M13391, full-length Cystatin
      C mature peptide
<220> FEATURE:
<221> NAME/KEY: PEPTIDE
<222> LOCATION: (35)..(146)
<223> OTHER INFORMATION: biomarker peptide M12583.4, truncated Cystatin
      C

<400> SEQUENCE: 4

Met Ala Gly Pro Leu Arg Ala Pro Leu Leu Leu Leu Ala Ile Leu Ala
1               5                   10                  15

Val Ala Leu Ala Val Ser Pro Ala Ala Gly Ser Ser Pro Gly Lys Pro
            20                  25                  30

Pro Arg Leu Val Gly Gly Pro Met Asp Ala Ser Val Glu Glu Glu Gly
        35                  40                  45

Val Arg Arg Ala Leu Asp Phe Ala Val Gly Glu Tyr Asn Lys Ala Ser
    50                  55                  60

Asn Asp Met Tyr His Ser Arg Ala Leu Gln Val Val Arg Ala Arg Lys
65                  70                  75                  80

Gln Ile Val Ala Gly Val Asn Tyr Phe Leu Asp Val Glu Leu Gly Arg
                85                  90                  95

Thr Thr Cys Thr Lys Thr Gln Pro Asn Leu Asp Asn Cys Pro Phe His
            100                 105                 110

Asp Gln Pro His Leu Lys Arg Lys Ala Phe Cys Ser Phe Gln Ile Tyr
        115                 120                 125

Ala Val Pro Trp Gln Gly Thr Met Thr Leu Ser Lys Ser Thr Cys Gln
    130                 135                 140

Asp Ala
145

<210> SEQ ID NO 5
<211> LENGTH: 616
<212> TYPE: PRT
<213> ORGANISM: Homo sapiens
<220> FEATURE:
```

-continued

```
<223> OTHER INFORMATION: nerve growth factor inducible Neurosecretory
      protein vaccinia virus growth factor (VGF)
      precursor
<220> FEATURE:
<221> NAME/KEY: SIGNAL
<222> LOCATION: (1)..(22)
<223> OTHER INFORMATION: signal peptide
<220> FEATURE:
<221> NAME/KEY: PEPTIDE
<222> LOCATION: (23)..(616)
<223> OTHER INFORMATION: biomarker peptide M3951.6, nerve growth factor
      inducible Neurosecretory protein vaccinia virus
      growth factor (VGF) mature peptide
<220> FEATURE:
<221> NAME/KEY: PEPTIDE
<222> LOCATION: (26)..(62)
<223> OTHER INFORMATION: biomarker peptide M3687.7, N-terminal fragment
      of nerve growth factor indicible Neurosecretory protein vaccinia
      virus growth factor (VGF)

<400> SEQUENCE: 5

Met Lys Ala Leu Arg Leu Ser Ala Ser Ala Leu Phe Cys Leu Leu Leu
  1               5                  10                  15

Ile Asn Gly Leu Gly Ala Ala Pro Pro Gly Arg Pro Glu Ala Gln Pro
             20                  25                  30

Pro Pro Leu Ser Ser Glu His Lys Glu Pro Val Ala Gly Asp Ala Val
         35                  40                  45

Pro Gly Pro Lys Asp Gly Ser Ala Pro Glu Val Arg Gly Ala Arg Asn
     50                  55                  60

Ser Glu Pro Gln Asp Glu Gly Glu Leu Phe Gln Gly Val Asp Pro Arg
 65                  70                  75                  80

Ala Leu Ala Ala Val Leu Leu Gln Ala Leu Asp Arg Pro Ala Ser Pro
                 85                  90                  95

Pro Ala Pro Ser Gly Ser Gln Gln Gly Pro Glu Glu Glu Ala Ala Glu
            100                 105                 110

Ala Leu Leu Thr Glu Thr Val Arg Ser Gln Thr His Ser Leu Pro Ala
        115                 120                 125

Ala Gly Glu Pro Glu Pro Ala Ala Pro Pro Arg Pro Gln Thr Pro Glu
    130                 135                 140

Asn Gly Pro Glu Ala Ser Asp Pro Ser Glu Glu Leu Glu Ala Leu Ala
145                 150                 155                 160

Ser Leu Leu Gln Glu Leu Arg Asp Phe Ser Pro Ser Ser Ala Lys Arg
                165                 170                 175

Gln Gln Glu Thr Ala Ala Ala Glu Thr Glu Thr Arg Thr His Thr Leu
            180                 185                 190

Thr Arg Val Asn Leu Glu Ser Pro Gly Pro Glu Arg Val Trp Arg Ala
        195                 200                 205

Ser Trp Gly Glu Phe Gln Ala Arg Val Pro Glu Arg Ala Pro Leu Pro
    210                 215                 220

Pro Pro Ala Pro Ser Gln Phe Gln Ala Arg Met Pro Asp Ser Gly Pro
225                 230                 235                 240

Leu Pro Glu Thr His Lys Phe Gly Glu Gly Val Ser Ser Pro Lys Thr
                245                 250                 255

His Leu Gly Glu Ala Leu Ala Pro Leu Ser Lys Ala Tyr Gln Gly Val
            260                 265                 270

Ala Ala Pro Phe Pro Lys Ala Arg Arg Ala Glu Ser Ala Leu Leu Gly
        275                 280                 285

Gly Ser Glu Ala Gly Glu Arg Leu Leu Gln Gln Gly Leu Ala Gln Val
    290                 295                 300
```

-continued

```
Glu Ala Gly Arg Arg Gln Ala Glu Ala Thr Arg Gln Ala Ala Gln
305                 310                 315                 320

Glu Glu Arg Leu Ala Asp Leu Ala Ser Asp Leu Leu Gln Tyr Leu
            325                 330                 335

Leu Gln Gly Gly Ala Arg Gln Arg Gly Leu Gly Gly Arg Gly Leu Gln
        340                 345                 350

Glu Ala Ala Glu Glu Arg Glu Ser Ala Arg Glu Glu Glu Ala Glu
            355                 360                 365

Gln Glu Arg Arg Gly Gly Glu Arg Val Gly Glu Glu Asp Glu Glu
        370                 375                 380

Ala Ala Glu Ala Ala Glu Glu Ala Asp Glu Ala Glu Arg Ala Arg
385                 390                 395                 400

Gln Asn Ala Leu Leu Phe Ala Glu Glu Glu Asp Gly Glu Ala Gly Ala
            405                 410                 415

Glu Asp Lys Arg Ser Gln Glu Glu Thr Pro Gly His Arg Arg Lys Glu
        420                 425                 430

Ala Glu Gly Thr Glu Glu Gly Gly Glu Glu Glu Asp Asp Glu Glu Met
            435                 440                 445

Asp Pro Gln Thr Ile Asp Ser Leu Ile Glu Leu Ser Thr Lys Leu His
450                 455                 460

Leu Pro Ala Asp Asp Val Val Ser Ile Ile Glu Glu Val Glu Lys
465                 470                 475                 480

Arg Asn Arg Lys Lys Lys Ala Pro Pro Glu Pro Val Pro Pro Pro Arg
            485                 490                 495

Ala Ala Pro Ala Pro Thr His Val Arg Ser Pro Gln Pro Pro Pro Pro
        500                 505                 510

Pro Pro Ser Ala Arg Asp Glu Leu Pro Asp Trp Asn Glu Val Leu Pro
    515                 520                 525

Pro Trp Asp Arg Glu Glu Asp Glu Val Tyr Pro Pro Gly Pro Tyr His
530                 535                 540

Pro Phe Pro Asn Tyr Ile Arg Pro Arg Thr Leu Gln Pro Pro Ser Ala
545                 550                 555                 560

Leu Arg Arg Arg His Tyr His His Ala Leu Pro Pro Ser Arg His Tyr
                565                 570                 575

Pro Gly Arg Glu Ala Gln Ala Arg Ala His Ala Gln Gln Glu Glu Ala Glu
        580                 585                 590

Ala Glu Glu Arg Arg Leu Gln Glu Gln Glu Glu Leu Glu Asn Tyr Ile
            595                 600                 605

Glu His Val Leu Leu Arg Arg Pro
        610                 615

<210> SEQ ID NO 6
<211> LENGTH: 1663
<212> TYPE: PRT
<213> ORGANISM: Homo sapiens
<220> FEATURE:
<223> OTHER INFORMATION: complement component C3 precursor
<220> FEATURE:
<221> NAME/KEY: SIGNAL
<222> LOCATION: (1)..(23)
<223> OTHER INFORMATION: signal peptide
<220> FEATURE:
<221> NAME/KEY: CHAIN
<222> LOCATION: (23)..(667)
<223> OTHER INFORMATION: complement component C3 beta-chain
<220> FEATURE:
<221> NAME/KEY: CHAIN
<222> LOCATION: (672)..(1663)
<223> OTHER INFORMATION: complement component C3 alpha-chain
```

```
<220> FEATURE:
<221> NAME/KEY: PEPTIDE
<222> LOCATION: (672)..(748)
<223> OTHER INFORMATION: C3a anaphylatoxin peptide
<220> FEATURE:
<221> NAME/KEY: PEPTIDE
<222> LOCATION: (672)..(747)
<223> OTHER INFORMATION: biomarker peptide M8933.2, C3a anaphylatoxin
      desArg peptide

<400> SEQUENCE: 6
```

Met Gly Pro Thr Ser Gly Pro Ser Leu Leu Leu Leu Leu Thr His
  1               5                  10                  15

Leu Pro Leu Ala Leu Gly Ser Pro Met Tyr Ser Ile Ile Thr Pro Asn
             20                  25                  30

Ile Leu Arg Leu Glu Ser Glu Glu Thr Met Val Leu Glu Ala His Asp
         35                  40                  45

Ala Gln Gly Asp Val Pro Val Thr Val Thr Val His Asp Phe Pro Gly
     50                  55                  60

Lys Lys Leu Val Leu Ser Ser Glu Lys Thr Val Leu Thr Pro Ala Thr
 65                  70                  75                  80

Asn His Met Gly Asn Val Thr Phe Thr Ile Pro Ala Asn Arg Glu Phe
                 85                  90                  95

Lys Ser Glu Lys Gly Arg Asn Lys Phe Val Thr Val Gln Ala Thr Phe
            100                 105                 110

Gly Thr Gln Val Val Glu Lys Val Val Leu Val Ser Leu Gln Ser Gly
        115                 120                 125

Tyr Leu Phe Ile Gln Thr Asp Lys Thr Ile Tyr Thr Pro Gly Ser Thr
130                 135                 140

Val Leu Tyr Arg Ile Phe Thr Val Asn His Lys Leu Leu Pro Val Gly
145                 150                 155                 160

Arg Thr Val Met Val Asn Ile Glu Asn Pro Glu Gly Ile Pro Val Lys
                165                 170                 175

Gln Asp Ser Leu Ser Ser Gln Asn Gln Leu Gly Val Leu Pro Leu Ser
            180                 185                 190

Trp Asp Ile Pro Glu Leu Val Asn Met Gly Gln Trp Lys Ile Arg Ala
        195                 200                 205

Tyr Tyr Glu Asn Ser Pro Gln Gln Val Phe Ser Thr Glu Phe Glu Val
210                 215                 220

Lys Glu Tyr Val Leu Pro Ser Phe Glu Val Ile Val Glu Pro Thr Glu
225                 230                 235                 240

Lys Phe Tyr Tyr Ile Tyr Asn Glu Lys Gly Leu Glu Val Thr Ile Thr
                245                 250                 255

Ala Arg Phe Leu Tyr Gly Lys Lys Val Glu Gly Thr Ala Phe Val Ile
            260                 265                 270

Phe Gly Ile Gln Asp Gly Glu Gln Arg Ile Ser Leu Pro Glu Ser Leu
        275                 280                 285

Lys Arg Ile Pro Ile Glu Asp Gly Ser Gly Glu Val Val Leu Ser Arg
290                 295                 300

Lys Val Leu Leu Asp Gly Val Gln Asn Leu Arg Ala Glu Asp Leu Val
305                 310                 315                 320

Gly Lys Ser Leu Tyr Val Ser Ala Thr Val Ile Leu His Ser Gly Ser
                325                 330                 335

Asp Met Val Gln Ala Glu Arg Ser Gly Ile Pro Ile Val Thr Ser Pro
            340                 345                 350

Tyr Gln Ile His Phe Thr Lys Thr Pro Lys Tyr Phe Lys Pro Gly Met

-continued

```
            355                 360                 365
Pro Phe Asp Leu Met Val Phe Val Thr Asn Pro Asp Gly Ser Pro Ala
370                 375                 380

Tyr Arg Val Pro Val Ala Val Gln Gly Glu Asp Thr Val Gln Ser Leu
385                 390                 395                 400

Thr Gln Gly Asp Gly Val Ala Lys Leu Ser Ile Asn Thr His Pro Ser
                405                 410                 415

Gln Lys Pro Leu Ser Ile Thr Val Arg Thr Lys Gln Glu Leu Ser
                420                 425                 430

Glu Ala Glu Gln Ala Thr Arg Thr Met Gln Ala Leu Pro Tyr Ser Thr
            435                 440                 445

Val Gly Asn Ser Asn Asn Tyr Leu His Leu Ser Val Leu Arg Thr Glu
        450                 455                 460

Leu Arg Pro Gly Glu Thr Leu Asn Val Asn Phe Leu Leu Arg Met Asp
465                 470                 475                 480

Arg Ala His Glu Ala Lys Ile Arg Tyr Tyr Thr Tyr Leu Ile Met Asn
                485                 490                 495

Lys Gly Arg Leu Leu Lys Ala Gly Arg Gln Val Arg Glu Pro Gly Gln
                500                 505                 510

Asp Leu Val Val Leu Pro Leu Ser Ile Thr Thr Asp Phe Ile Pro Ser
            515                 520                 525

Phe Arg Leu Val Ala Tyr Tyr Thr Leu Ile Gly Ala Ser Gly Gln Arg
        530                 535                 540

Glu Val Val Ala Asp Ser Val Trp Val Asp Val Lys Asp Ser Cys Val
545                 550                 555                 560

Gly Ser Leu Val Val Lys Ser Gly Gln Ser Glu Asp Arg Gln Pro Val
                565                 570                 575

Pro Gly Gln Gln Met Thr Leu Lys Ile Glu Gly Asp His Gly Ala Arg
            580                 585                 590

Val Val Leu Val Ala Val Asp Lys Gly Val Phe Val Leu Asn Lys Lys
        595                 600                 605

Asn Lys Leu Thr Gln Ser Lys Ile Trp Asp Val Val Glu Lys Ala Asp
    610                 615                 620

Ile Gly Cys Thr Pro Gly Ser Gly Lys Asp Tyr Ala Gly Val Phe Ser
625                 630                 635                 640

Asp Ala Gly Leu Thr Phe Thr Ser Ser Ser Gly Gln Gln Thr Ala Gln
                645                 650                 655

Arg Ala Glu Leu Gln Cys Pro Gln Pro Ala Ala Arg Arg Arg Arg Ser
            660                 665                 670

Val Gln Leu Thr Glu Lys Arg Met Asp Lys Val Gly Lys Tyr Pro Lys
        675                 680                 685

Glu Leu Arg Lys Cys Cys Glu Asp Gly Met Arg Glu Asn Pro Met Arg
    690                 695                 700

Phe Ser Cys Gln Arg Arg Thr Arg Phe Ile Ser Leu Gly Glu Ala Cys
705                 710                 715                 720

Lys Lys Val Phe Leu Asp Cys Cys Asn Tyr Ile Thr Glu Leu Arg Arg
                725                 730                 735

Gln His Ala Arg Ala Ser His Leu Gly Leu Ala Arg Ser Asn Leu Asp
            740                 745                 750

Glu Asp Ile Ile Ala Glu Glu Asn Ile Val Ser Arg Ser Glu Phe Pro
        755                 760                 765

Glu Ser Trp Leu Trp Asn Val Glu Asp Leu Lys Glu Pro Pro Lys Asn
    770                 775                 780
```

```
Gly Ile Ser Thr Lys Leu Met Asn Ile Phe Leu Lys Asp Ser Ile Thr
785                 790                 795                 800

Thr Trp Glu Ile Leu Ala Val Ser Met Ser Asp Lys Lys Gly Ile Cys
            805                 810                 815

Val Ala Asp Pro Phe Glu Val Thr Val Met Gln Asp Phe Phe Ile Asp
        820                 825                 830

Leu Arg Leu Pro Tyr Ser Val Val Arg Asn Glu Gln Val Glu Ile Arg
    835                 840                 845

Ala Val Leu Tyr Asn Tyr Arg Gln Asn Gln Glu Leu Lys Val Arg Val
850                 855                 860

Glu Leu Leu His Asn Pro Ala Phe Cys Ser Leu Ala Thr Thr Lys Arg
865                 870                 875                 880

Arg His Gln Gln Thr Val Thr Ile Pro Pro Lys Ser Ser Leu Ser Val
            885                 890                 895

Pro Tyr Val Ile Val Pro Leu Lys Thr Gly Leu Gln Glu Val Glu Val
        900                 905                 910

Lys Ala Ala Val Tyr His His Phe Ile Ser Asp Gly Val Arg Lys Ser
    915                 920                 925

Leu Lys Val Val Pro Glu Gly Ile Arg Met Asn Lys Thr Val Ala Val
930                 935                 940

Arg Thr Leu Asp Pro Glu Arg Leu Gly Arg Gly Val Gln Lys Glu
945                 950                 955                 960

Asp Ile Pro Pro Ala Asp Leu Ser Asp Gln Val Pro Asp Thr Glu Ser
            965                 970                 975

Glu Thr Arg Ile Leu Leu Gln Gly Thr Pro Val Ala Gln Met Thr Glu
        980                 985                 990

Asp Ala Val Asp Ala Glu Arg Leu Lys His Leu Ile Val Thr Pro Ser
    995                 1000                1005

Gly Cys Gly Glu Gln Asn Met Ile Gly Met Thr Pro Thr Val Ile Ala
    1010                1015                1020

Val His Tyr Leu Asp Glu Thr Glu Gln Trp Glu Lys Phe Gly Leu Glu
1025                1030                1035                1040

Lys Arg Gln Gly Ala Leu Glu Leu Ile Lys Lys Gly Tyr Thr Gln Gln
            1045                1050                1055

Leu Ala Phe Arg Gln Pro Ser Ser Ala Phe Ala Ala Phe Val Lys Arg
        1060                1065                1070

Ala Pro Ser Thr Trp Leu Thr Ala Tyr Val Val Lys Val Phe Ser Leu
    1075                1080                1085

Ala Val Asn Leu Ile Ala Ile Asp Ser Gln Val Leu Cys Gly Ala Val
    1090                1095                1100

Lys Trp Leu Ile Leu Glu Lys Gln Lys Pro Asp Gly Val Phe Gln Glu
1105                1110                1115                1120

Asp Ala Pro Val Ile His Gln Glu Met Ile Gly Gly Leu Arg Asn Asn
            1125                1130                1135

Asn Glu Lys Asp Met Ala Leu Thr Ala Phe Val Leu Ile Ser Leu Gln
        1140                1145                1150

Glu Ala Lys Asp Ile Cys Glu Glu Gln Val Asn Ser Leu Pro Gly Ser
    1155                1160                1165

Ile Thr Lys Ala Gly Asp Phe Leu Glu Ala Asn Tyr Met Asn Leu Gln
    1170                1175                1180

Arg Ser Tyr Thr Val Ala Ile Ala Gly Tyr Ala Leu Ala Gln Met Gly
1185                1190                1195                1200
```

-continued

Arg Leu Lys Gly Pro Leu Leu Asn Lys Phe Leu Thr Thr Ala Lys Asp
            1205                1210                1215

Lys Asn Arg Trp Glu Asp Pro Gly Lys Gln Leu Tyr Asn Val Glu Ala
        1220                1225                1230

Thr Ser Tyr Ala Leu Leu Ala Leu Leu Gln Leu Lys Asp Phe Asp Phe
    1235                1240                1245

Val Pro Pro Val Val Arg Trp Leu Asn Glu Gln Arg Tyr Tyr Gly Gly
1250                1255                1260

Gly Tyr Gly Ser Thr Gln Ala Thr Phe Met Val Phe Gln Ala Leu Ala
1265                1270                1275                1280

Gln Tyr Gln Lys Asp Ala Pro Asp His Gln Glu Leu Asn Leu Asp Val
            1285                1290                1295

Ser Leu Gln Leu Pro Ser Arg Ser Ser Lys Ile Thr His Arg Ile His
        1300                1305                1310

Trp Glu Ser Ala Ser Leu Leu Arg Ser Glu Glu Thr Lys Glu Asn Glu
    1315                1320                1325

Gly Phe Thr Val Thr Ala Glu Gly Lys Gly Gln Gly Thr Leu Ser Val
1330                1335                1340

Val Thr Met Tyr His Ala Lys Ala Lys Asp Gln Leu Thr Cys Asn Lys
1345                1350                1355                1360

Phe Asp Leu Lys Val Thr Ile Lys Pro Ala Pro Glu Thr Glu Lys Arg
            1365                1370                1375

Pro Gln Asp Ala Lys Asn Thr Met Ile Leu Glu Ile Cys Thr Arg Tyr
        1380                1385                1390

Arg Gly Asp Gln Asp Ala Thr Met Ser Ile Leu Asp Ile Ser Met Met
    1395                1400                1405

Thr Gly Phe Ala Pro Asp Thr Asp Asp Leu Lys Gln Leu Ala Asn Gly
1410                1415                1420

Val Asp Arg Tyr Ile Ser Lys Tyr Glu Leu Asp Lys Ala Phe Ser Asp
1425                1430                1435                1440

Arg Asn Thr Leu Ile Ile Tyr Leu Asp Lys Val Ser His Ser Glu Asp
            1445                1450                1455

Asp Cys Leu Ala Phe Lys Val His Gln Tyr Phe Asn Val Glu Leu Ile
        1460                1465                1470

Gln Pro Gly Ala Val Lys Val Tyr Ala Tyr Tyr Asn Leu Glu Glu Ser
    1475                1480                1485

Cys Thr Arg Phe Tyr His Pro Glu Lys Glu Asp Gly Lys Leu Asn Lys
1490                1495                1500

Leu Cys Arg Asp Glu Leu Cys Arg Cys Ala Glu Glu Asn Cys Phe Ile
1505                1510                1515                1520

Gln Lys Ser Asp Asp Lys Val Thr Leu Glu Glu Arg Leu Asp Lys Ala
            1525                1530                1535

Cys Glu Pro Gly Val Asp Tyr Val Tyr Lys Thr Arg Leu Val Lys Val
        1540                1545                1550

Gln Leu Ser Asn Asp Phe Asp Glu Tyr Ile Met Ala Ile Glu Gln Thr
    1555                1560                1565

Ile Lys Ser Gly Ser Asp Glu Val Gln Val Gly Gln Gln Arg Thr Phe
1570                1575                1580

Ile Ser Pro Ile Lys Cys Arg Glu Ala Leu Lys Leu Glu Glu Lys Lys
1585                1590                1595                1600

His Tyr Leu Met Trp Gly Leu Ser Ser Asp Phe Trp Gly Glu Lys Pro
            1605                1610                1615

Asn Leu Ser Tyr Ile Ile Gly Lys Asp Thr Trp Val Glu His Trp Pro 1620              1625              1630
Glu Glu Asp Glu Cys Gln Asp Glu Glu Asn Gln Lys Gln Cys Gln Asp
     1635              1640              1645

Leu Gly Ala Phe Thr Glu Ser Met Val Val Phe Gly Cys Pro Asn
   1650              1655              1660

<210> SEQ ID NO 7
<211> LENGTH: 212
<212> TYPE: PRT
<213> ORGANISM: Homo sapiens
<220> FEATURE:
<223> OTHER INFORMATION: Neuroendocrine protein 7B2 precursor
<220> FEATURE:
<221> NAME/KEY: SIGNAL
<222> LOCATION: (1)..(26)
<223> OTHER INFORMATION: signal peptide
<220> FEATURE:
<221> NAME/KEY: PEPTIDE
<222> LOCATION: (27)..(212)
<223> OTHER INFORMATION: Neuroendocrine protein 7B2, (Neuroendocrine
      secretory protein 7B2, Neuroendocrine chaperone
      protein 7B2, secretory granule neuroendocrine
      protein I, secretogranin V)
<220> FEATURE:
<221> NAME/KEY: PEPTIDE
<222> LOCATION: (182)..(212)
<223> OTHER INFORMATION: biomarker peptide M3514.5, C-terminal fragment
      of Neuroendocrine protein 7B2

<400> SEQUENCE: 7

Met Val Ser Arg Met Val Ser Thr Met Leu Ser Gly Leu Leu Phe Trp
 1               5                  10                  15

Leu Ala Ser Gly Trp Thr Pro Ala Phe Ala Tyr Ser Pro Arg Thr Pro
             20                  25                  30

Asp Arg Val Ser Glu Ala Asp Ile Gln Arg Leu Leu His Gly Val Met
         35                  40                  45

Glu Gln Leu Gly Ile Ala Arg Pro Arg Val Glu Tyr Pro Ala His Gln
     50                  55                  60

Ala Met Asn Leu Val Gly Pro Gln Ser Ile Glu Gly Gly Ala His Glu
 65                  70                  75                  80

Gly Leu Gln His Leu Gly Pro Phe Gly Asn Ile Pro Asn Ile Val Ala
                 85                  90                  95

Glu Leu Thr Gly Asp Asn Ile Pro Lys Asp Phe Ser Glu Asp Gln Gly
            100                 105                 110

Tyr Pro Asp Pro Pro Asn Pro Cys Pro Val Gly Lys Thr Ala Asp Asp
        115                 120                 125

Gly Cys Leu Glu Asn Thr Pro Asp Thr Ala Glu Phe Ser Arg Glu Phe
    130                 135                 140

Gln Leu His Gln His Leu Phe Asp Pro Glu His Asp Tyr Pro Gly Leu
145                 150                 155                 160

Gly Lys Trp Asn Lys Lys Leu Leu Tyr Glu Lys Met Lys Gly Gly Glu
                165                 170                 175

Arg Arg Lys Arg Arg Ser Val Asn Pro Tyr Leu Gln Gly Gln Arg Leu
            180                 185                 190

Asp Asn Val Val Ala Lys Lys Ser Val Pro His Phe Ser Asp Glu Asp
        195                 200                 205

Lys Asp Pro Glu
    210

<210> SEQ ID NO 8
<211> LENGTH: 457

```
<212> TYPE: PRT
<213> ORGANISM: Homo sapiens
<220> FEATURE:
<223> OTHER INFORMATION: Chromogranin A precursor
<220> FEATURE:
<221> NAME/KEY: SIGNAL
<222> LOCATION: (1)..(18)
<223> OTHER INFORMATION: signal peptide
<220> FEATURE:
<221> NAME/KEY: PEPTIDE
<222> LOCATION: (19)..(457)
<223> OTHER INFORMATION: Chromogranin A (pituitary secretory protein I
      (SP-I))
<220> FEATURE:
<221> NAME/KEY: PEPTIDE
<222> LOCATION: (19)..(94)
<223> OTHER INFORMATION: vasostatin I
<220> FEATURE:
<221> NAME/KEY: PEPTIDE
<222> LOCATION: (19)..(131)
<223> OTHER INFORMATION: vasostatin II
<220> FEATURE:
<221> NAME/KEY: PEPTIDE
<222> LOCATION: (97)..(131)
<223> OTHER INFORMATION: biomarker peptide M3912.8, fragment of
      Chromogranin A
<220> FEATURE:
<221> NAME/KEY: PEPTIDE
<222> LOCATION: (272)..(319)
<223> OTHER INFORMATION: pancreastatin

<400> SEQUENCE: 8

Met Arg Ser Ala Ala Val Leu Ala Leu Leu Leu Cys Ala Gly Gln Val
 1               5                  10                  15

Thr Ala Leu Pro Val Asn Ser Pro Met Asn Lys Gly Asp Thr Glu Val
                20                  25                  30

Met Lys Cys Ile Val Glu Val Ile Ser Asp Thr Leu Ser Lys Pro Ser
            35                  40                  45

Pro Met Pro Val Ser Gln Glu Cys Phe Glu Thr Leu Arg Gly Asp Glu
        50                  55                  60

Arg Ile Leu Ser Ile Leu Arg His Gln Asn Leu Leu Lys Glu Leu Gln
 65                  70                  75                  80

Asp Leu Ala Leu Gln Gly Ala Lys Glu Arg Ala His Gln Gln Lys Lys
                85                  90                  95

His Ser Gly Phe Glu Asp Glu Leu Ser Glu Val Leu Glu Asn Gln Ser
            100                 105                 110

Ser Gln Ala Glu Leu Lys Glu Ala Val Glu Glu Pro Ser Ser Lys Asp
        115                 120                 125

Val Met Glu Lys Arg Glu Asp Ser Lys Glu Ala Glu Lys Ser Gly Glu
130                 135                 140

Ala Thr Asp Gly Ala Arg Pro Gln Ala Leu Pro Glu Pro Met Gln Glu
145                 150                 155                 160

Ser Lys Ala Glu Gly Asn Asn Gln Ala Pro Gly Glu Glu Glu Glu Glu
                165                 170                 175

Glu Glu Glu Ala Thr Asn Thr His Pro Pro Ala Ser Leu Pro Ser Gln
            180                 185                 190

Lys Tyr Pro Gly Pro Gln Ala Glu Gly Asp Ser Glu Gly Leu Ser Gln
        195                 200                 205

Gly Leu Val Asp Arg Glu Lys Gly Leu Ser Ala Glu Pro Gly Trp Gln
    210                 215                 220

Ala Lys Arg Glu Glu Glu Glu Glu Glu Glu Glu Ala Glu Ala Gly
225                 230                 235                 240

Glu Glu Ala Val Pro Glu Glu Glu Gly Pro Thr Val Val Leu Asn Pro
```

-continued

```
                245                 250                 255
His Pro Ser Leu Gly Tyr Lys Glu Ile Arg Lys Gly Glu Ser Arg Ser
            260                 265                 270

Glu Ala Leu Ala Val Asp Gly Ala Gly Lys Pro Gly Ala Glu Glu Ala
            275                 280                 285

Gln Asp Pro Glu Gly Lys Gly Glu Gln Glu His Ser Gln Gln Lys Glu
        290                 295                 300

Glu Glu Glu Met Ala Val Val Pro Gln Gly Leu Phe Arg Gly
305                 310                 315                 320

Lys Ser Gly Glu Leu Glu Gln Glu Glu Arg Leu Ser Lys Glu Trp
                325                 330                 335

Glu Asp Ser Lys Arg Trp Ser Lys Met Asp Gln Leu Ala Lys Glu Leu
            340                 345                 350

Thr Ala Glu Lys Arg Leu Glu Gly Gln Glu Glu Glu Asp Asn Arg
            355                 360                 365

Asp Ser Ser Met Lys Leu Ser Phe Arg Ala Arg Ala Tyr Gly Phe Arg
        370                 375                 380

Gly Pro Gly Pro Gln Leu Arg Arg Gly Trp Arg Pro Ser Arg Glu Glu
385                 390                 395                 400

Asp Ser Leu Glu Ala Gly Leu Pro Leu Gln Val Arg Gly Tyr Pro Glu
            405                 410                 415

Glu Lys Lys Glu Glu Glu Gly Ser Ala Asn Arg Arg Pro Glu Asp Gln
            420                 425                 430

Glu Leu Glu Ser Leu Ser Ala Ile Glu Ala Glu Leu Glu Lys Val Ala
            435                 440                 445

His Gln Leu Gln Ala Leu Arg Arg Gly
        450                 455

<210> SEQ ID NO 9
<211> LENGTH: 37
<212> TYPE: PRT
<213> ORGANISM: Homo sapiens
<220> FEATURE:
<223> OTHER INFORMATION: biomarker peptide M4352.4, C-terminal fragment
      of acute phase/inflammatory protein alpha-1-antichymotrypsin
      (serine/cysteine proteinase inhibitor, clade A, member 3)

<400> SEQUENCE: 9

Val Glu Thr Arg Thr Ile Val Arg Phe Asn Arg Pro Phe Leu Met Ile
1               5                   10                  15

Ile Val Pro Thr Asp Thr Gln Asn Ile Phe Phe Met Ser Lys Val Thr
            20                  25                  30

Asn Pro Lys Gln Ala
        35

<210> SEQ ID NO 10
<211> LENGTH: 43
<212> TYPE: PRT
<213> ORGANISM: Homo sapiens
<220> FEATURE:
<223> OTHER INFORMATION: biomarker peptide M4971, N-acetylated form of
      Thymosin beta-4
<220> FEATURE:
<221> NAME/KEY: MOD_RES
<222> LOCATION: (1)
<223> OTHER INFORMATION: Xaa = N-acetyl-serine

<400> SEQUENCE: 10

Xaa Asp Lys Pro Asp Met Ala Glu Ile Glu Lys Phe Asp Lys Ser Lys
1               5                   10                  15
```

```
Leu Lys Lys Thr Glu Thr Gln Glu Lys Asn Pro Leu Pro Ser Lys Glu
            20                  25                  30

Thr Ile Glu Gln Glu Lys Gln Ala Gly Glu Ser
            35                  40

<210> SEQ ID NO 11
<211> LENGTH: 314
<212> TYPE: PRT
<213> ORGANISM: Homo sapiens
<220> FEATURE:
<223> OTHER INFORMATION: Osteopontin precursor
<220> FEATURE:
<221> NAME/KEY: SIGNAL
<222> LOCATION: (1)..(16)
<223> OTHER INFORMATION: signal peptide
<220> FEATURE:
<221> NAME/KEY: PEPTIDE
<222> LOCATION: (17)..(314)
<223> OTHER INFORMATION: Osteopontin (bone sialoprotein 1, secreted
      phosphoprotein 1 (SPP-1), nephropontin, uropontin,
      urinary stone protein, early T-lymphocyte
      activation 1)
<220> FEATURE:
<221> NAME/KEY: PEPTIDE
<222> LOCATION: (249)..(314)
<223> OTHER INFORMATION: biomarker peptide 7653Da/7718 Da (IMAC-Cu SPA),
      C-terminal fragment of Osteopontin

<400> SEQUENCE: 11

Met Arg Ile Ala Val Ile Cys Phe Cys Leu Leu Gly Ile Thr Cys Ala
 1               5                  10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
            35                  40                  45

Ser Gln Lys Gln Asn Leu Leu Ala Pro Gln Asn Ala Val Ser Ser Glu
        50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Asp Glu Asp Asp Asp Asp His
                85                  90                  95

Val Asp Ser Gln Asp Ser Ile Asp Ser Asn Asp Ser Asp Asp Val Asp
            100                 105                 110

Asp Thr Asp Asp Ser His Gln Ser Asp Glu Ser His His Ser Asp Glu
        115                 120                 125

Ser Asp Glu Leu Val Thr Asp Phe Pro Thr Asp Leu Pro Ala Thr Glu
    130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Lys Phe Arg Arg
                165                 170                 175

Pro Asp Ile Gln Tyr Pro Asp Ala Thr Asp Glu Asp Ile Thr Ser His
            180                 185                 190

Met Glu Ser Glu Glu Leu Asn Gly Ala Tyr Lys Ala Ile Pro Val Ala
        195                 200                 205

Gln Asp Leu Asn Ala Pro Ser Asp Trp Asp Ser Arg Gly Lys Asp Ser
    210                 215                 220

Tyr Glu Thr Ser Gln Leu Asp Asp Gln Ser Ala Glu Thr His Ser His
225                 230                 235                 240

Lys Gln Ser Arg Leu Tyr Lys Arg Lys Ala Asn Asp Glu Ser Asn Glu
```

-continued

```
                  245                 250                 255
His Ser Asp Val Ile Asp Ser Gln Glu Leu Ser Lys Val Ser Arg Glu
            260                 265                 270

Phe His Ser His Glu Phe His Ser His Glu Asp Met Leu Val Val Asp
        275                 280                 285

Pro Lys Ser Lys Glu Glu Asp Lys His Leu Lys Phe Arg Ile Ser His
    290                 295                 300

Glu Leu Asp Ser Ala Ser Ser Glu Val Asn
305                 310

<210> SEQ ID NO 12
<211> LENGTH: 677
<212> TYPE: PRT
<213> ORGANISM: Homo sapiens
<220> FEATURE:
<223> OTHER INFORMATION: Chromogranin B precursor
<220> FEATURE:
<221> NAME/KEY: SIGNAL
<222> LOCATION: (1)..(20)
<223> OTHER INFORMATION: signal peptide
<220> FEATURE:
<221> NAME/KEY: PEPTIDE
<222> LOCATION: (21)..(677)
<223> OTHER INFORMATION: Chromogranin B (Secretogranin I)
<220> FEATURE:
<221> NAME/KEY: PEPTIDE
<222> LOCATION: (326)..(385)
<223> OTHER INFORMATION: biomarker peptide 7258 Da, processed fragment
      of Chromogranin B
<220> FEATURE:
<221> NAME/KEY: MOD_RES
<222> LOCATION: (341)
<223> OTHER INFORMATION: Xaa = sulfotyrosine

<400> SEQUENCE: 12

Met Gln Pro Thr Leu Leu Leu Ser Leu Leu Gly Ala Val Gly Leu Ala
  1               5                  10                  15

Ala Val Asn Ser Met Pro Val Asp Asn Arg Asn His Asn Glu Gly Met
            20                  25                  30

Val Thr Arg Cys Ile Ile Glu Val Leu Ser Asn Ala Leu Ser Lys Ser
        35                  40                  45

Ser Ala Pro Pro Ile Thr Pro Glu Cys Arg Gln Val Leu Lys Thr Ser
    50                  55                  60

Arg Lys Asp Val Lys Asp Lys Glu Thr Thr Glu Asn Glu Asn Thr Lys
65                  70                  75                  80

Phe Glu Val Arg Leu Leu Arg Asp Pro Ala Asp Ala Ser Glu Ala His
                85                  90                  95

Glu Ser Ser Ser Arg Gly Glu Ala Gly Ala Pro Gly Glu Glu Asp Ile
            100                 105                 110

Gln Gly Pro Thr Lys Ala Asp Thr Glu Lys Trp Ala Glu Gly Gly Gly
        115                 120                 125

His Ser Arg Glu Arg Ala Asp Glu Pro Gln Trp Ser Leu Tyr Pro Ser
    130                 135                 140

Asp Ser Gln Val Ser Glu Glu Val Lys Thr His Ser Glu Lys Ser
145                 150                 155                 160

Gln Arg Glu Asp Glu Glu Glu Glu Gly Glu Asn Tyr Gln Lys Gly
                165                 170                 175

Glu Arg Gly Glu Asp Ser Ser Glu Glu Lys His Leu Glu Glu Pro Gly
            180                 185                 190

Glu Thr Gln Asn Ala Phe Leu Asn Glu Arg Lys Gln Ala Ser Ala Ile
        195                 200                 205
```

-continued

```
Lys Lys Glu Glu Leu Val Ala Arg Ser Glu Thr His Ala Ala Gly His
    210                 215                 220

Ser Gln Glu Lys Thr His Ser Arg Glu Lys Ser Ser Gln Glu Ser Gly
225                 230                 235                 240

Glu Glu Ala Gly Ser Gln Glu Asn His Pro Gln Glu Ser Lys Gly Gln
                245                 250                 255

Pro Arg Ser Gln Glu Ser Glu Glu Gly Glu Glu Asp Ala Thr Ser
            260                 265                 270

Glu Val Asp Lys Arg Arg Thr Arg Pro Arg His His His Gly Arg Ser
        275                 280                 285

Arg Pro Asp Arg Ser Ser Gln Gly Gly Ser Leu Pro Ser Glu Glu Lys
    290                 295                 300

Gly His Pro Gln Glu Glu Ser Glu Ser Asn Val Ser Met Ala Ser
305                 310                 315                 320

Leu Gly Glu Lys Arg Asp His His Ser Thr His Tyr Arg Ala Ser Glu
                325                 330                 335

Glu Glu Pro Glu Xaa Gly Glu Glu Ile Lys Gly Tyr Pro Gly Val Gln
            340                 345                 350

Ala Pro Glu Asp Leu Glu Trp Glu Arg Tyr Arg Gly Arg Gly Ser Glu
        355                 360                 365

Glu Tyr Arg Ala Pro Arg Pro Gln Ser Glu Glu Ser Trp Asp Glu Glu
    370                 375                 380

Asp Lys Arg Asn Tyr Pro Ser Leu Glu Leu Asp Lys Met Ala His Gly
385                 390                 395                 400

Tyr Gly Glu Glu Ser Glu Glu Arg Gly Leu Glu Pro Gly Lys Gly
                405                 410                 415

Arg His His Arg Gly Arg Gly Gly Glu Pro Arg Ala Tyr Phe Met Ser
            420                 425                 430

Asp Thr Arg Glu Glu Lys Arg Phe Leu Gly Glu Gly His His Arg Val
        435                 440                 445

Gln Glu Asn Gln Met Asp Lys Ala Arg Arg His Pro Gln Gly Ala Trp
    450                 455                 460

Lys Glu Leu Asp Arg Asn Tyr Leu Asn Tyr Gly Glu Glu Gly Ala Pro
465                 470                 475                 480

Gly Lys Trp Gln Gln Gln Gly Asp Leu Gln Asp Thr Lys Glu Asn Arg
                485                 490                 495

Glu Glu Ala Arg Phe Gln Asp Lys Gln Tyr Ser Ser His His Thr Ala
            500                 505                 510

Glu Lys Arg Lys Arg Leu Gly Glu Leu Phe Asn Pro Tyr Tyr Asp Pro
        515                 520                 525

Leu Gln Trp Lys Ser Ser His Phe Glu Arg Arg Asp Asn Met Asn Asp
    530                 535                 540

Asn Phe Leu Glu Gly Glu Glu Asn Glu Leu Thr Leu Asn Glu Lys
545                 550                 555                 560

Asn Phe Phe Pro Glu Tyr Asn Tyr Asp Trp Trp Glu Lys Lys Pro Phe
                565                 570                 575

Ser Glu Asp Val Asn Trp Gly Tyr Glu Lys Arg Asn Leu Ala Arg Val
            580                 585                 590

Pro Lys Leu Asp Leu Lys Arg Gln Tyr Asp Arg Val Ala Gln Leu Asp
        595                 600                 605

Gln Leu Leu His Tyr Arg Lys Lys Ser Ala Glu Phe Pro Asp Phe Tyr
    610                 615                 620
```

```
Asp Ser Glu Glu Pro Val Ser Thr His Gln Glu Ala Glu Asn Glu Lys
625                 630                 635                 640

Asp Arg Ala Asp Gln Thr Val Leu Thr Glu Asp Glu Lys Lys Glu Leu
            645                 650                 655

Glu Asn Leu Ala Ala Met Asp Leu Glu Leu Gln Lys Ile Ala Glu Lys
        660                 665                 670

Phe Ser Gln Arg Gly
        675

<210> SEQ ID NO 13
<211> LENGTH: 457
<212> TYPE: PRT
<213> ORGANISM: Homo sapiens
<220> FEATURE:
<223> OTHER INFORMATION: Chromogranin A precursor
<220> FEATURE:
<221> NAME/KEY: SIGNAL
<222> LOCATION: (1)..(18)
<223> OTHER INFORMATION: signal peptide
<220> FEATURE:
<221> NAME/KEY: PEPTIDE
<222> LOCATION: (19)..(457)
<223> OTHER INFORMATION: Chromogranin A (pituitary secretory protein I
      (SP-I))
<220> FEATURE:
<221> NAME/KEY: PEPTIDE
<222> LOCATION: (134)..(225)
<223> OTHER INFORMATION: biomarker peptide 9730 Da, 9.8 kDa (Q10), EA-92
      peptide of Chromogranin A
<220> FEATURE:
<221> NAME/KEY: PEPTIDE
<222> LOCATION: (228)..(260)
<223> OTHER INFORMATION: ES-43 peptide of Chromogranin A
<220> FEATURE:
<221> NAME/KEY: PEPTIDE
<222> LOCATION: (322)..(339)
<223> OTHER INFORMATION: SS-18 peptide of Chromogranin A
<220> FEATURE:
<221> NAME/KEY: PEPTIDE
<222> LOCATION: (342)..(349)
<223> OTHER INFORMATION: WA-8 peptide of Chromogranin A
<220> FEATURE:
<221> NAME/KEY: PEPTIDE
<222> LOCATION: (342)..(355)
<223> OTHER INFORMATION: WE-14 peptide of Chromogranin A
<220> FEATURE:
<221> NAME/KEY: PEPTIDE
<222> LOCATION: (358)..(376)
<223> OTHER INFORMATION: LF-19 peptide of Chromogranin A
<220> FEATURE:
<221> NAME/KEY: PEPTIDE
<222> LOCATION: (380)..(390)
<223> OTHER INFORMATION: AL-11 peptide of Chromogranin A
<220> FEATURE:
<221> NAME/KEY: PEPTIDE
<222> LOCATION: (393)..(411)
<223> OTHER INFORMATION: GV-19 peptide of Chromogranin A
<220> FEATURE:
<221> NAME/KEY: PEPTIDE
<222> LOCATION: (413)..(456)
<223> OTHER INFORMATION: GR-44 peptide of Chromogranin A
<220> FEATURE:
<221> NAME/KEY: PEPTIDE
<222> LOCATION: (420)..(456)
<223> OTHER INFORMATION: ER-37 peptide of Chromogranin A

<400> SEQUENCE: 13

Met Arg Ser Ala Ala Val Leu Ala Leu Leu Leu Cys Ala Gly Gln Val
1               5                   10                  15

Thr Ala Leu Pro Val Asn Ser Pro Met Asn Lys Gly Asp Thr Glu Val
            20                  25                  30

Met Lys Cys Ile Val Glu Val Ile Ser Asp Thr Leu Ser Lys Pro Ser
```

```
            35                  40                  45
Pro Met Pro Val Ser Gln Glu Cys Phe Glu Thr Leu Arg Gly Asp Glu
    50                  55                  60

Arg Ile Leu Ser Ile Leu Arg His Gln Asn Leu Leu Lys Glu Leu Gln
65                  70                  75                  80

Asp Leu Ala Leu Gln Gly Ala Lys Glu Arg Ala His Gln Gln Lys Lys
                85                  90                  95

His Ser Gly Phe Glu Asp Glu Leu Ser Glu Val Leu Glu Asn Gln Ser
            100                 105                 110

Ser Gln Ala Glu Leu Lys Glu Ala Val Glu Glu Pro Ser Ser Lys Asp
        115                 120                 125

Val Met Glu Lys Arg Glu Asp Ser Lys Glu Ala Glu Lys Ser Gly Glu
    130                 135                 140

Ala Thr Asp Gly Ala Arg Pro Gln Ala Leu Pro Glu Pro Met Gln Glu
145                 150                 155                 160

Ser Lys Ala Glu Gly Asn Asn Gln Ala Pro Gly Glu Glu Glu Glu Glu
                165                 170                 175

Glu Glu Glu Ala Thr Asn Thr His Pro Pro Ala Ser Leu Pro Ser Gln
            180                 185                 190

Lys Tyr Pro Gly Pro Gln Ala Glu Gly Asp Ser Glu Gly Leu Ser Gln
        195                 200                 205

Gly Leu Val Asp Arg Glu Lys Gly Leu Ser Ala Glu Pro Gly Trp Gln
    210                 215                 220

Ala Lys Arg Glu Glu Glu Glu Glu Glu Glu Ala Glu Ala Gly
225                 230                 235                 240

Glu Glu Ala Val Pro Glu Glu Glu Gly Pro Thr Val Val Leu Asn Pro
                245                 250                 255

His Pro Ser Leu Gly Tyr Lys Glu Ile Arg Lys Gly Glu Ser Arg Ser
            260                 265                 270

Glu Ala Leu Ala Val Asp Gly Ala Gly Lys Pro Gly Ala Glu Glu Ala
        275                 280                 285

Gln Asp Pro Glu Gly Lys Gly Glu Gln Glu His Ser Gln Gln Lys Glu
    290                 295                 300

Glu Glu Glu Glu Met Ala Val Val Pro Gln Gly Leu Phe Arg Gly Gly
305                 310                 315                 320

Lys Ser Gly Glu Leu Glu Gln Glu Glu Glu Arg Leu Ser Lys Glu Trp
                325                 330                 335

Glu Asp Ser Lys Arg Trp Ser Lys Met Asp Gln Leu Ala Lys Glu Leu
            340                 345                 350

Thr Ala Glu Lys Arg Leu Glu Gly Gln Glu Glu Glu Asp Asn Arg
        355                 360                 365

Asp Ser Ser Met Lys Leu Ser Phe Arg Ala Arg Ala Tyr Gly Phe Arg
    370                 375                 380

Gly Pro Gly Pro Gln Leu Arg Arg Gly Trp Arg Pro Ser Arg Glu Glu
385                 390                 395                 400

Asp Ser Leu Glu Ala Gly Leu Pro Leu Gln Val Arg Gly Tyr Pro Glu
                405                 410                 415

Glu Lys Lys Glu Glu Glu Gly Ser Ala Asn Arg Arg Pro Glu Asp Gln
            420                 425                 430

Glu Leu Glu Ser Leu Ser Ala Ile Glu Ala Glu Leu Glu Lys Val Ala
        435                 440                 445

His Gln Leu Gln Ala Leu Arg Arg Gly
    450                 455
```

<210> SEQ ID NO 14
<211> LENGTH: 615
<212> TYPE: PRT
<213> ORGANISM: Homo sapiens
<220> FEATURE:
<223> OTHER INFORMATION: nerve growth factor inducible Neurosecretory
    protein vaccinia virus growth factor (VGF)
    precursor
<220> FEATURE:
<221> NAME/KEY: SIGNAL
<222> LOCATION: (1)..(22)
<223> OTHER INFORMATION: signal peptide
<220> FEATURE:
<221> NAME/KEY: PEPTIDE
<222> LOCATION: (23)..(615)
<223> OTHER INFORMATION: nerve growth factor inducible Neurosecretory
    protein vaccinia virus growth factor (VGF)
<220> FEATURE:
<221> NAME/KEY: PEPTIDE
<222> LOCATION: (373)..(417)
<223> OTHER INFORMATION: biomarker peptide 4808 Da, 4812 Da (Q10),
    processed fragment of nerve growth factor
    inducible Neurosecretory protein vaccinia virus
    growth factor (VGF)

<400> SEQUENCE: 14

Met Lys Ala Leu Arg Leu Ser Ala Ser Ala Leu Phe Cys Leu Leu Leu
 1               5                  10                  15

Ile Asn Gly Leu Gly Ala Ala Pro Pro Gly Arg Pro Glu Ala Gln Pro
             20                  25                  30

Pro Pro Leu Ser Ser Glu His Lys Glu Pro Val Ala Gly Asp Ala Val
         35                  40                  45

Pro Gly Pro Lys Asp Gly Ser Ala Pro Glu Val Arg Gly Ala Arg Asn
     50                  55                  60

Ser Glu Pro Gln Asp Glu Gly Glu Leu Phe Gln Gly Val Asp Pro Arg
 65                  70                  75                  80

Ala Leu Ala Ala Val Leu Leu Gln Ala Leu Asp Arg Pro Ala Ser Pro
                 85                  90                  95

Pro Ala Pro Ser Gly Ser Gln Gln Gly Pro Glu Glu Glu Ala Ala Glu
            100                 105                 110

Ala Leu Leu Thr Glu Thr Val Arg Ser Gln Thr His Ser Leu Pro Ala
        115                 120                 125

Pro Glu Ser Pro Glu Pro Ala Ala Pro Pro Arg Pro Gln Thr Pro Glu
    130                 135                 140

Asn Gly Pro Glu Ala Ser Asp Pro Ser Glu Glu Leu Glu Ala Leu Ala
145                 150                 155                 160

Ser Leu Leu Gln Glu Leu Arg Asp Phe Ser Pro Ser Ser Ala Lys Arg
                165                 170                 175

Gln Gln Glu Thr Ala Ala Ala Glu Thr Glu Thr Arg Thr His Thr Leu
            180                 185                 190

Thr Arg Val Asn Leu Glu Ser Pro Gly Pro Glu Arg Val Trp Arg Ala
        195                 200                 205

Ser Trp Gly Glu Phe Gln Ala Arg Val Pro Glu Arg Ala Pro Leu Pro
    210                 215                 220

Pro Pro Ala Pro Ser Gln Phe Gln Ala Arg Met Pro Asp Ser Gly Pro
225                 230                 235                 240

Leu Pro Glu Thr His Lys Phe Gly Glu Gly Val Ser Ser Pro Lys Thr
                245                 250                 255

His Leu Gly Glu Ala Leu Ala Pro Leu Ser Lys Ala Tyr Gln Gly Val
            260                 265                 270

```
Ala Ala Pro Phe Pro Lys Ala Arg Arg Pro Glu Ser Ala Leu Leu Gly
        275                 280                 285
Gly Ser Glu Ala Gly Glu Arg Leu Leu Gln Gln Gly Leu Ala Gln Val
        290                 295                 300
Glu Ala Gly Arg Arg Gln Ala Glu Ala Thr Arg Gln Ala Ala Ala Gln
305                 310                 315                 320
Glu Glu Arg Leu Ala Asp Leu Ala Ser Asp Leu Leu Leu Gln Tyr Leu
                325                 330                 335
Leu Gln Gly Gly Ala Arg Gln Arg Gly Leu Gly Gly Arg Gly Leu Gln
            340                 345                 350
Glu Ala Ala Glu Glu Arg Glu Ser Ala Arg Glu Glu Glu Glu Ala Glu
        355                 360                 365
Gln Glu Arg Arg Gly Gly Glu Glu Arg Val Gly Glu Glu Asp Glu Glu
    370                 375                 380
Ala Ala Glu Ala Glu Ala Glu Ala Glu Ala Glu Arg Ala Arg Gln
385                 390                 395                 400
Asn Ala Leu Leu Phe Ala Glu Glu Asp Gly Glu Ala Gly Ala Glu
                405                 410                 415
Asp Lys Arg Ser Gln Glu Glu Thr Pro Gly His Arg Arg Lys Glu Ala
            420                 425                 430
Glu Gly Thr Glu Glu Gly Gly Glu Glu Asp Asp Glu Glu Met Asp
        435                 440                 445
Pro Gln Thr Ile Asp Ser Leu Ile Glu Leu Ser Thr Lys Leu His Leu
    450                 455                 460
Pro Ala Asp Asp Val Val Ser Ile Ile Glu Glu Val Glu Glu Lys Arg
465                 470                 475                 480
Lys Arg Lys Lys Asn Ala Pro Pro Glu Pro Val Pro Pro Arg Ala
                485                 490                 495
Ala Pro Ala Pro Thr His Val Arg Ser Pro Gln Pro Pro Pro Pro Ala
            500                 505                 510
Pro Ala Pro Ala Arg Asp Glu Leu Pro Asp Trp Asn Glu Val Leu Pro
        515                 520                 525
Pro Trp Asp Arg Glu Glu Asp Glu Val Tyr Pro Pro Gly Pro Tyr His
    530                 535                 540
Pro Phe Pro Asn Tyr Ile Arg Pro Arg Thr Leu Gln Pro Pro Ser Ala
545                 550                 555                 560
Leu Arg Arg Arg His Tyr His His Ala Leu Pro Pro Ser Arg His Tyr
                565                 570                 575
Pro Gly Arg Glu Ala Gln Ala Arg Arg Ala Gln Glu Glu Ala Glu Ala
            580                 585                 590
Glu Glu Arg Arg Leu Gln Glu Gln Glu Glu Leu Glu Asn Tyr Ile Glu
        595                 600                 605
His Val Leu Leu Arg Arg Pro
    610                 615

<210> SEQ ID NO 15
<211> LENGTH: 770
<212> TYPE: PRT
<213> ORGANISM: Homo sapiens
<220> FEATURE:
<223> OTHER INFORMATION: Amyloid beta A4 precursor (APP, ABPP), isoform
      a, protease nexin II (PN-II), cerebral vascular amyloid peptide
      (CVAP), amyloid-beta protein, beta-amyloid peptide, A4 amyloid
      protein, Alzheimer's disease amyloid protein
<220> FEATURE:
<221> NAME/KEY: SIGNAL
```

<222> LOCATION: (1)..(17)
<223> OTHER INFORMATION: signal peptide
<220> FEATURE:
<221> NAME/KEY: PEPTIDE
<222> LOCATION: (1)..(40)
<223> OTHER INFORMATION: biomarker peptide 4320 Da (IMAC-Ni), A-beta
      1-40 peptide fragment of Amyloid beta A4 precursor
<220> FEATURE:
<221> NAME/KEY: PEPTIDE
<222> LOCATION: (18)..(687)
<223> OTHER INFORMATION: soluble APP-alpha
<220> FEATURE:
<221> NAME/KEY: PEPTIDE
<222> LOCATION: (18)..(671)
<223> OTHER INFORMATION: soluble APP-beta
<220> FEATURE:
<221> NAME/KEY: PEPTIDE
<222> LOCATION: (672)..(770)
<223> OTHER INFORMATION: C99
<220> FEATURE:
<221> NAME/KEY: PEPTIDE
<222> LOCATION: (672)..(713)
<223> OTHER INFORMATION: beta-amyloid protein 42
<220> FEATURE:
<221> NAME/KEY: PEPTIDE
<222> LOCATION: (672)..(711)
<223> OTHER INFORMATION: biomarker peptide 4330 Da, fragment of Amyloid
      beta A4 precursor, beta-amyloid protein 40
<220> FEATURE:
<221> NAME/KEY: PEPTIDE
<222> LOCATION: (688)..(770)
<223> OTHER INFORMATION: C83
<220> FEATURE:
<221> NAME/KEY: PEPTIDE
<222> LOCATION: (688)..(713)
<223> OTHER INFORMATION: P3(42)
<220> FEATURE:
<221> NAME/KEY: PEPTIDE
<222> LOCATION: (688)..(711)
<223> OTHER INFORMATION: P3(40)
<220> FEATURE:
<221> NAME/KEY: PEPTIDE
<222> LOCATION: (712)..(770)
<223> OTHER INFORMATION: gamma-CTF(59)
<220> FEATURE:
<221> NAME/KEY: PEPTIDE
<222> LOCATION: (714)..(770)
<223> OTHER INFORMATION: gamma-CTF(57)
<220> FEATURE:
<221> NAME/KEY: PEPTIDE
<222> LOCATION: (721)..(770)
<223> OTHER INFORMATION: gamma-CTF(50)
<220> FEATURE:
<221> NAME/KEY: PEPTIDE
<222> LOCATION: (740)..(770)
<223> OTHER INFORMATION: C31

<400> SEQUENCE: 15

Met Leu Pro Gly Leu Ala Leu Leu Leu Ala Ala Trp Thr Ala Arg
 1               5                  10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

-continued

```
Ile Pro Tyr Arg Cys Leu Val Gly Glu Phe Val Ser Asp Ala Leu Leu
            115                 120                 125
Val Pro Asp Lys Cys Lys Phe Leu His Gln Glu Arg Met Asp Val Cys
130                 135                 140
Glu Thr His Leu His Trp His Thr Val Ala Lys Glu Thr Cys Ser Glu
145                 150                 155                 160
Lys Ser Thr Asn Leu His Asp Tyr Gly Met Leu Leu Pro Cys Gly Ile
                165                 170                 175
Asp Lys Phe Arg Gly Val Glu Phe Val Cys Cys Pro Leu Ala Glu Glu
            180                 185                 190
Ser Asp Asn Val Asp Ser Ala Asp Ala Glu Glu Asp Asp Ser Asp Val
        195                 200                 205
Trp Trp Gly Gly Ala Asp Thr Asp Tyr Ala Asp Gly Ser Glu Asp Lys
    210                 215                 220
Val Val Glu Val Ala Glu Glu Glu Val Ala Glu Val Glu Glu Glu Glu
225                 230                 235                 240
Glu Ala Asp Asp Asp Glu Asp Asp Glu Asp Gly Asp Glu Val Glu Glu
                245                 250                 255
Glu Ala Glu Glu Pro Tyr Glu Glu Ala Thr Glu Arg Thr Thr Ser Ile
            260                 265                 270
Ala Thr Thr Thr Thr Thr Thr Glu Ser Val Glu Glu Val Val Arg
        275                 280                 285
Glu Val Cys Ser Glu Gln Ala Glu Thr Gly Pro Cys Arg Ala Met Ile
    290                 295                 300
Ser Arg Trp Tyr Phe Asp Val Thr Glu Gly Lys Cys Ala Pro Phe Phe
305                 310                 315                 320
Tyr Gly Gly Cys Gly Asn Arg Asn Asn Phe Asp Thr Glu Glu Tyr
                325                 330                 335
Cys Met Ala Val Cys Gly Ser Ala Met Ser Gln Ser Leu Leu Lys Thr
            340                 345                 350
Thr Gln Glu Pro Leu Ala Arg Asp Pro Val Lys Leu Pro Thr Thr Ala
        355                 360                 365
Ala Ser Thr Pro Asp Ala Val Asp Lys Tyr Leu Glu Thr Pro Gly Asp
    370                 375                 380
Glu Asn Glu His Ala His Phe Gln Lys Ala Lys Glu Arg Leu Glu Ala
385                 390                 395                 400
Lys His Arg Glu Arg Met Ser Gln Val Met Arg Glu Trp Glu Glu Ala
                405                 410                 415
Glu Arg Gln Ala Lys Asn Leu Pro Lys Ala Asp Lys Lys Ala Val Ile
            420                 425                 430
Gln His Phe Gln Glu Lys Val Glu Ser Leu Glu Gln Glu Ala Ala Asn
        435                 440                 445
Glu Arg Gln Gln Leu Val Glu Thr His Met Ala Arg Val Glu Ala Met
    450                 455                 460
Leu Asn Asp Arg Arg Arg Leu Ala Leu Glu Asn Tyr Ile Thr Ala Leu
465                 470                 475                 480
Gln Ala Val Pro Pro Arg Pro Arg His Val Phe Asn Met Leu Lys Lys
                485                 490                 495
Tyr Val Arg Ala Glu Gln Lys Asp Arg Gln His Thr Leu Lys His Phe
            500                 505                 510
Glu His Val Arg Met Val Asp Pro Lys Lys Ala Ala Gln Ile Arg Ser
        515                 520                 525
```

```
Gln Val Met Thr His Leu Arg Val Ile Tyr Glu Arg Met Asn Gln Ser
        530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
            580                 585                 590

Leu Met Pro Ser Leu Thr Glu Thr Lys Thr Thr Val Glu Leu Leu Pro
        595                 600                 605

Val Asn Gly Glu Phe Ser Leu Asp Asp Leu Gln Pro Trp His Ser Phe
    610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
                660                 665                 670

Ala Glu Phe Arg His Asp Ser Gly Tyr Glu Val His His Gln Lys Leu
            675                 680                 685

Val Phe Phe Ala Glu Asp Val Gly Ser Asn Lys Gly Ala Ile Ile Gly
        690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
                740                 745                 750

Gln Gln Asn Gly Tyr Glu Asn Pro Thr Tyr Lys Phe Phe Glu Gln Met
            755                 760                 765

Gln Asn
    770

<210> SEQ ID NO 16
<211> LENGTH: 34
<212> TYPE: PRT
<213> ORGANISM: Homo sapiens
<220> FEATURE:
<223> OTHER INFORMATION: biomarker peptide 4146 Da (Q10), C-terminal
      fragment of Protease C1 inhibitor

<400> SEQUENCE: 16

Thr Leu Leu Val Phe Glu Val Gln Gln Pro Phe Leu Phe Val Leu Trp
  1               5                   10                  15

Asp Gln Gln His Lys Phe Pro Val Phe Met Gly Arg Val Tyr Asp Pro
                20                  25                  30

Arg Ala
```

BIOMARKERS FOR ALZHEIMER'S DISEASE

CROSS-REFERENCE TO RELATED APPLICATIONS

This application claims the benefit of U.S. provisional patent application No. 60/518,360, filed Nov. 7, 2003; U.S. provisional patent application No. 60/526,753, filed Dec. 2, 2003; U.S. provisional patent application No. 60/546,423, filed Feb. 19, 2004; U.S. provisional patent application No. 60/547,250, filed Feb. 23, 2004; U.S. provisional patent application No. 60/558,896, filed Apr. 2, 2004; U.S. provisional patent application No. 60/572,617, filed May 18, 2004; and U.S. provisional patent application No. 60/586,503, filed Jul. 8, 2004, the disclosure of each of which is incorporated herein by reference in its entirety for all purposes.

BACKGROUND OF THE INVENTION

Alzheimer's Disease is a progressive neurodegenerative disorder that leads to the death of brain cells that cannot be replaced once lost. The two key neuropathological hallmarks of AD are the presence of senile plaques predominantly comprised of aggregated beta-amyloid protein (Aβ) and neurofibrillary tangles (NFTs) formed by the accumulation of hyperphosphorylated tau protein. Currently, the clinical diagnosis of AD requires an evaluation of medical history and physical examination including neurological, neuropsychological and psychiatric assessment, as well as various biological, radiological and electrophysiological tests. Despite the battery of tests, a definitive diagnosis can only be achieved by post-mortem brain examination. Therefore, there is an unmet need for a simple biochemical test that can detect AD at an early stage, monitor progression of the disease, and discriminate between AD, normal, non-AD dementias and other neurological disorders.

Three different biomarkers in Cerebrospinal Fluid (CSF) have been particularly well researched: neuronal thread protein, tau and derivatives of amyloid precursor protein (APP).

Neuronal thread protein is known to be overexpressed in brain neurons in AD patients. The company NYMOX has developed a quantitative test for measuring levels of a specific type of neuronal thread protein (AD7c-NTP) in CSF and urine. Quite a number of studies have evaluated CSF-tau as an ante-mortem marker for AD mainly using enzyme-linked immunoabsorbent assays (ELISA) as the measurement assay. In most of these studies, total tau has been measured although there is an increasing body of literature also describing the analysis of phosphorylated variants of the same protein involved in the formation of NFTs. ELISAs that can distinguish between the major form of Aβ ending at amino acid 40 (Aβ40) and the senile plaque forming species ending at position 42 (Aβ42) have also been developed and evaluated extensively for CSF analysis. All three assays, either used individually, or in the case of tau and Aβ42, in combination, do not have the required sensitivity and specificity values for routine clinical use, particularly for early diagnosis and discrimination between AD and other non-AD dementias. In addition, attempts to measure tau and Aβ42 in blood have been met with limited success, further restricting their widespread adoption into clinical practice.

A wide spectrum of other aberrations, other than NTP, Tau and Aβ, has been reported in AD patient CSF. Many of the identified (protein sequence confirmed) CSF markers reported herein have been shown to be either increased or decreased in AD patients versus normal individuals. For example, the protein Ubiquitin is known to complex with hyperphosphorylated Tau during maturation of NFTs in the brains of AD patients (Iqbal et. al. *J Neural Transm Suppl.* 53:169-80 (1998)). Ubiquitin levels in CSF of AD and neurological control groups have been shown to be significantly higher than those of non-neurological aged controls (Wang et. al. *Acta Neuropathol (Berl).* 82(1):6-12 (1991); Kudo et. al. *Brain Res.* 639(1):1-7 (1994)).

The acute phase/inflammatory protein alpha(1)-antichymotrypsin (ACT) is overproduced in the AD brain. ACT also can promote the formation of, and is associated with, neurotoxic amyloid deposits (Potter et. al. *Neurobiol Aging.* 22(6): 923-30 (2001)). The levels of ACT in both serum and CSF are significantly and specifically higher in patients with Alzheimer-type dementia than in control subjects (Matsubara et. al. *Ann Neurol.* 28(4):561-7(1990)). There is a particularly close association of increases in CSF-ACT with late onset AD (Harigaya et. al. *Intern Med.* 34(6):481-4 (1995)).

Chromogranin A (CrA) is the major protein of large dense-core synaptic vesicles and may be of value as a biochemical marker for synaptic function in AD. One report described no difference between the AD, vascular dementia, and age-matched control groups except when comparing a familial subtype (AD Type I) with controls where there was a statistically significant elevation of CSF CrA in the diseased individuals (Blennow et. al. *Dementia.* 6(6):306-11 (1995)).

Beta-2-Microglobulin (B2M) is an initiator of inflammatory responses modulated by interferons and certain cytokines (Hoekman et. al. *Neth. J. Med.* 28:551-557 (1985)). A proteome analysis of CSF by two-dimensional electrophoresis (2D-gel) has shown a significant increase of B2M in AD patients (Davidsson et al., *Neuroreport,* 13:611-615 (2002)), and more recently these results were confirmed by SELDI analysis (Carrette, O. et. al., *Proteomics,* 3:1486-1494 (2003)).

Transthyretin (TTR) has been shown to interact with Aβ, possibly preventing amyloid formation in biological fluids and in the brain. (Tsuzuki et al., *Neurosci Lett,* 10:171-174 (2000)). One identified TTR isoform was shown to be increased in AD-CSF using 2D gel analysis of a small number of AD and control patients (Davidsson, supra.). However, this result conflicts with other reports showing a clear decrease of TTR in CSF from AD patients compared with controls (Serot et. al. *J Neurol Neurosurg Psychiatry.* 63(4):506-8 (1997); Riisoen et. al. *Acta Neurol Scand.* 78(6):455-9 (1998)). This decrease is also negatively correlated with the senile plaque (SP) abundance (Merched et. al. *FEBS Lett.* 425(2):225-8 (1998)).

Cystatin C, a cysteine protease inhibitor, has been implicated in the neurodegenerative and repair processes of the nervous system, and the deposition of the same protein together with beta amyloid peptide was found as cerebral amyloid angiopathy (CAA) in different types of dementias (Levy et. al. *J. Neuropathol. Exp. Neurol.* 60:94-104). Full length Cystatin C was found as a CSF marker for AD in a previous SELDI profiling study (Carrette, supra.). A relative blood-brain barrier (BBB) dysfunction is associated with AD among very elderly individuals. The CSF/serum albumin ratio can be used as a measure of BBB function. Mean CSF/serum albumin ratio has been reported to be higher in all dementias studied, including AD, than in nondemented individuals (Skoog et al, *Neurology.* 50:966-71 (1998)).

Transferrin (TF) plays a role in anti-oxidant defense in serum and is also produced in the brain where its role in oxidative stress is unclear. A study on Down's syndrome patients suffering from progressive dementia showed decreased levels of TF when compared to age-matched controls with no neurological disease (Elovaara Acta Neurol Scand. 69(5):302-5(1994)).

Prior studies evaluating the different biochemical markers in the CSF of dementia patients have employed assay methods, such as ELISA, that use indirect means of measuring the analyte of interest. These methods are not capable of discerning the different processed forms of proteins revealed other processes. Furthermore, traditional assay methods have left unexplored avenues of treatment relating to the different processed forms of proteins. Thus, a need exists for methods which diagnosis Alzheimer's disease before significant neuronal loss has occurred, and for therapeutic treatments to prevent progression of the disease.

SUMMARY OF THE INVENTION

The present invention provides polypeptide-based biomarkers that are differentially present in subjects having Alzheimer's disease versus subjects free of the disease and/or versus subjects suffering from forms of non-Alzheimer's dementia (e.g., LBD, FTD, etc.). In addition, the present invention provides methods of using the polypeptide-based biomarkers to qualify Alzheimer's disease in a subject. The present invention also provides methods for identifying Alzheimer's disease therapeutics and treating qualified individuals.

As such, in one aspect, the present invention provides a method for qualifying Alzheimer's disease status in a subject, the method comprising: (a) measuring at least one biomarker in a biological sample from the subject, wherein the at least one biomarker is selected from the group consisting of the biomarkers of Table I, Table II, Table IV-A and Table IV-B, supra; and (b) correlating the measurement with Alzheimer's disease status. In one embodiment, the sample is cerebrospinal fluid (CSF). In another embodiment, the sample is serum. In a preferred embodiment, the at least one biomarker is selected from the group consisting of the biomarkers of Table II, Table IV-A and Table IV-B. In another preferred embodiment, the at least one biomarker is selected from the group consisting of the biomarkers of Table IV-B.

In a preferred embodiment, the at least one biomarker is selected from the biomarkers of Table II or Table IV-A or Table IV-B. In one embodiment, the at least one biomarker is selected from the following biomarkers: M60464.7 (Hemopexin), M3513.9 (7B2 CT fragment), M8291.0 (Ubiquitin-3aa from CT), M5044.2, M10379.8 (10.3 kDa), M9984.6 (related to 10.3 kDa), M10265.6 (related to 10.3 kDa), M9802.4 (EA-92 (ChrA peptide)), 9757.0 (related to 10.3 kDa), M16207.4 (Pancreatic ribonuclease), M14092.7 (Transthyretin S-glutathionylated), M13904.7 (Transthyretin S-Cys/S-CysGly), M12545.9 (Cystatin-C-8aa from NT), M8183.6 (Ubiquitin-4aa from CT), M5227.4, M3687.0 (Secretoneurin (ChrC/SGII peptide)), M3906.4 Vasostatin II (ChrA peptide), M3806.2, M8955.1, M5263.9, M14565.1 (Pancreatic ribonuclease), M20839.2, M6509.6 (Chromogranin B peptide), M4320.6 (A-beta 1-40), M7258.2 (Chromogranin B peptide), M17349.3 (Apolipoprotein A-II dimer), M58845.4, M8938.5 (C3a des-Arg), M6608.9, M5838.3, M23477.4 (Prostaglandin-D synthase), M4357.0 (Alpha-1-antichymotrypsin CT fragment), M7653.2 (Osteopontin CT fragment), M16716.9, M4812.5 (VGF(NCBI) peptide), M4989.4 (Thymosin beta-4-acetylated), M7878.7, M92082.4, M66479.2 (Albumin), M3967.6, M7718.8 (Osteopontin CT fragment phosphor), M89707.1, M11579.2, and M4455.4. In another preferred embodiment, the method comprises measuring N-acetylated thymosin beta-4. In yet another preferred embodiment, the at least one biomarker is selected from one of the biomarkers in Table II or IV-A or IV-B which is named in Table V.

In a preferred embodiment, the method comprises additionally measuring one or more of the following biomarkers: M11725.7 (Beta-2-Microglobulin), M78936.5 (transferrin), M13349.5 (Cystatin C), M66479.2 (Albumin) and M8585.9 (Ubiquitin), or alternatively, measuring each of these additional biomarkers. In another preferred embodiment, the method comprising measuring at least each of the biomarkers in the following two sets of biomarkers: M17349.3 (Apolipoprotein A-II dimer), M60464.7 (Hemopexin), and M3513.9 (7B2 CT fragment); and M17349.3 (Apolipoprotein A-II dimer), M60464.7 (Hemopexin), M10379.8 (10.3 kDa) and M11725.7 (Beta-2-Microglobulin). In another embodiment, the method comprising measuring at least one biomarker from the set consisting of the following biomarkers: 16207.4 (Pancreatic ribonuclease), 8183.6 (Ubiquitin-4aa from CT), M5227.4, M3806.2, M8955.1, M5263.9, M20839.2, M4320.6 (A-beta 1-40), 7258.2 (Chromogranin B peptide), M6608.9, M5838.3, M23477.4 ((Prostaglandin-D synthase), 7653.2 (Osteopontin CT fragment), M16716.9, M7878.7, 7718.8 (Osteopontin CT fragment phosphor), and M4455.4.

In one embodiment, the at least one biomarker is measured by capturing the biomarker on an adsorbent of a SELDI probe and detecting the captured biomarkers by laser desorption-ionization mass spectrometry. In certain embodiments, the adsorbent is a cation exchange adsorbent, an anion exchange adsorbent, a metal chelate or a hydrophobic adsorbent. In other embodiments, the adsorbent is a biospecific adsorbent. In another embodiment, the at least one biomarker is measured by immunoassay.

In another embodiment, the correlating is performed by a software classification algorithm. In certain embodiments, the Alzheimer's disease status is selected from Alzheimer's disease, non-dementia, and non-Alzheimer's dementia. In one embodiment, non-Alzheimer's dementia includes Lewy body dementia (LBD) and frontotemporal dementia (FTD).

In yet another embodiment, the method further comprises: (c) managing subject treatment based on the status. If the measurement correlates with Alzheimer's disease, then managing subject treatment comprises administering a choline esterase inhibitor to the subject.

In a further embodiment, the method further comprises: (d) measuring the at least one biomarker after subject management.

In another aspect, the present invention provides a method comprising measuring at least one biomarker in a sample from a subject, wherein the at least one biomarker is selected from the group consisting of the biomarkers set forth in Table I, II, IV-A, Table IV-B, or any of the groups of biomarkers discussed above. In one embodiment, the sample is cerebrospinal fluid (CSF). In another embodiment, the sample is serum. In a preferred embodiment, the at least one biomarker is selected from the group consisting of the biomarkers of Table II. In another preferred embodiment, the at least one biomarker is selected from the group consisting of the biomarkers of Table IV-A or Table IV-B. In another preferred embodiment, the method comprises measuring N-acetylated thymosin beta-4. In yet another preferred embodiment, the at least one biomarker is selected from one of the biomarkers in Table II, Table IV-A, or Table IV-B which is named in Table V.

In one embodiment, the at least one biomarker is selected from the following biomarkers: M60464.7 (Hemopexin), M3513.9 (7B2 CT fragment), M8291.0 (Ubiquitin-3aa from CT), M5044.2, M10379.8 (10.3 kDa), M9984.6 (related to 10.3 kDa), M10265.6 (related to 10.3 kDa), M9802.4 (EA-92 (ChrA peptide)), 9757.0 (related to 10.3 kDa), M16207.4 (Pancreatic ribonuclease), M14092.7 (Transthyretin S-glutathionylated), M13904.7 (Transthyretin S-Cys/S-CysGly), M12545.9 (Cystatin-C-8aa from NT), M8183.6 (Ubiquitin-4aa from CT), M5227.4, M3687.0 (Secretoneurin (ChrC/SGII peptide)), M3906.4 Vasostatin II (ChrA peptide), M3806.2, M8955.1, M5263.9, M14565.1 (Pancreatic ribonuclease), M20839.2, M6509.6 (Chromogranin B peptide), M4320.6 (A-beta 1-40), M7258.2 (Chromogranin B peptide), M17349.3 (Apolipoprotein A-II dimer), M58845.4, M8938.5 (C3a des-Arg), M6608.9, M5838.3, M23477.4 (Prostaglandin-D synthase), M4357.0 (Alpha-1-antichymotrypsin CT fragment), M7653.2 (Osteopontin CT fragment), M16716.9, M4812.5 (VGF(NCBI) peptide), M4989.4 (Thymosin beta-4-acetylated), M7878.7, M92082.4, M66479.2 (Albumin), M3967.6, M7718.8 (Osteopontin CT fragment phosphor), M89707.1, M11579.2, and M4455.4. In another embodiment, the at least one biomarker is selected from the following biomarkers: M11728.3 (β2 microglobulin), M60976.2 (Hemopexin), M11127.8 and M9742.3. In preferred embodiments, the method further comprises measuring Cystatin C (M13391). In yet another embodiment, the method further comprises additionally measuring a modified form of Cystatin C (CysC), for example, CysC Δ1-8, a truncated form of CysC missing 8 amino acids from the N-terminus of full-length CysC. In yet other embodiments, the method further comprises measuring at least one of the following additional biomarkers: M11725.7 (Beta-2-Microglobulin), M78936.5 (transferrin), M13349.5 (Cystatin C), M66479.2 (Albumin) and M8585.9 (Ubiquitin), or alternatively, measuring each of these additional biomarkers. In another preferred embodiment, the method comprises measuring N-acetylated thymosin beta-4. In yet another preferred embodiment, the at least one biomarker is selected from one of the biomarkers in Table II, Table IV-A, or Table IV-B which is named in Table V.

In one embodiment, the at least one biomarker is measured by capturing the biomarker on an adsorbent of a SELDI probe and detecting the captured biomarkers by laser desorption-ionization mass spectrometry. In certain embodiments, the adsorbent is a cation exchange adsorbent, an anion exchange adsorbent, a metal chelate or a hydrophobic adsorbent. In other embodiments, the adsorbent is a biospecific adsorbent. In another embodiment, the at least one biomarker is measured by immunoassay.

In still another aspect, the present invention provides a kit comprising: (a) a solid support comprising at least one capture reagent attached thereto, wherein the capture reagent binds at least one biomarker from a first group consisting of the biomarkers set forth in Table I, Table II, Table IV-A and Table IV-B; and (b) instructions for using the solid support to detect the at least one biomarker set forth in Table I, Table II, Table IV-A and Table IV-B. In a preferred embodiment, the at least one biomarker is selected from the group consisting of the biomarkers of Table II. In yet another preferred embodiment, the at least one biomarker is selected from one of the biomarkers in Table II, Table IV-A or Table IV-B which is named in Table V. In another preferred embodiment, the biomarker is N-acetylated thymosin beta-4.

In one embodiment, the kit provides instructions for using the solid support to detect a biomarker selected from the following biomarkers: M60464.7 (Hemopexin), M3513.9 (7B2 CT fragment), M8291.0 (Ubiquitin-3aa from CT), M5044.2, M10379.8 (10.3 kDa), M9984.6 (related to 10.3 kDa), M10265.6 (related to 10.3 kDa), M9802.4 (EA-92 (ChrA peptide)), 9757.0 (related to 10.3 kDa), M16207.4 (Pancreatic ribonuclease), M14092.7 (Transthyretin S-glutathionylated), M13904.7 (Transthyretin S-Cys/S-CysGly), M12545.9 (Cystatin-C-8aa from NT), M8183.6 (Ubiquitin-4aa from CT), M5227.4, M3687.0 (Secretoneurin (ChrC/SGII peptide)), M3906.4 Vasostatin II (ChrA peptide), M3806.2, M8955.1, M5263.9, M14565.1 (Pancreatic ribonuclease), M20839.2, M6509.6 (Chromogranin B peptide), M4320.6 (A-beta 1-40), M7258.2 (Chromogranin B peptide), M17349.3 (Apolipoprotein A-II dimer), M58845.4, M8938.5 (C3a des-Arg), M6608.9, M5838.3, M23477.4 (Prostaglandin-D synthase), M4357.0 (Alpha-1-antichymotrypsin CT fragment), M7653.2 (Osteopontin CT fragment), M16716.9, M4812.5 (VGF(NCBI) peptide), M4989.4 (Thymosin beta-4-acetylated), M7878.7, M92082.4, M66479.2 (Albumin), M3967.6, M7718.8 (Osteopontin CT fragment phosphor), M89707.1, M11579.2, and M4455.4. In another embodiment, the kit provides instructions for using the solid support to detect a biomarker selected from the following biomarkers: M11728.3 (β2 microglobulin), M60976.2 (Hemopexin), M11127.8 and M9742.3. In preferred embodiments, the kit further comprises instructions for using the solid support to detect Cystatin C (M13391). In yet other embodiments, the kit further comprises instructions for using the solid support to detect at least one of the following additional biomarkers: M11725.7 (Beta-2-Microglobulin), M78936.5 (transferrin), M13349.5 (Cystatin C), M66479.2 (Albumin) and M8585.9 (Ubiquitin), or, alternatively, additionally detecting each of these biomarkers. In yet other embodiments, the kit further comprises instructions for using the solid support to detect at least one of the biomarkers in Table II or IV which is named in Table V.

In another embodiment, the solid support comprising the capture reagent is a SELDI probe. In certain embodiments, the adsorbent is a cation exchange adsorbent, an anion exchange adsorbent, a metal chelate or a hydrophobic adsorbent. In some preferred embodiments, the capture reagent is a cation exchange adsorbent. In other embodiments, the kit additionally comprises (c) an anion exchange chromatography sorbent. In other embodiments, the kit additionally comprises (c) a container containing at least one of the biomarkers of Table I, Table II, Table IV-A or Table IV-B.

In a further aspect, the present invention provides a kit comprising: (a) a solid support comprising at least one capture reagent attached thereto, wherein the capture reagent binds at least one biomarker from a first group consisting of the biomarkers set forth in Table I, Table II, Table IV-A, or Table IV-B; and (b) a container comprising at least one of the biomarkers set forth in Table I, Table II, Table IV-A, or Table IV-B. In a preferred embodiment, the at least one biomarker is selected from the group consisting of the biomarkers of Table II, Table IV-A, and Table IV-B. In another preferred embodiment, the at least one biomarker is N-acetylated thymosin beta-4. In yet another preferred embodiment, the at least one biomarker is selected from one of the biomarkers in Table II or IV-A or V-B which is named in Table V.

In one embodiment, the kit provides instructions for using the solid support to detect a biomarker selected from the following biomarkers: M60464.7 (Hemopexin), M3513.9 (7B2 CT fragment), M8291.0 (Ubiquitin-3aa from CT), M5044.2, M10379.8 (10.3 kDa), M9984.6 (related to 10.3 kDa), M10265.6 (related to 10.3 kDa), M9802.4 (EA-92 (ChrA peptide)), 9757.0 (related to 10.3 kDa), M16207.4 (Pancreatic ribonuclease), M14092.7 (Transthyretin S-glutathionylated), M13904.7 (Transthyretin S-Cys/S-CysGly), M12545.9 (Cystatin-C-8aa from NT), M8183.6 (Ubiquitin-4aa from CT), M5227.4, M3687.0 (Secretoneurin (ChrC/SGII peptide)), M3906.4 Vasostatin II (ChrA peptide), M3806.2, M8955.1, M5263.9, M14565.1 (Pancreatic ribonuclease), M20839.2, M6509.6 (Chromogranin B peptide), M4320.6 (A-beta 1-40), M7258.2 (Chromogranin B peptide), M17349.3 (Apolipoprotein A-II dimer), M58845.4, M8938.5 (C3a des-Arg), M6608.9, M5838.3, M23477.4 (Prostaglandin-D synthase), M4357.0 (Alpha-1-antichymotrypsin CT fragment), M7653.2 (Osteopontin CT fragment), M16716.9, M4812.5 (VGF(NCBI) peptide), M4989.4 (Thymosin beta-4-acetylated), M7878.7, M92082.4, M66479.2 (Albumin), M3967.6, M7718.8 (Osteopontin CT fragment phosphor), M89707.1, M11579.2, and M4455.4. In preferred embodiments, the kit further comprises instructions for using the solid support to detect Cystatin C (M13391). In yet another embodiment, the kit provides instructions for additionally measuring one of the following biomarkers: In yet other embodiments, the kit further comprises instructions for using the solid support to detect at least one of the following additional biomarkers: M11725.7 (Beta-2-Microglobulin), M78936.5 (transferrin), M13349.5 (Cystatin C), M66479.2 (Albumin) and M8585.9 (Ubiquitin), or, alternatively, additionally detecting each of these biomarkers. In yet other embodiments, the kit further comprises instructions for using the solid support to detect at least one of the biomarkers in Table II or Table IV-A or Table IV-B which is named in Table V.

In another embodiment, the solid support comprising the capture reagent is a SELDI probe. In certain embodiments, the adsorbent is a cation exchange adsorbent, an anion exchange adsorbent, a metal chelate or a hydrophobic adsorbent. In other embodiments, the adsorbent is a biospecific adsorbent. In some embodiments, the capture reagent is a cation exchange adsorbent. In other embodiments, the kit additionally comprises (c) an anion exchange chromatography sorbent.

In yet a further aspect, the present invention provides a software product, the software product comprising: (a) code that accesses data attributed to a sample, the data comprising measurement of at least one biomarker in the sample, the biomarker selected from the group consisting of the biomarkers of Table I, Table II, Table IV-A, and Table IV-B; and (b) code that executes a classification algorithm that classifies the Alzheimer's disease status of the sample as a function of the measurement. In a preferred embodiment, the biomarker is selected from the group consisting of the biomarkers of Table IV-A or Table IV-B.

In one embodiment, the classification algorithm classifies Alzheimer's disease status of the sample as a function of the measurement of a biomarker selected from the group consisting of M60464.7 (Hemopexin), M3513.9 (7B2 CT fragment), M8291.0 (Ubiquitin-3aa from CT), M5044.2, M10379.8 (10.3 kDa), M9984.6 (related to 10.3 kDa), M10265.6 (related to 10.3 kDa), M9802.4 (EA-92 (ChrA peptide)), 9757.0 (related to 10.3 kDa), M16207.4 (Pancreatic ribonuclease), M14092.7 (Transthyretin S-glutathionylated), M13904.7 (Transthyretin S-Cys/S-CysGly), M12545.9 (Cystatin-C-8aa from NT), M8183.6 (Ubiquitin-4aa from CT), M5227.4, M3687.0 (Secretoneurin (ChrC/SGII peptide)), M3906.4 Vasostatin II (ChrA peptide), M3806.2, M8955.1, M5263.9, M14565.1 (Pancreatic ribonuclease), M20839.2, M6509.6 (Chromogranin B peptide), M4320.6 (A-beta 1-40), M7258.2 (Chromogranin B peptide), M17349.3 (Apolipoprotein A-II dimer), M58845.4, M8938.5 (C3a des-Arg), M6608.9, M5838.3, M23477.4 (Prostaglandin-D synthase), M4357.0 (Alpha-1-antichymotrypsin CT fragment), M7653.2 (Osteopontin CT fragment), M16716.9, M4812.5 (VGF(NCBI) peptide), M4989.4 (Thymosin beta-4-acetylated), M7878.7, M92082.4, M66479.2 (Albumin), M3967.6, M7718.8 (Osteopontin CT fragment phosphor), M89707.1, M11579.2, and M4455.4. In yet another embodiment, the classification algorithm classifies Alzheimer's disease status of the sample as a function of the additional measurement of the one of the following biomarkers: M11725.7 (Beta-2-Microglobulin), M78936.5 (transferrin), M13349.5 (Cystatin C), M66479.2 (Albumin) and M8585.9 (Ubiquitin). In yet other embodiments, the classification algorithm classifies Alzheimer's disease status of the sample as a function of the additional measurement of at least one of the biomarkers in Table II, Table IV-A or Table IV-B. In yet other embodiments, the classification algorithm classifies Alzheimer's disease status of the sample as a function of the additional measurement of at least one of the biomarkers in Table II, Table IV-A or Table IV-B which is named in Table V.

In other aspects, the present invention provides purified biomolecules selected from the biomarkers set forth in Table I, Table II, Table IV-A and Table IV-B, and additionally, methods comprising detecting a biomarker set forth in Table I, II, IV-A or Table IV-B by mass spectrometry or immunoassay.

Other features, objects and advantages of the invention and its preferred embodiments will become apparent from the detailed description, examples and claims that follow.

BRIEF DESCRIPTION OF THE DRAWINGS

FIG. 4A-K shows the distribution of peak intensities observed for the various groups and the results of Mann-Whitney or Kruskal-Wallis tests used to determine the significance of any differences observed.

FIG. 8 also shows the results of Mann-Whitney or Kruskal-Wallis tests used to determine the significance of any differences observed.

DETAILED DESCRIPTION OF THE INVENTION AND PREFERRED EMBODIMENTS

I. Introduction

Figure 1A:
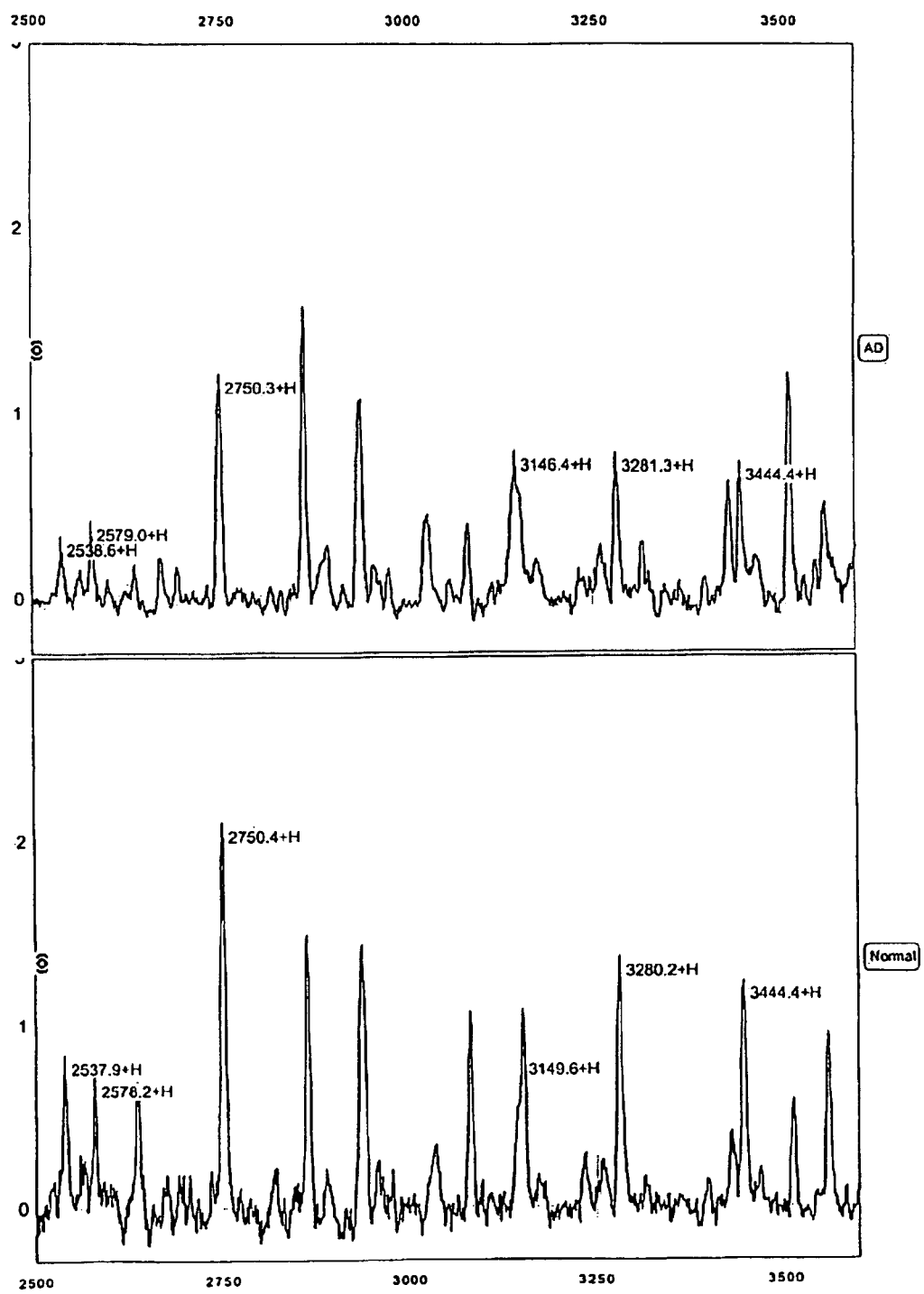
FIGS. 1A-1Q show mass spectra displaying biomarkers identified according to the techniques described in Example 1. The Figure also provides the mass-to-charge ratio for each biomarker.
Figure 1B:
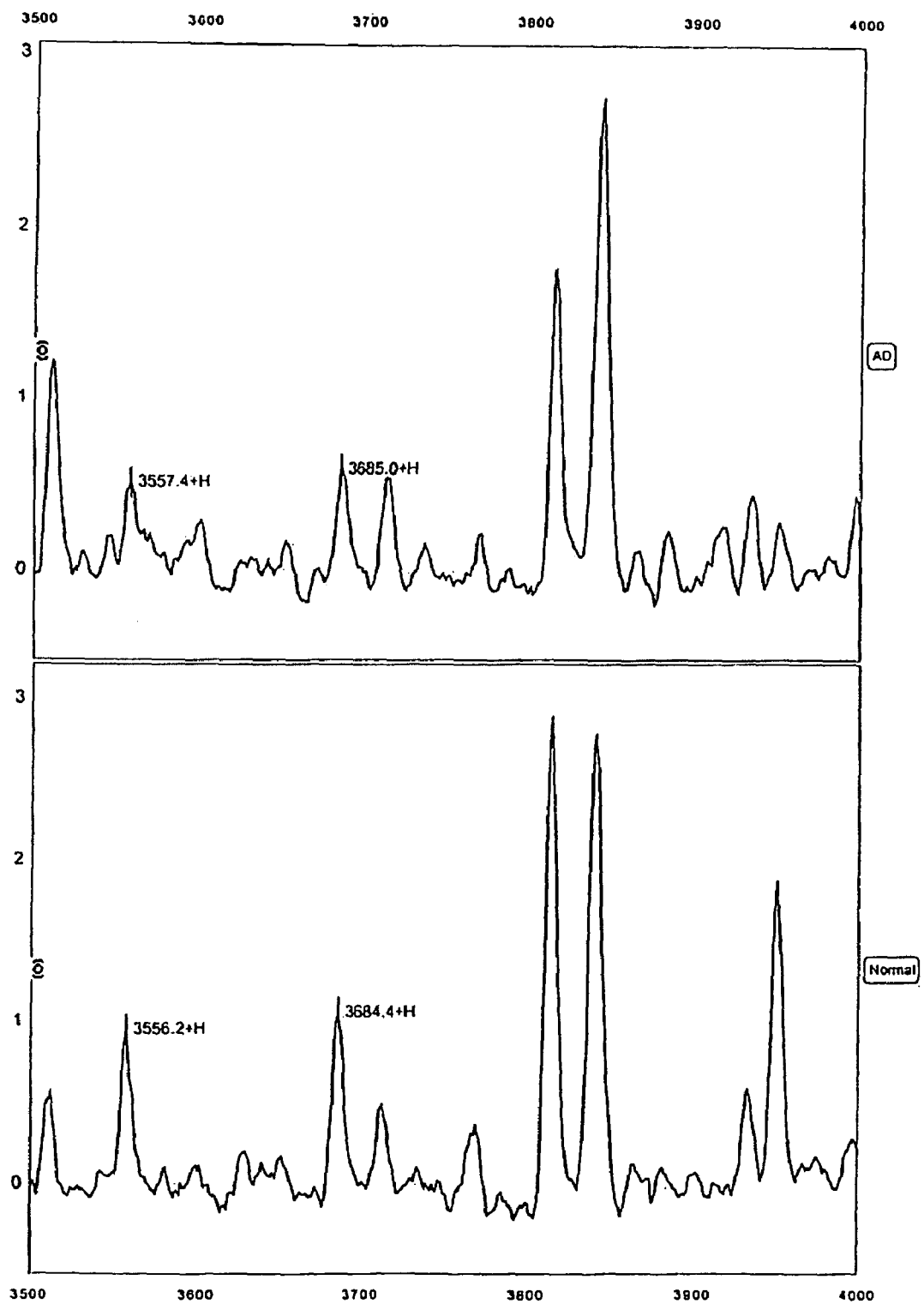
Figure 1C:
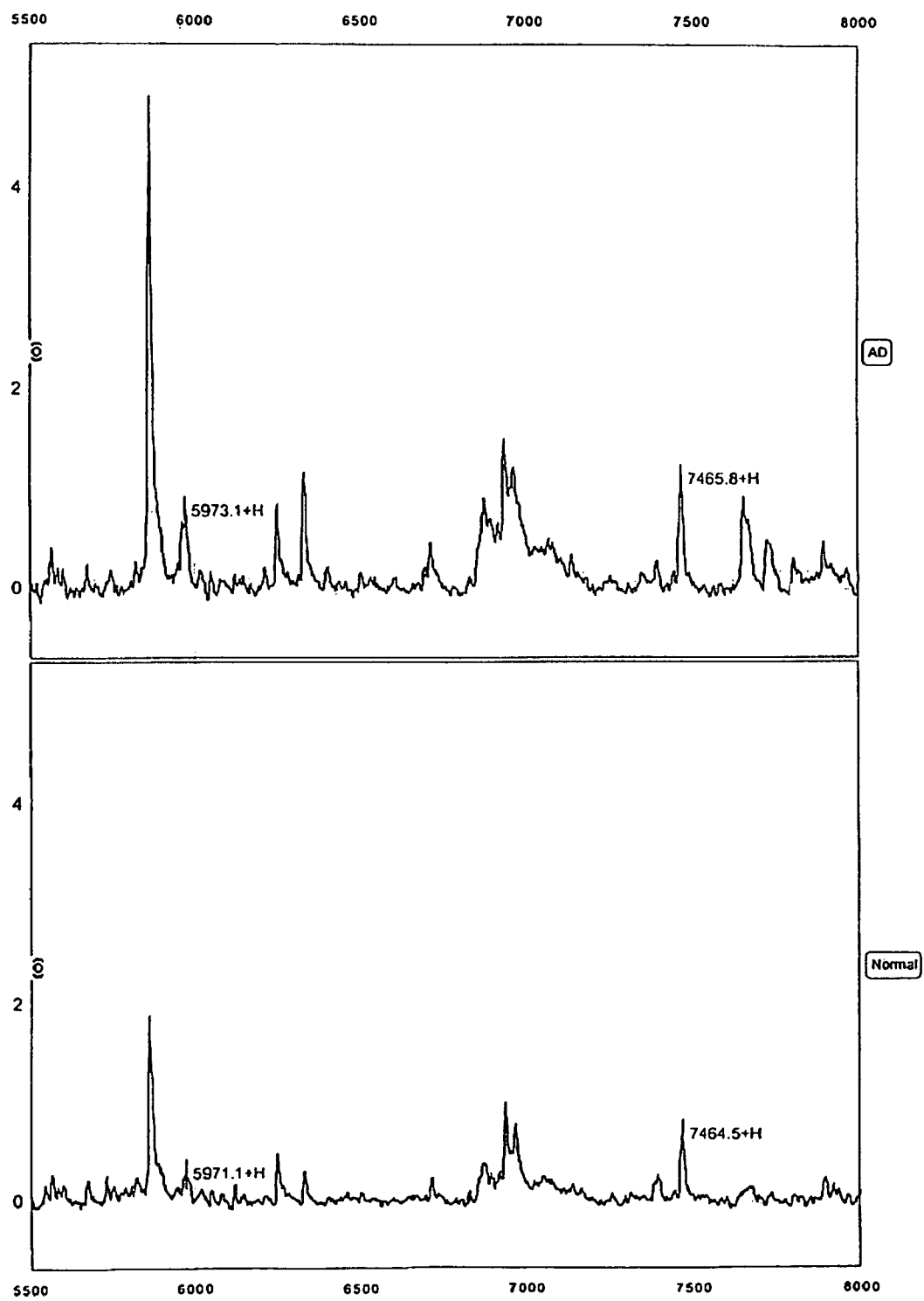
Figure 1D:
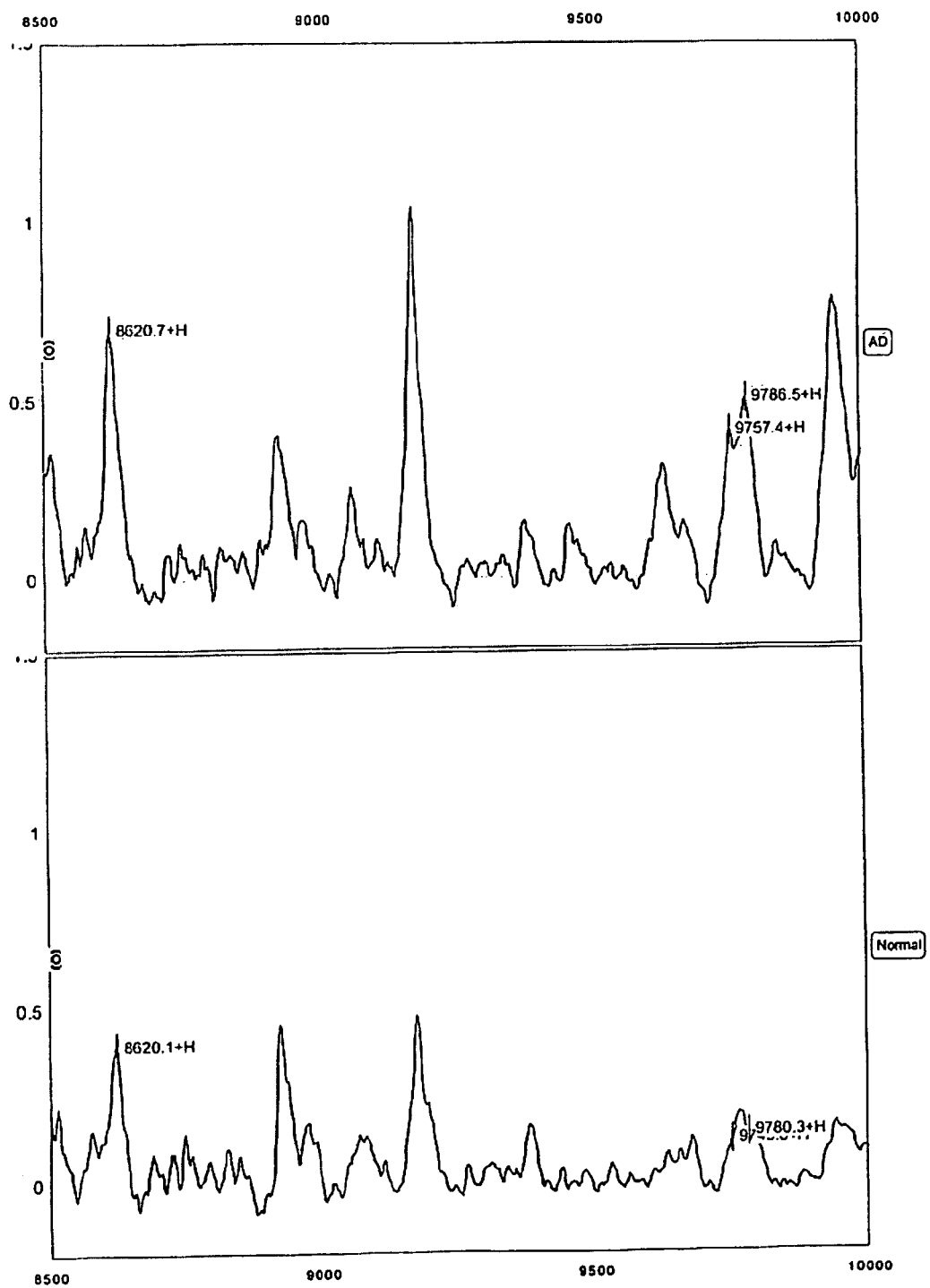
Figure 1E:
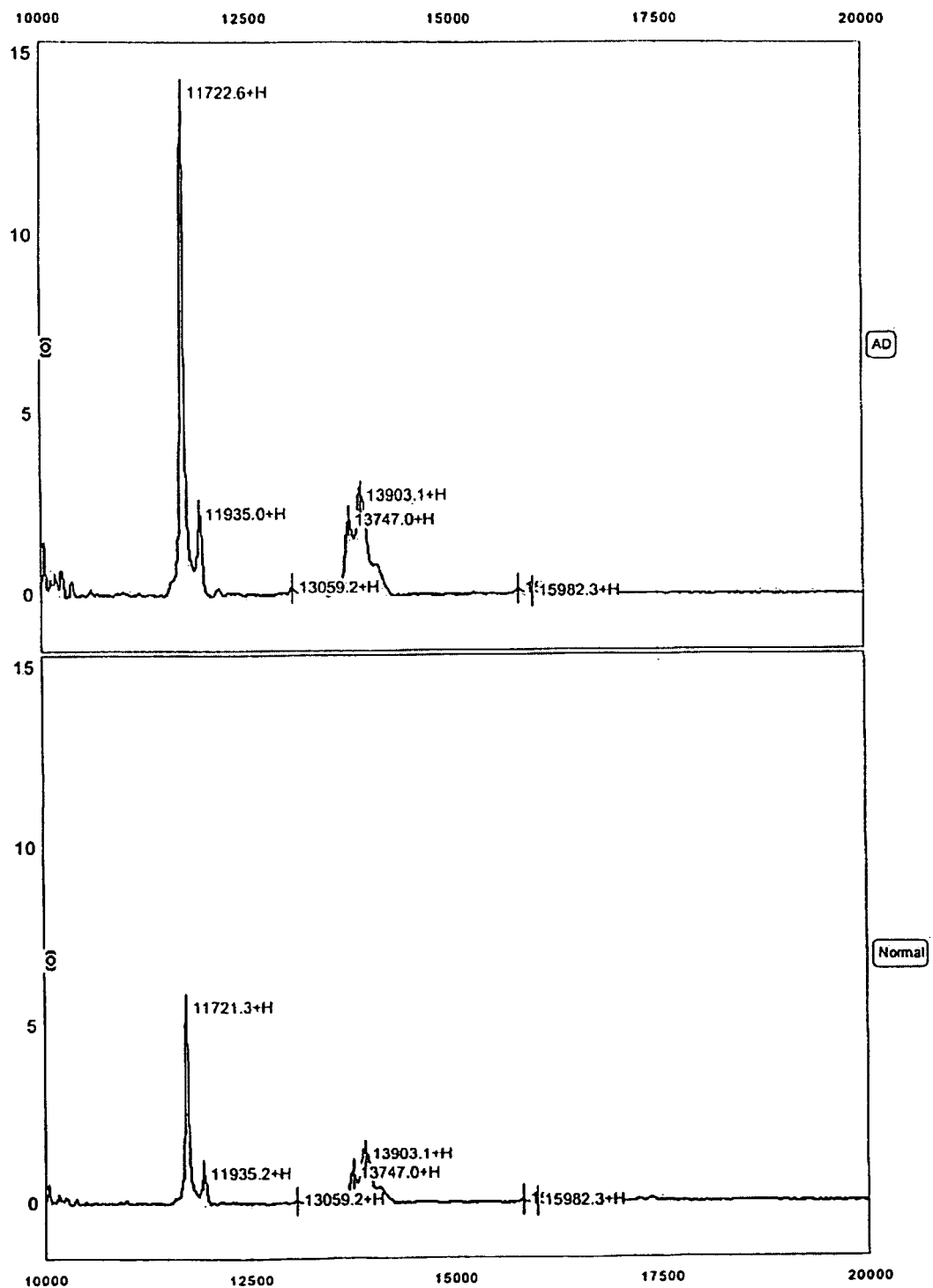
Figure 1F:
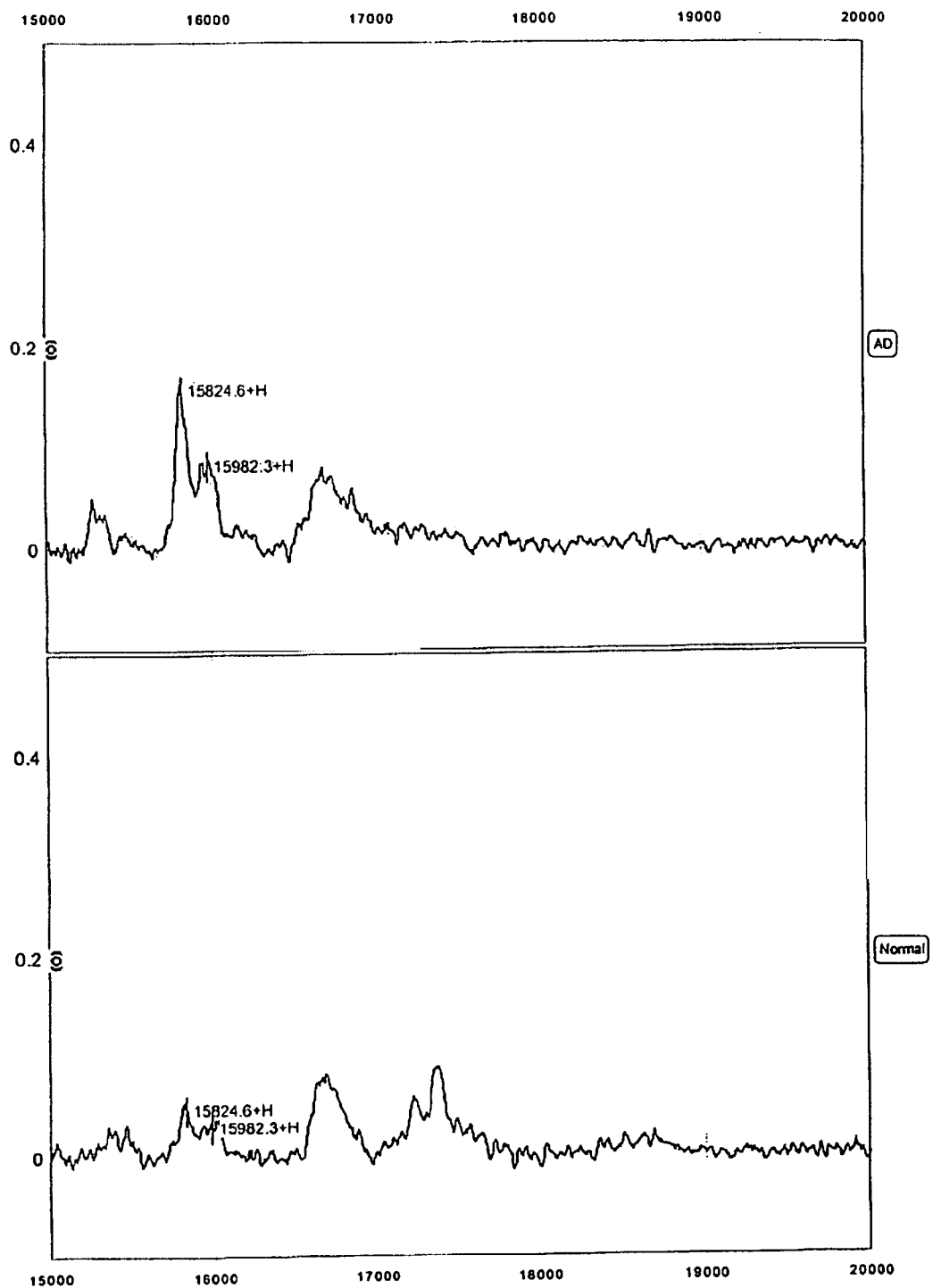
Figure 1G:
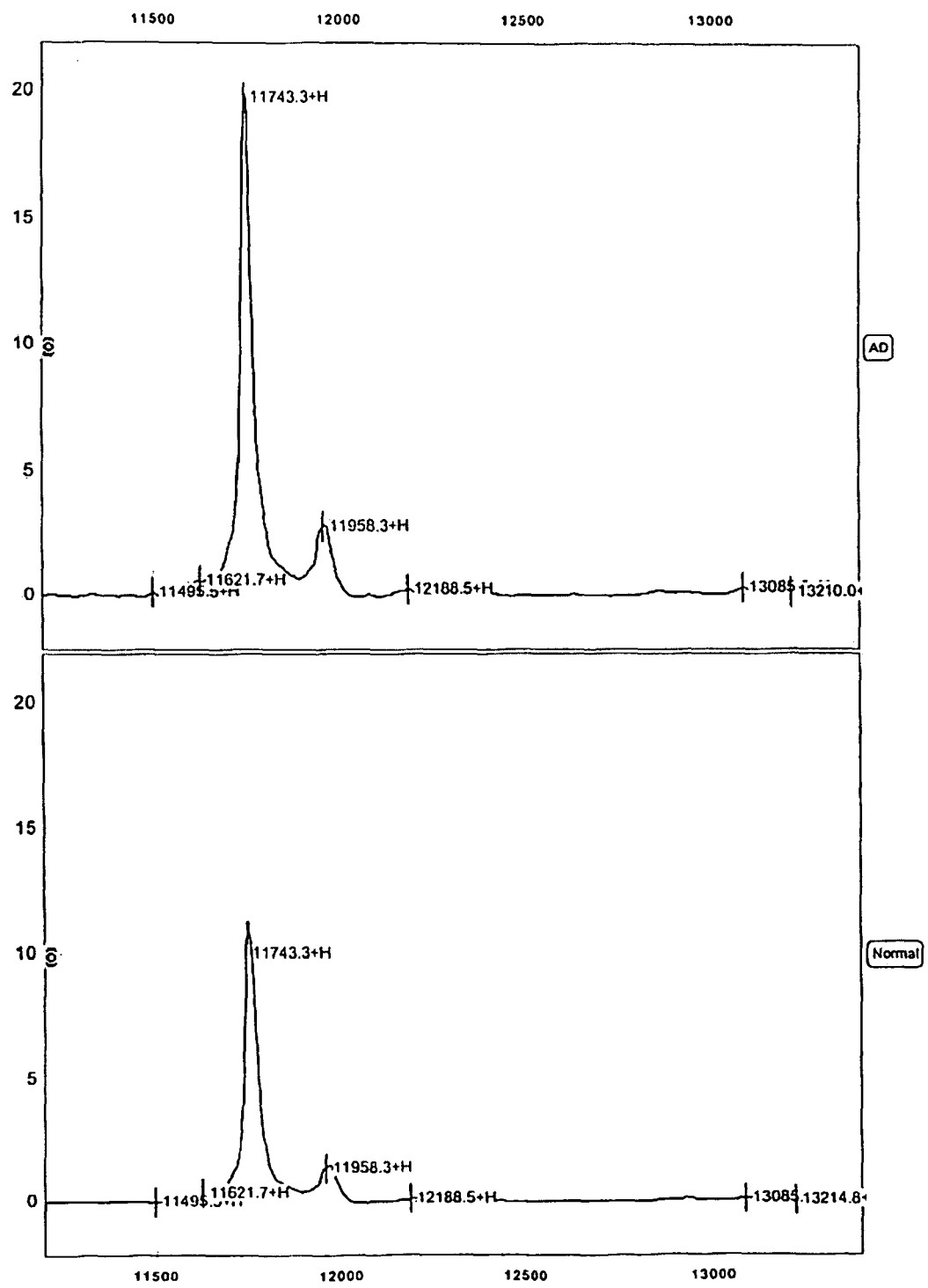
Figure 1H:
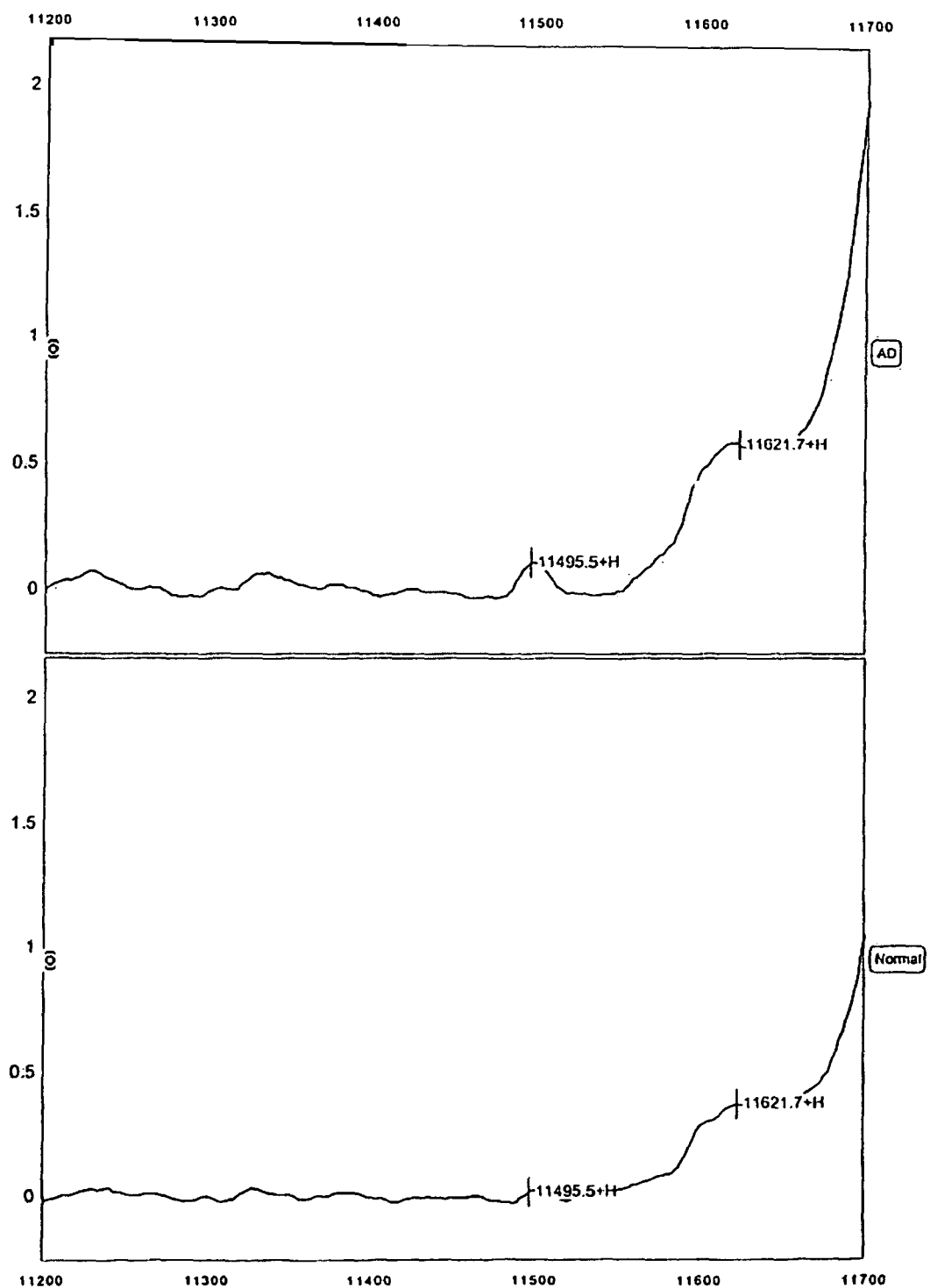
Figure 1I:
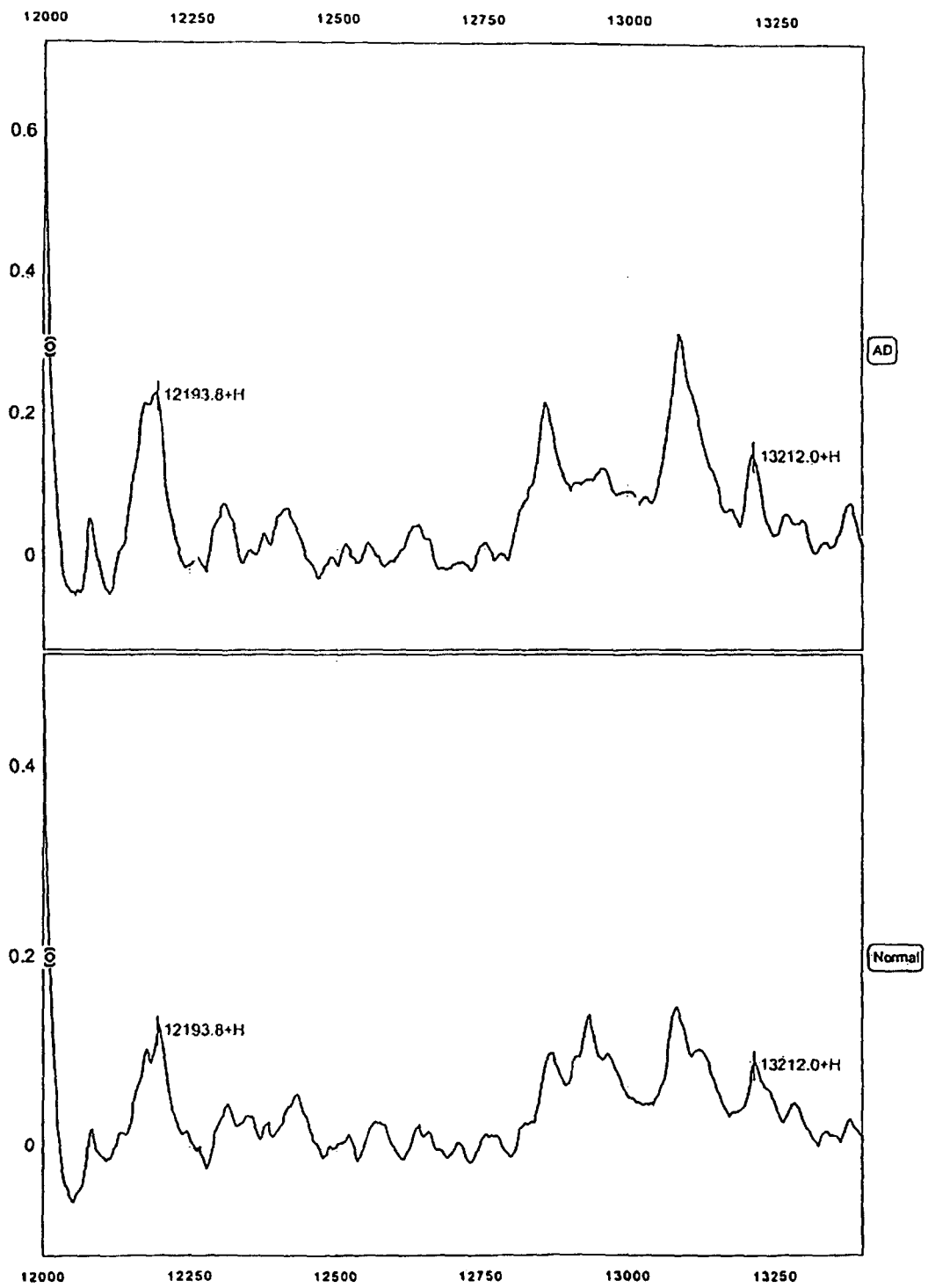
Figure 1J:
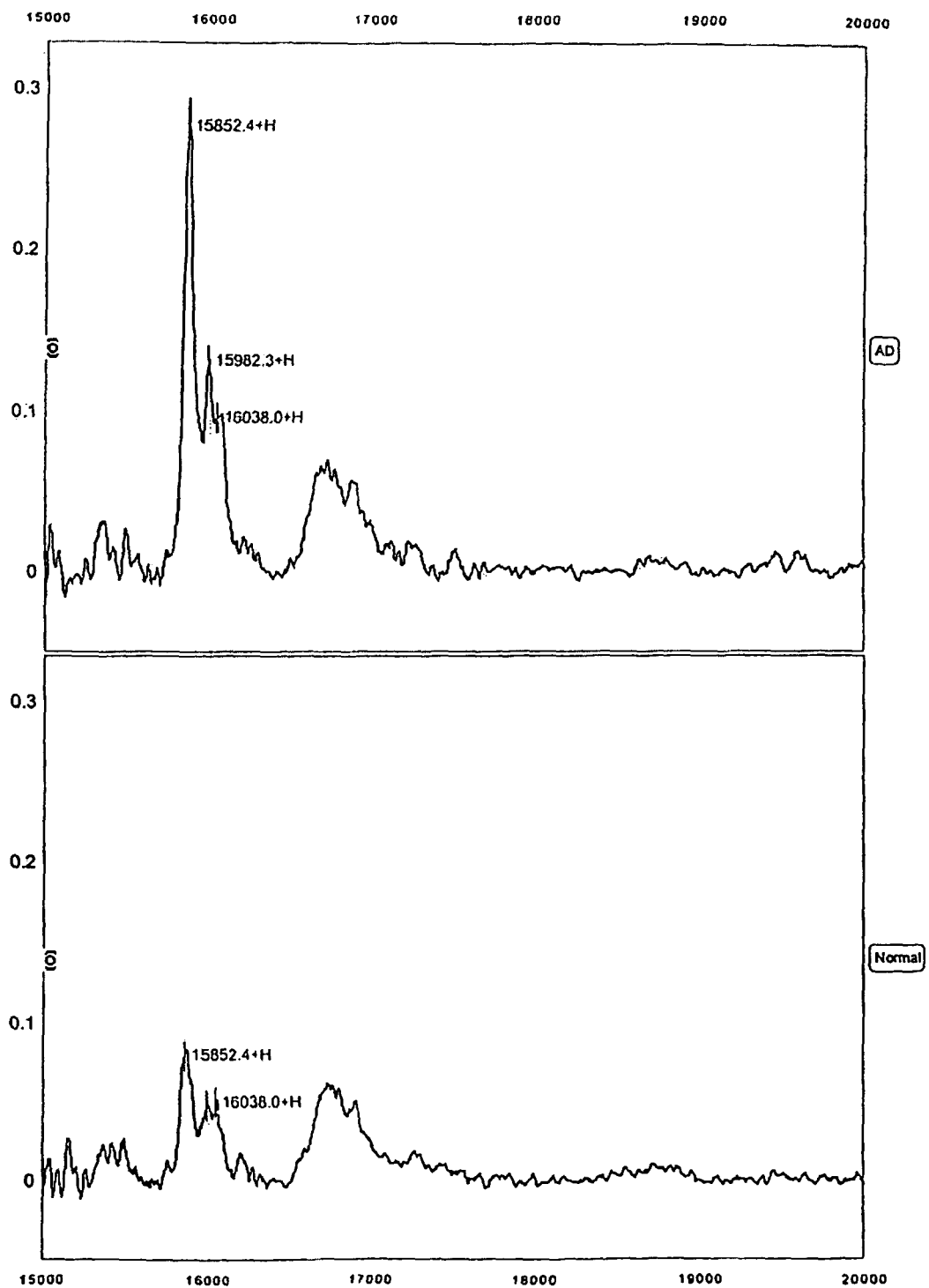
Figure 1K:
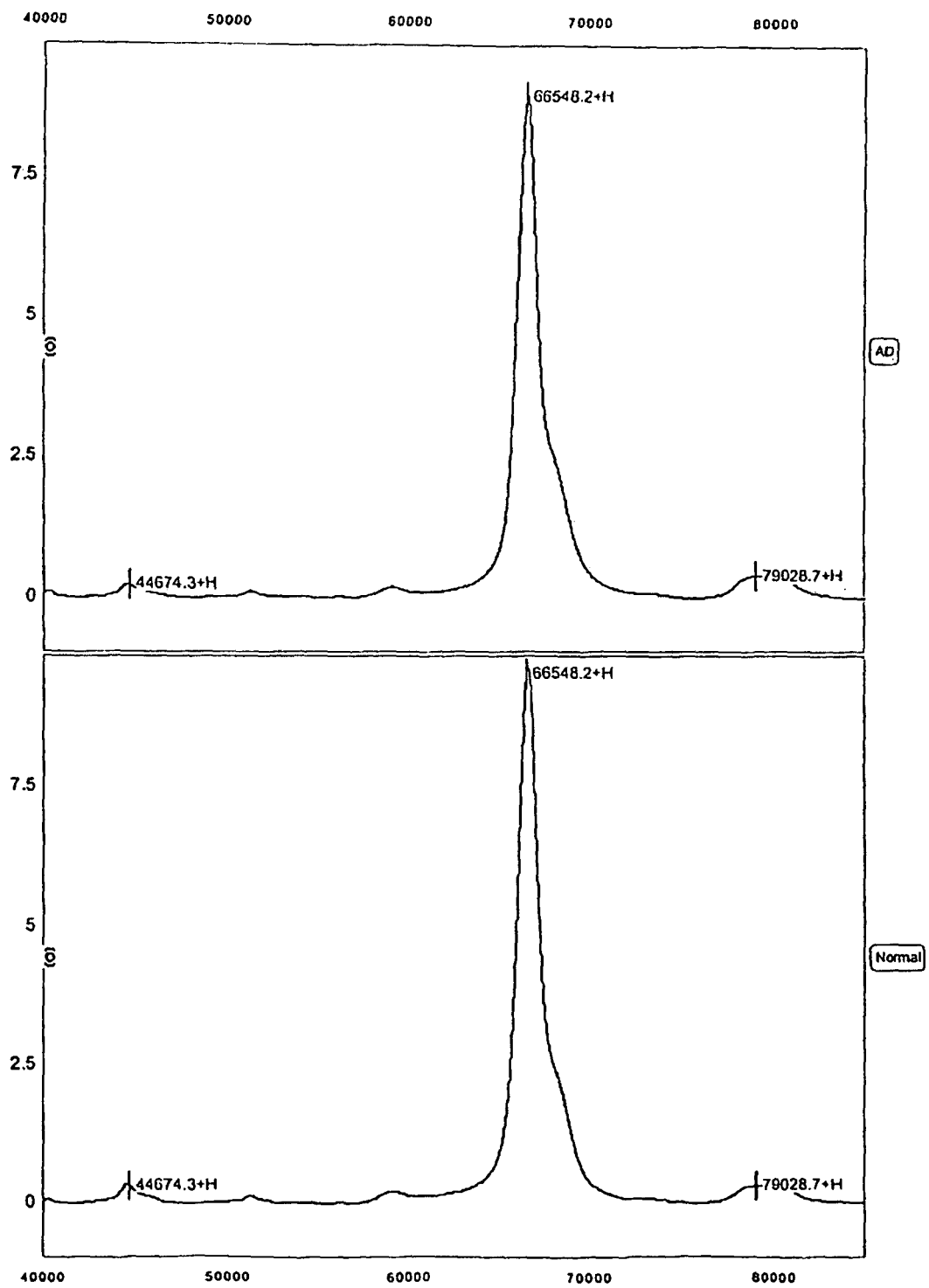
Figure 1L:
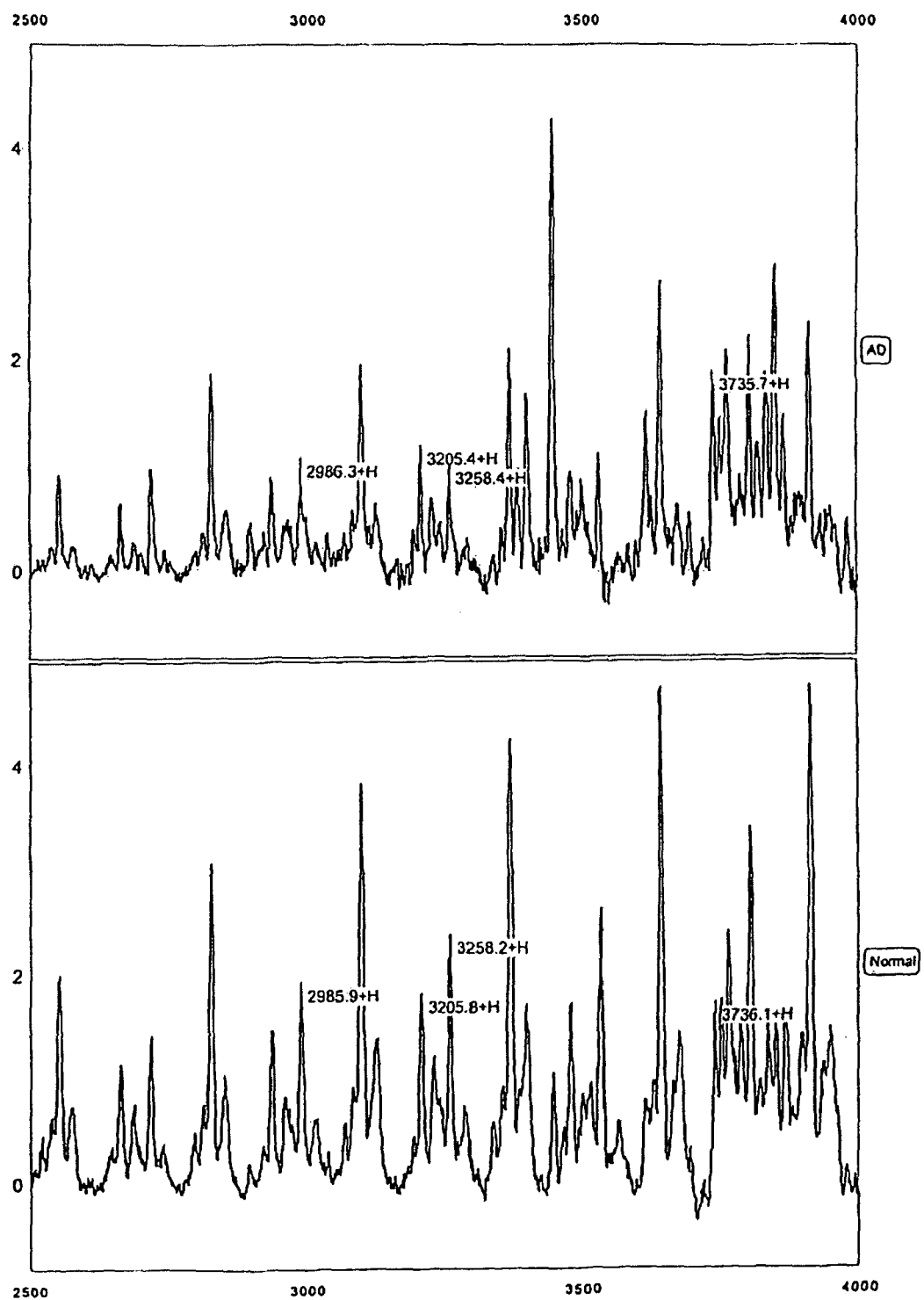
Figure 1M:
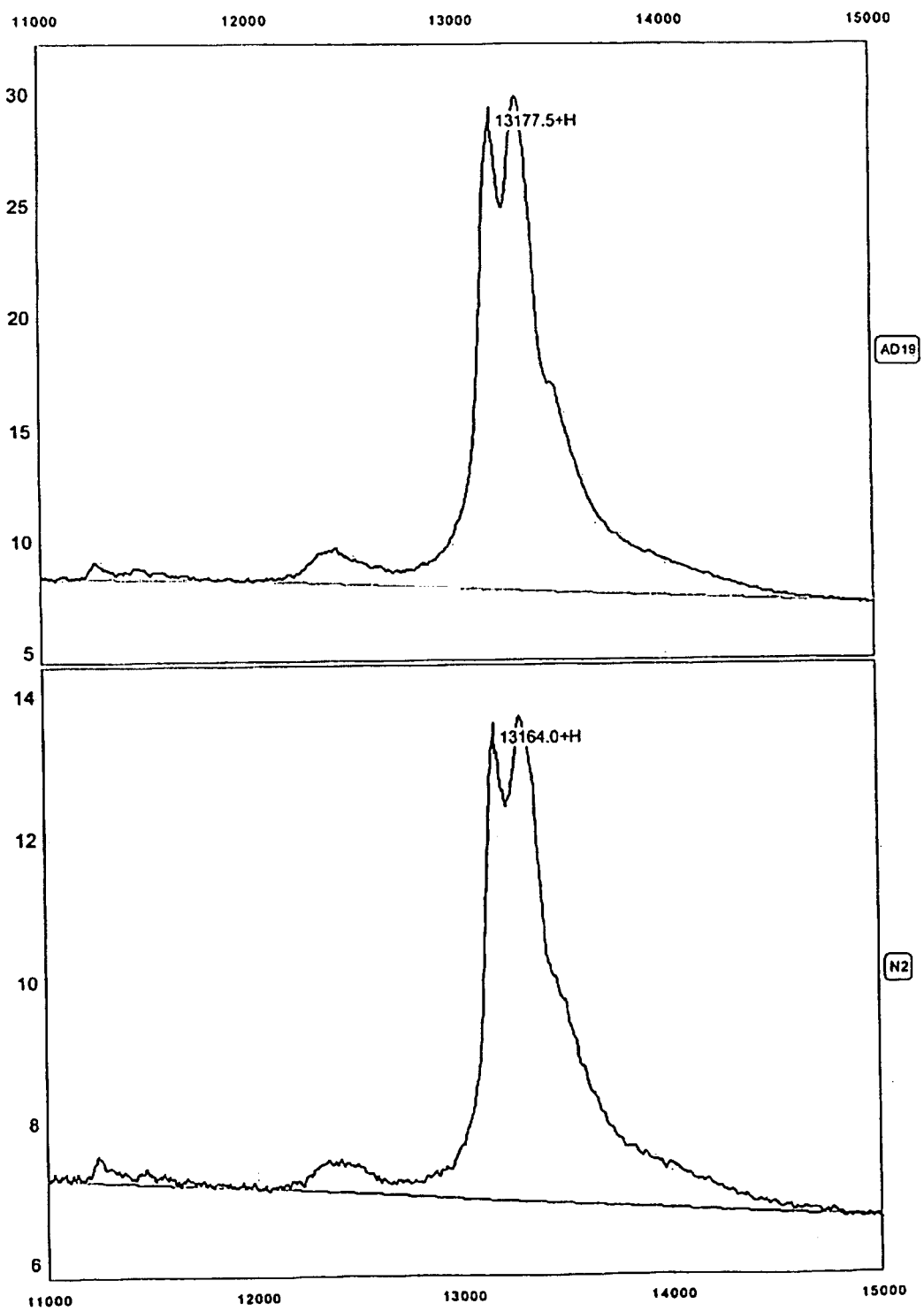
Figure 1N:
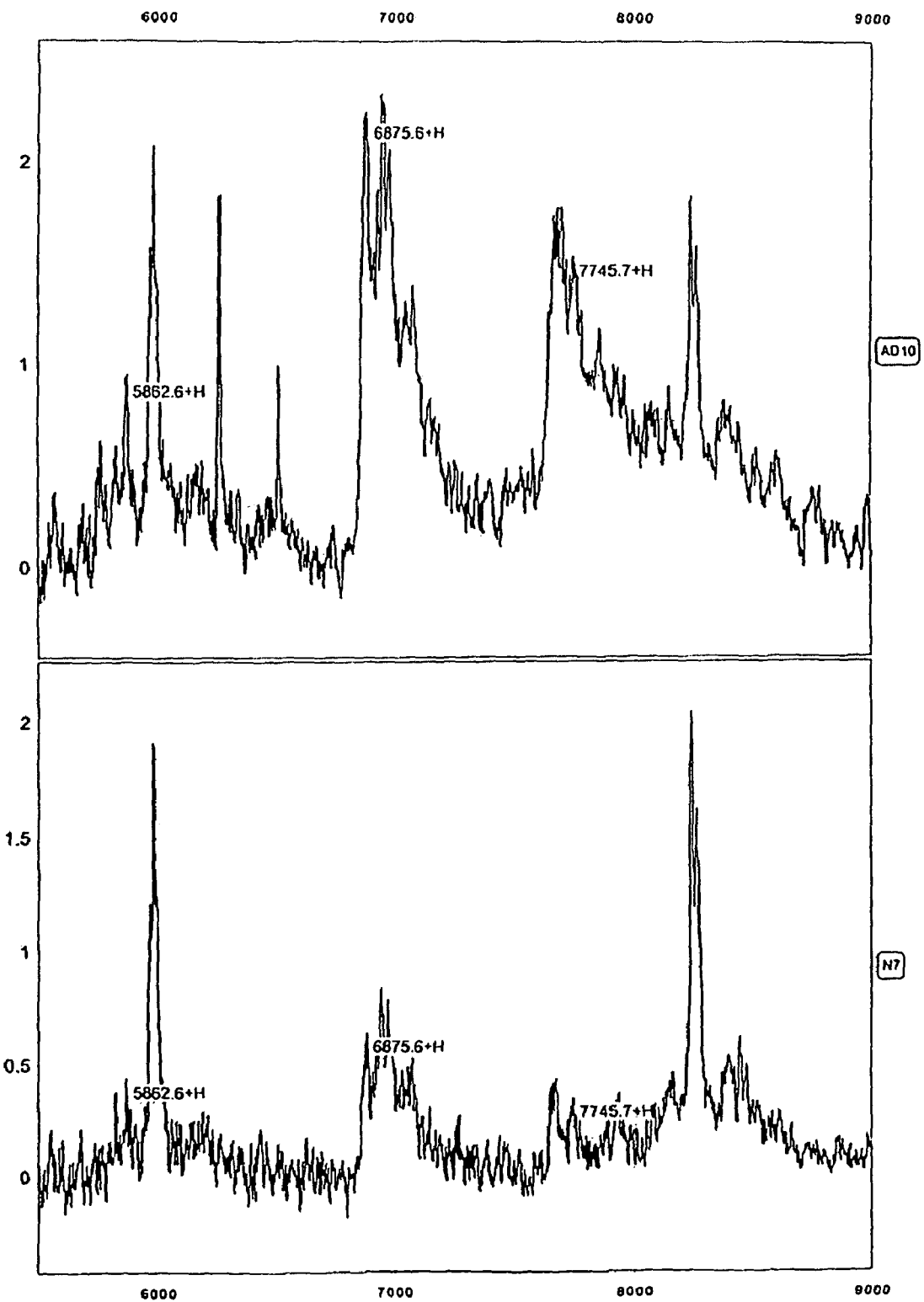

A biomarker is an organic biomolecule which is differentially present in a sample taken from a subject of one phenotypic status (e.g., having a disease) as compared with another phenotypic status (e.g., not having the disease). A biomarker is differentially present between different phenotypic statuses if the mean or median expression level of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, provide measures of relative risk that a subject belongs to one phenotypic status or another. Therefore, they are useful as markers for disease (diagnostics), therapeutic effectiveness of a drug (theranostics) and drug toxicity.

II. Biomarkers for Alzheimer's Disease

A. Biomarkers

This invention provides polypeptide-based biomarkers that are differentially present in subjects having Alzheimer's disease versus subjects free of the disease and/or versus subjects suffering from forms of non-Alzheimer's dementia (e.g., LB, FTD, etc.). In addition, the present invention provides methods of using the polypeptide-based biomarkers to qualify Alzheimer's disease in a subject. They are characterized by mass-to-charge ratio as determined by mass spectrometry, by the shape of their spectral peak in time-of-flight mass spectrometry and by their binding characteristics to adsorbent surfaces. These characteristics provide one method to determine whether a particular detected biomolecule is a biomarker of this invention. These characteristics represent inherent characteristics of the biomolecules and not process limitations in the manner in which the biomolecules are discriminated. In one aspect, this invention provides these biomarkers in isolated form.

The biomarkers were discovered using SELDI technology employing ProteinChip arrays from Ciphergen Biosystems, Inc. (Fremont, Calif.) ("Ciphergen"). CSF samples were collected from subjects diagnosed with Alzheimer's disease and subjects diagnosed as normal (non-demented). In some circumstances, CSF samples were fractionated by anion exchange chromatography (e.g., Example 1). Neat CSF samples may also be used (e.g., Example 3). Samples, either fractionated or neat, were applied to SELDI biochips and spectra of polypeptides in the samples were generated by time-of-flight mass spectrometry on a Ciphergen PBSII mass spectrometer. The spectra thus obtained were analyzed by Ciphergen Express™ Data Manager Software with Biomarker Wizard and Biomarker Pattern Software from Ciphergen Biosystems, Inc. The mass spectra for each group were subjected to scatter plot analysis. A Mann-Whitney test analysis was employed to compare Alzheimer's disease and control groups for each protein cluster in the scatter plot, and proteins were selected that differed significantly (p<0.0001) between the two groups. This method is described in more detail in the Example Section.

Examples of the discovered biomarkers for qualifying Alzheimer's disease are presented in Tables I, II, IV-A, IV-B and V. The "ProteinChip assay" column refers to chromatographic fraction in which the biomarker is found, the type of biochip to which the biomarker binds and the wash conditions, as described in detail in the Examples herein.

The biomarkers of this invention are characterized by their mass-to-charge ratio as determined by mass spectrometry. The mass-to-charge ratio of each biomarker is provided in the Tables herein. In Table I, for example, the biomarker masses are provided after the "M." Thus, for example, biomarker M2579.3 has a measured mass-to-charge ratio of 2579.3. The mass-to-charge ratios were determined from mass spectra generated on a Ciphergen Biosystems, Inc. PBS II mass spectrometer. This instrument has a mass accuracy of about +/−0.15 percent (e.g., for a 5,000 Da protein, the error is ±7.5 Da). Thus, the biomarkers herein which are referred to by a measured apparent mass are not expected to provide precisely the same apparent weight every time their presence is detected in a given sample. Additionally, the PBS II mass spectrometer has a mass resolution of about 400 to 1000 m/dm, where m is mass and dm is the mass spectral peak width at 0.5 peak height. The mass-to-charge ratio of the biomarkers was determined using Biomarker Wizard™ software (Ciphergen Biosystems, Inc.). Biomarker Wizard assigns a mass-to-charge ratio to a biomarker by clustering the mass-to-charge ratios of the same peaks from all the spectra analyzed, as determined by the PBSII, taking the maximum and minimum mass-to-charge-ratio in the cluster, and dividing by two. Accordingly, the masses provided reflect these specifications.

The biomarkers of this invention are further characterized by the shape of their spectral peak in time-of-flight mass spectrometry. Mass spectra showing peaks representing many of the biomarkers are presented in FIGS. 1 and 9.

The biomarkers of this invention are further characterized by their binding properties on chromatographic surfaces. The biomarkers of the present invention bind to cation exchange adsorbents (preferably a CM-10 or WCX-2 ProteinChip array (Ciphergen Biosystems, Inc.)), anion exchange adsorbents (preferably a Q-10 ProteinChip array (Ciphergen Biosystems, Inc.)), hydrophobic exchange adsorbents (preferably a H50 ProteinChip array (Ciphergen Biosystems, Inc.)) and/or IMAC adsorbents (preferably an IMAC 3 or IMAC30 ProteinChip array (Ciphergen Biosystems, Inc.)).

The identities of many of the biomarkers of this invention have been determined and are indicated in the Tables herein. Methods by which these determination were made are also provided, e.g., in the Example Section. For biomarkers whose identify has been determined, the presence of the biomarker can be determined by other methods known in the art, for example, by immunoassay, enzymatic activity assay, or by measuring any other detectable property of the biomarker.

Because the biomarkers of this invention are characterized by mass-to-charge ratio, binding properties and spectral shape, they can be detected by mass spectrometry without knowing their specific identity. However, if desired, biomarkers whose identity is not determined can be identified by, for example, determining the amino acid sequence of the polypeptides. For example, a biomarker can be peptide-mapped with a number of enzymes, such as trypsin or V8 protease, and the molecular weights of the digestion fragments can be used to search databases for sequences that match the molecular weights of the digestion fragments generated by the various enzymes. Alternatively, protein biomarkers can be sequenced using tandem MS technology. In this method, the protein is isolated by, for example, gel electrophoresis. A band containing the biomarker is cut out and the protein is subject to protease digestion. Individual protein fragments are separated by a first mass spectrometer. The fragment is then subjected to collision-induced cooling, which fragments the peptide and produces a polypeptide ladder. A polypeptide ladder is then analyzed by the second mass spectrometer of the tandem MS. The difference in masses of the members of the polypeptide ladder identifies the amino acids in the sequence. An entire protein can be sequenced this way, or a sequence fragment can be subjected to database mining to find identity candidates.

The preferred biological source for detection of the biomarkers is cerebrospinal fluid ("CSF"). However, in other embodiments, the biomarkers can be detected in serum. Many of the biomarkers of the present invention can be found in both CSF and serum. For instance, it has been discovered that Alzheimer's disease biomarkers Beta-2-microglobulin and Cystatin C (both full-length and variant forms) are found in both CSF and serum.

The biomarkers of this invention are biomolecules. Accordingly, this invention provides these biomolecules in isolated form. The biomarkers can be isolated from biological fluids, such as CSF or serum. They can be isolated by any method known in the art, based on both their mass and their binding characteristics. For example, a sample comprising the biomolecules can be subject to chromatographic fractionation, as described herein, and subject to further separation by, e.g., acrylamide gel electrophoresis. Knowledge of the identity of the biomarker also allows their isolation by immunoaffinity chromatography.

B. Use of Modified Forms of a Biomarker

It has been found that proteins frequently exist in a sample in a plurality of different forms characterized by a detectably different mass. These forms can result from either, or both, of pre- and post-translational modification. Pre-translational modified forms include allelic variants, slice variants and RNA editing forms. Post-translationally modified forms include forms resulting from proteolytic cleavage (e.g., fragments of a parent protein), glycosylation, phosphorylation, lipidation, oxidation, methylation, cystinylation, sulphonation and acetylation. The collection of proteins including a specific protein and all modified forms of it is referred to herein as a "protein cluster." The collection of all modified forms of a specific protein, excluding the specific protein, itself, is referred to herein as a "modified protein cluster."

Modified forms of any biomarker of this invention (including those set forth in Tables I, II, V-A, IV-B or V) also may be used, themselves, as biomarkers. In certain cases, the modified forms may exhibit better discriminatory power in diagnosis than the unmodified form of the protein.

Modified forms of a biomarker including any of those set forth in Tables, including those set forth in Tables I, II, IV-A, IV-B or V, can be initially detected by any methodology that can detect and distinguish the modified form from the biomarker. A preferred method for initial detection involves first capturing the biomarker and modified forms of it, e.g., with biospecific capture reagents, and then detecting the captured proteins by mass spectrometry. More specifically, the proteins are captured using biospecific capture reagents, such as antibodies, aptamers or Affibodies that recognize the biomarker and modified forms of it. This method will also result in the capture of protein interactors that are bound to the proteins or that are otherwise recognized by antibodies and that, themselves, can be biomarkers. Preferably, the biospecific capture reagents are bound to a solid phase. Then, the captured proteins can be detected by SELDI mass spectrometry or by eluting the proteins from the capture reagent and detecting the eluted proteins by traditional MALDI or by SELDI. The use of mass spectrometry is especially attractive because it can distinguish and quantify modified forms of a protein based on mass and without the need for labeling.

Preferably, the biospecific capture reagent is bound to a solid phase, such as a bead, a plate, a membrane or a chip. Methods of coupling biomolecules, such as antibodies, to a solid phase are well known in the art. They can employ, for example, bifunctional linking agents, or the solid phase can be derivatized with a reactive group, such as an epoxide or an imidizole, that will bind the molecule on contact. Biospecific capture reagents against different target proteins can be mixed in the same place, or they can be attached to solid phases in different physical or addressable locations. For example, one can load multiple columns with derivatized beads, each column able to capture a single protein cluster. Alternatively, one can pack a single column with different beads derivatized with capture reagents against a variety of protein clusters, thereby capturing all the analytes in a single place. Accordingly, antibody-derivatized bead-based technologies, such as xMAP technology of Luminex (Austin, Tex.) can be used to detect the protein clusters. However, the biospecific capture reagents must be specifically directed toward the members of a cluster in order to differentiate them.

In yet another embodiment, the surfaces of biochips can be derivatized with the capture reagents directed against protein clusters either in the same location or in physically different addressable locations. One advantage of capturing different clusters in different addressable locations is that the analysis becomes simpler.

After identification of modified forms of a protein and correlation with the clinical parameter of interest, the modified form can be used as a biomarker in any of the methods of this invention. At this point, detection of the modified from can be accomplished by any specific detection methodology including affinity capture followed by mass spectrometry, or traditional immunoassay directed specifically the modified form. Immunoassay requires biospecific capture reagents, such as antibodies, to capture the analytes. Furthermore, if the assay must be designed to specifically distinguish protein and modified forms of protein. This can be done, for example, by employing a sandwich assay in which one antibody captures more than one form and second, distinctly labeled antibodies, specifically bind, and provide distinct detection of, the various forms. Antibodies can be produced by immunizing animals with the biomolecules. This invention contemplates traditional immunoassays including, for example, sandwich immunoassays including ELISA or fluorescence-based immunoassays, as well as other enzyme immunoassays.

III. Detection of Biomarkers for Alzheimer's Disease

The biomarkers of this invention can be detected by any suitable method. Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

In one embodiment, a sample is analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

"Protein biochip" refers to a biochip adapted for the capture of polypeptides. Many protein biochips are described in the art. These include, for example, protein biochips produced by Ciphergen Biosystems, Inc. (Fremont, Calif.), Packard BioScience Company (Meriden Conn.), Zyomyx (Hayward, Calif.), Phylos (Lexington, Mass.) and Biacore (Uppsala, Sweden). Examples of such protein biochips are described in the following patents or published patent applications: U.S. Pat. No. 6,225,047; PCT International Publication No. WO 99/51773; U.S. Pat. No. 6,329,209, PCT International Publication No. WO 00/56934 and U.S. Pat. No. 5,242,828.

A. Detection by Mass Spectrometry

In a preferred embodiment, the biomarkers of this invention are detected by mass spectrometry, a method that employs a mass spectrometer to detect gas phase ions. Examples of mass spectrometers are time-of-flight, magnetic sector, quadrupole filter, ion trap, ion cyclotron resonance, electrostatic sector analyzer and hybrids of these.

In a further preferred method, the mass spectrometer is a laser desorption/ionization mass spectrometer. In laser desorption/ionization mass spectrometry, the analytes are placed on the surface of a mass spectrometry probe, a device adapted to engage a probe interface of the mass spectrometer and to present an analyte to ionizing energy for ionization and introduction into a mass spectrometer. A laser desorption mass spectrometer employs laser energy, typically from an ultraviolet laser, but also from an infrared laser, to desorb analytes from a surface, to volatilize and ionize them and make them available to the ion optics of the mass spectrometer.

1. SELDI

A preferred mass spectrometric technique for use in the invention is "Surface Enhanced Laser Desorption and Ionization" or "SELDI," as described, for example, in U.S. Pat. No. 5,719,060 and U.S. Pat. No. 6,225,047, both to Hutchens and Yip. This refers to a method of desorption/ionization gas phase ion spectrometry (e.g., mass spectrometry) in which an analyte (here, one or more of the biomarkers) is captured on the surface of a SELDI mass spectrometry probe. There are several versions of SELDI.

One version of SELDI is called "affinity capture mass spectrometry." It also is called "Surface-Enhanced Affinity Capture" or "SEAC". This version involves the use of probes that have a material on the probe surface that captures analytes through a non-covalent affinity interaction (adsorption) between the material and the analyte. The material is variously called an "adsorbent," a "capture reagent," an "affinity reagent" or a "binding moiety." Such probes can be referred to as "affinity capture probes" and as having an "adsorbent surface." The capture reagent can be any material capable of binding an analyte. The capture reagent may be attached directly to the substrate of the selective surface, or the substrate may have a reactive surface that carries a reactive moiety that is capable of binding the capture reagent, e.g., through a reaction forming a covalent or coordinate covalent bond. Epoxide and carbodiimidizole are useful reactive moieties to covalently bind polypeptide capture reagents such as antibodies or cellular receptors. Nitriloacetic acid and iminodiacetic acid are useful reactive moieties that function as chelating agents to bind metal ions that interact non-covalently with histidine containing peptides. Adsorbents are generally classified as chromatographic adsorbents and biospecific adsorbents.

"Chromatographic adsorbent" refers to an adsorbent material typically used in chromatography. Chromatographic adsorbents include, for example, ion exchange materials, metal chelators (e.g., nitriloacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents).

"Biospecific adsorbent" refers to an adsorbent comprising a biomolecule, e.g., a nucleic acid molecule (e.g., an aptamer), a polypeptide, a polysaccharide, a lipid, a steroid or a conjugate of these (e.g., a glycoprotein, a lipoprotein, a glycolipid, a nucleic acid (e.g., DNA)-protein conjugate). In certain instances, the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target analyte than chromatographic adsorbents. Further examples of adsorbents for use in SELDI can be found in U.S. Pat. No. 6,225,047. A "bioselective adsorbent" refers to an adsorbent that binds to an analyte with an affinity of at least $10^{-8}$ M.

Protein biochips produced by Ciphergen Biosystems, Inc. comprise surfaces having chromatographic or biospecific adsorbents attached thereto at addressable locations. Ciphergen ProteinChip® arrays include NP20 (hydrophilic); H4 and H50 (hydrophobic); SAX-2, Q-10 and LSAX-30 (anion exchange); WCX-2, CM-10 and LWCX-30 (cation exchange); IMAC-3, IMAC-30 and IMAC 40 (metal chelate); and PS-10, PS-20 (reactive surface with carboimidizole, expoxide) and PG-20 (protein G coupled through carboimidizole). Hydrophobic ProteinChip arrays have isopropyl or nonylphenoxy-poly(ethylene glycol)methacrylate functionalities. Anion exchange ProteinChip arrays have quaternary ammonium functionalities. Cation exchange ProteinChip arrays have carboxylate functionalities. Immobilized metal chelate ProteinChip arrays have have nitriloacetic acid functionalities that adsorb transition metal ions, such as copper, nickel, zinc, and gallium, by chelation. Preactivated ProteinChip arrays have carboimidizole or epoxide functional groups that can react with groups on proteins for covalent binding.

Such biochips are further described in: U.S. Pat. No. 6,579,719 (Hutchens and Yip, "Retentate Chromatography," Jun. 17, 2003); PCT International Publication No. WO 00/66265 (Rich et al., "Probes for a Gas Phase Ion Spectrometer," Nov. 9, 2000); U.S. Pat. No. 6,555,813 (Beecher et al., "Sample Holder with Hydrophobic Coating for Gas Phase Mass Spectrometer," Apr. 29, 2003); U.S. Patent Application No. U.S. 2003 0032043 A1 (Pohl and Papanu, "Latex Based Adsorbent Chip," Jul. 16, 2002); and PCT International Publication No. WO 03/040700 (Um et al., "Hydrophobic Surface Chip," May 15, 2003); U.S. Provisional Patent Application No. 60/367,837 (Boschetti et al., "Biochips With Surfaces Coated With Polysaccharide-Based Hydrogels," May 5, 2002) and U.S. patent application Ser. No. 60/448,467, entitled "Photocrosslinked Hydrogel Surface Coatings" (Huang et al., filed Feb. 21, 2003).

In general, a probe with an adsorbent surface is contacted with the sample for a period of time sufficient to allow biomarker or biomarkers that may be present in the sample to bind to the adsorbent. After an incubation period, the substrate is washed to remove unbound material. Any suitable washing solutions can be used; preferably, aqueous solutions are employed. The extent to which molecules remain bound can be manipulated by adjusting the stringency of the wash. The elution characteristics of a wash solution can depend, for example, on pH, ionic strength, hydrophobicity, degree of chaotropism, detergent strength, and temperature. Unless the probe has both SEAC and SEND properties (as described herein), an energy absorbing molecule then is applied to the substrate with the bound biomarkers.

The biomarkers bound to the substrates are detected in a gas phase ion spectrometer such as a time-of-flight mass spectrometer. The biomarkers are ionized by an ionization source such as a laser, the generated ions are collected by an ion optic assembly, and then a mass analyzer disperses and analyzes the passing ions. The detector then translates information of the detected ions into mass-to-charge ratios. Detection of a biomarker typically will involve detection of signal intensity. Thus, both the quantity and mass of the biomarker can be determined.

Another version of SELDI is Surface-Enhanced Neat Desorption (SEND), which involves the use of probes comprising energy absorbing molecules that are chemically bound to the probe surface ("SEND probe"). The phrase "energy absorbing molecules" (EAM) denotes molecules that are capable of absorbing energy from a laser desorption/ionization source and, thereafter, contribute to desorption and ionization of analyte molecules in contact therewith. The EAM category includes molecules used in MALDI, frequently referred to as "matrix," and is exemplified by cinnamic acid derivatives, sinapinic acid (SPA), cyano-hydroxy-cinnamic acid (CHCA) and dihydroxybenzoic acid, ferulic acid, and hydroxyacetophenone derivatives. In certain embodiments, the energy absorbing molecule is incorporated into a linear or cross-linked polymer, e.g., a polymethacrylate. For example, the composition can be a co-polymer of α-cyano-4-methacryloyloxycinnamic acid and acrylate. In another embodiment, the composition is a co-polymer of α-cyano-4-methacryloyloxycinnamic acid, acrylate and 3-(tri-ethoxy)silyl propyl methacrylate. In another embodiment, the composition is a co-polymer of α-cyano-4-methacryloyloxycinnamic acid and octadecylmethacrylate ("C18 SEND"). SEND is further described in U.S. Pat. No. 6,124,137 and PCT International Publication No. WO 03/64594 (Kitagawa, "Monomers And Polymers Having Energy Absorbing Moieties Of Use In Desorption/Ionization Of Analytes," Aug. 7, 2003).

SEAC/SEND is a version of SELDI in which both a capture reagent and an energy absorbing molecule are attached to the sample presenting surface. SEAC/SEND probes therefore allow the capture of analytes through affinity capture and ionization/desorption without the need to apply external matrix. The C18 SEND biochip is a version of SEAC/SEND, comprising a C18 moiety which functions as a capture reagent, and a CHCA moiety which functions as an energy absorbing moiety.

Another version of SELDI, called Surface-Enhanced Photolabile Attachment and Release (SEPAR), involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker profile, pursuant to the present invention.

2. Other Mass Spectrometry Methods

In another mass spectrometry method, the biomarkers can be first captured on a chromatographic resin having chromatographic properties that bind the biomarkers. In the present example, this could include a variety of methods. For example, one could capture the biomarkers on a cation exchange resin, such as CM Ceramic HyperD F resin, wash the resin, elute the biomarkers and detect by MALDI. Alternatively, this method could be preceded by fractionating the sample on an anion exchange resin before application to the cation exchange resin. In another alternative, one could fractionate on an anion exchange resin and detect by MALDI directly. In yet another method, one could capture the biomarkers on an immuno-chromatographic resin that comprises antibodies that bind the biomarkers, wash the resin to remove unbound material, elute the biomarkers from the resin and detect the eluted biomarkers by MALDI or by SELDI.

3. Data Analysis

Analysis of analytes by time-of-flight mass spectrometry generates a time-of-flight spectrum. The time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing. In Ciphergen's ProteinChip® software, data processing typically includes TOF-to-M/Z transformation to generate a mass spectrum, baseline subtraction to eliminate instrument offsets and high frequency noise filtering to reduce high frequency noise.

Data generated by desorption and detection of biomarkers can be analyzed with the use of a programmable digital computer. The computer program analyzes the data to indicate the number of biomarkers detected, and optionally the strength of the signal and the determined molecular mass for each biomarker detected; Data analysis can include steps of determining signal strength of a biomarker and removing data deviating from a predetermined statistical distribution. For example, the observed peaks can be normalized, by calculating the height of each peak relative to some reference. The reference can be background noise generated by the instrument and chemicals such as the energy absorbing molecule which is set at zero in the scale.

The computer can transform the resulting data into various formats for display. The standard spectrum can be displayed, but in one useful format only the peak height and mass information are retained from the spectrum view, yielding a cleaner image and enabling biomarkers with nearly identical molecular weights to be more easily seen. In another useful format, two or more spectra are compared, conveniently highlighting unique biomarkers and biomarkers that are up- or down-regulated between samples. Using any of these formats, one can readily determine whether a particular biomarker is present in a sample.

Analysis generally involves the identification of peaks in the spectrum that represent signal from an analyte. Peak selection can be done visually, but software is available, as part of Ciphergen's ProteinChip® software package, that can automate the detection of peaks. In general, this software functions by identifying signals having a signal-to-noise ratio above a selected threshold and labeling the mass of the peak at the centroid of the peak signal. In one useful application, many spectra are compared to identify identical peaks present in some selected percentage of the mass spectra. One version of this software clusters all peaks appearing in the various spectra within a defined mass range, and assigns a mass (M/Z) to all the peaks that are near the mid-point of the mass (M/Z) cluster.

Software used to analyze the data can include code that applies an algorithm to the analysis of the signal to determine whether the signal represents a peak in a signal that corresponds to a biomarker according to the present invention. The software also can subject the data regarding observed biomarker peaks to classification tree or ANN analysis, to determine whether a biomarker peak or combination of biomarker peaks is present that indicates the status of the particular clinical parameter under examination. Analysis of the data may be "keyed" to a variety of parameters that are obtained, either directly or indirectly, from the mass spectrometric analysis of the sample. These parameters include, but are not limited to, the presence or absence of one or more peaks, the shape of a peak or group of peaks, the height of one or more peaks, the log of the height of one or more peaks, and other arithmetic manipulations of peak height data.

4. General Protocol for SELDI Detection of Biomarkers for Alzheimer's Disease

A preferred protocol for the detection of the biomarkers of this invention is as follows. The sample to be tested is contacted with an affinity capture probe comprising an cation exchange adsorbent (preferably a CM-10 or WCX-2 ProteinChip array (Ciphergen Biosystems, Inc.)), an anion exchange adsorbent (preferably a Q-10 ProteinChip array (Ciphergen Biosystems, Inc.)), a hydrophobic exchange adsorbent (preferably a H50 ProteinChip array (Ciphergen Biosystems, Inc.)) and/or an IMAC adsorbent (preferably an IMAC30 ProteinChip array (Ciphergen Biosystems, Inc.)), again as indicated in Tables I and II. The probe is washed with a buffer that will retain the biomarker while washing away unbound molecules. Examples of suitable washes for each biomarker are the buffers identified in the Examples and in Table I. The biomarkers are detected by laser desorption/ionization mass spectrometry.

In some instances, the sample, e.g., serum, is subject to pre-fractionation before SELDI analysis. This simplifies the sample and improves sensitivity. A preferred method of pre-fractionation involves contacting the sample with an anion exchange chromatographic material, such as Q HyperD (Bio-Sepra, SA). The bound materials are then subject to stepwise pH elution using buffers at pH 9, pH 7, pH 5 and pH 4. (See, Example 1—Buffer list.) (The fractions in which the biomarkers are eluted may be indicated in, e.g., Table I.) Various fractions containing the biomarker are collected. Thereafter, the fractions containing the biomarkers are subjected to SELDI analysis as described above.

Alternatively, if antibodies that recognize the biomarker are available, for example in the case of β2-microglobulin, cystatin, transferrin, transthyretin, hemopexin, WT ABri/ ADan Amyloid Peptide, full length Cystatin C, Cystatin C ΔN1-8, N-terminal fragments of Neurosecretory Protein VGF, Complement 3a des-Arg, C-terminal fragment of Neuroendocrine protein 7B2, and Secretoneurin, these can be attached to the surface of a probe, such as a pre-activated PS10 or PS20 ProteinChip array (Ciphergen Biosystems, Inc.). These antibodies can capture the biomarkers from a sample onto the probe surface. Then the biomarkers can be detected by, e.g., laser desorption/ionization mass spectrometry.

B. Detection by Immunoassay

In another embodiment, the biomarkers of this invention can be measured by immunoassay. Immunoassay requires biospecific capture reagents, such as antibodies, to capture the biomarkers. Antibodies can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well known in the art.

This invention contemplates traditional immunoassays including, for example, sandwich immunoassays including ELISA or fluorescence-based immunoassays, as well as other enzyme immunoassays. In the SELDI-based immunoassay, a biospecific capture reagent for the biomarker is attached to the surface of an MS probe, such as a pre-activated ProteinChip array. The biomarker is then specifically captured on the biochip through this reagent, and the captured biomarker is detected by mass spectrometry.

IV. Determination of Subject Alzheimer's Disease Status

A. Single Markers

The biomarkers of the invention can be used in diagnostic tests to assess Alzheimer's disease status in a subject, e.g., to diagnose Alzheimer's disease. The phrase "Alzheimer's disease status" includes distinguishing, inter alia, Alzheimer's disease v. non-Alzheimer's disease and, in particular, Alzheimer's disease v. non-Alzheimer's disease normal or Alzheimer's disease v. non-Alzheimer's disease dementia. Based on this status, further procedures may be indicated, including additional diagnostic tests or therapeutic procedures or regimens.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of actual positives who test as positive. Negative predictive value is the percentage of actual negatives that test as negative.

The biomarkers of this invention show a statistical difference in different Alzheimer's disease statuses of at least $p \leq 0.05$, $p \leq 10^{-2}$, $p \leq 10^{-3}$, $p \leq 10^{-4}$ or $p \leq 10^{-5}$. Diagnostic tests that use these biomarkers alone or in combination show a sensitivity and specificity of at least 75%, at least 80%, at least 85%, at least 90%, at least 95%, at least 98% and about 100%.

Each biomarker listed in Tables I, II and IV are differentially present in Alzheimer's disease, and, therefore, each is individually useful in aiding in the determination of Alzheimer's disease status. The method involves, first, measuring the selected biomarker in a subject sample using the methods described herein, e.g., capture on a SELDI biochip followed by detection by mass spectrometry and, second, comparing the measurement with a diagnostic amount or cut-off that distinguishes a positive Alzheimer's disease status from a negative Alzheimer's disease status. The diagnostic amount represents a measured amount of a biomarker above which or below which a subject is classified as having a particular Alzheimer's disease status. For example, if the biomarker is up-regulated compared to normal during Alzheimer's disease, then a measured amount above the diagnostic cutoff provides a diagnosis of Alzheimer's disease. Alternatively, if the biomarker is down-regulated during Alzheimer's disease, then a measured amount below the diagnostic cutoff provides a diagnosis of Alzheimer's disease.

Similarly, if the biomarker is up-regulated compared to normal during non-Alzheimer's dementia, then a measured amount above the diagnostic cutoff provides a diagnosis of non-Alzheimer's dementia. Alternatively, if the biomarker is down-regulated during non-Alzheimer's dementia compared to Alzheimer's disease, then a measured amount below the diagnostic cutoff provides a diagnosis of non-Alzheimer's dementia (i.e., a negative diagnosis of Alzheimer's disease).

As is well understood in the art, by adjusting the particular diagnostic cut-off used in an assay, one can increase sensitivity or specificity of the diagnostic assay depending on the preference of the diagnostician. The particular diagnostic cut-off can be determined, for example, by measuring the amount of the biomarker in a statistically significant number of samples from subjects with the different Alzheimer's disease statuses, as was done here, and drawing the cut-off to suit the diagnostician's desired levels of specificity and sensitivity.

B. Combinations of Markers

While individual biomarkers are useful diagnostic biomarkers, it has been found that a combination of biomarkers can provide greater predictive value of a particular status than single biomarkers alone. Specifically, the detection of a plurality of biomarkers in a sample can increase the sensitivity and/or specificity of the test.

The protocols described in the Examples were used to generate mass spectra from patient samples that were diagnosed with Alzheimer's disease and no dementia. The peak masses and heights were abstracted into a discovery data set. This data set was used to train a learning algorithm employing classification and regression tree analysis (CART) (Ciphergen Biomarker Patterns Software™). In particular, CART chose many subsets of the peaks at random. For each subset, CART generated a best or near best decision tree to classify a sample as Alzheimer's disease or non-Alzheimer's disease. Among the many decision trees generated by CART, several had excellent sensitivity and specificity in distinguishing Alzheimer's disease from non-Alzheimer's disease.

Figure 2:
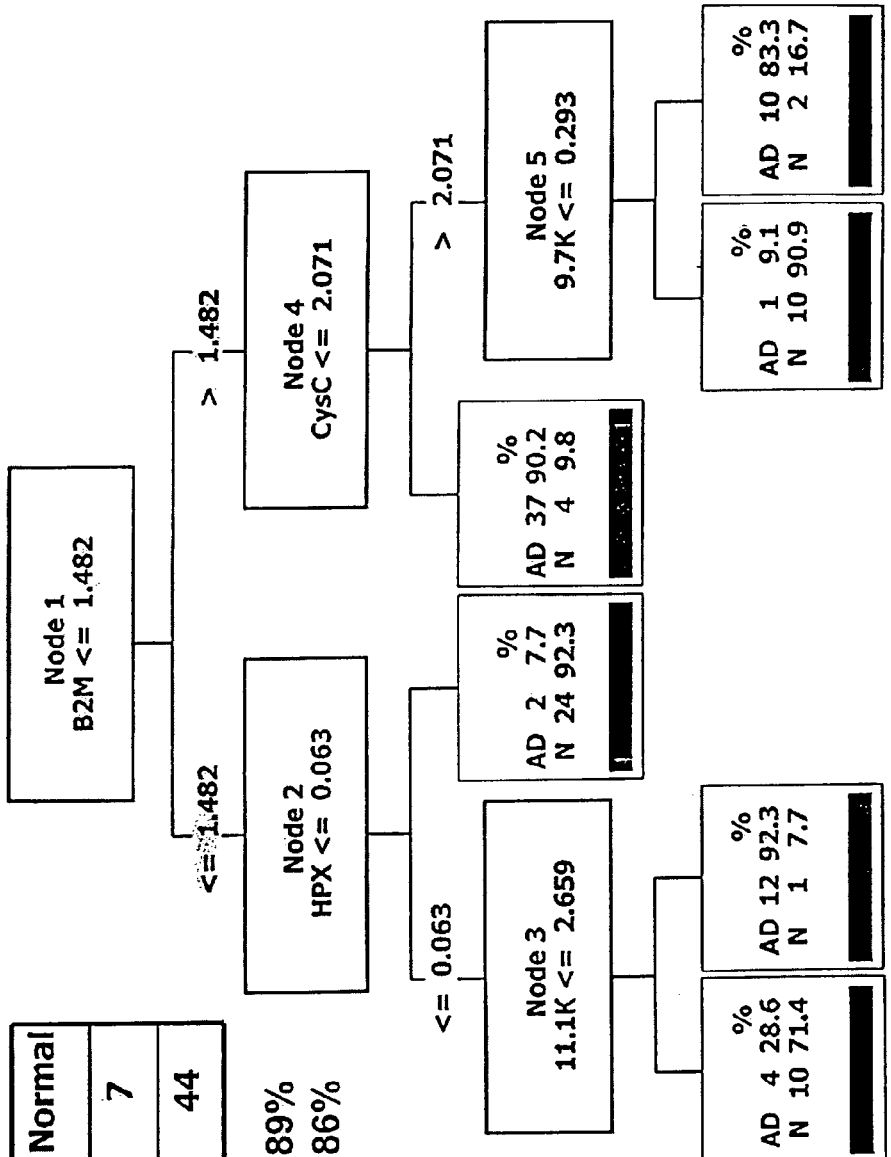
FIG. 2A shows a decision tree for classifying a sample as Alzheimer's or non-Alzheimer's using certain biomarkers of this invention.

An exemplar decision tree is presented in FIG. 2. This decision tree uses M11753.4 (β2 microglobulin, therein "B2M"), M60976.2 (Hemopexin, therein "HPX"), M13391 (Cystatin C, therein "CysC"), M11.1K and M9.7K. Accordingly, these biomarkers are recognized as powerful classifiers for Alzheimer's disease when used in combination with each other and, optionally, with other biomarkers. In particular, when used together or in further combination with, for example, M78677.3 (Transferrin), M2432.2 (WT ABri/ADan Amyloid Peptide), M12583.4 (Cystatin C ΔN1-8), M3687.7 (N-terminal fragment of Neurosecretory Protein VGF); M3951.6 (N-terminal fragment of Neurosecretory Protein VGF), M8933.2 (Complement 3a des-Arg), M3514.5 (C-terminal fragment of Neuroendocrine protein 7B2) and M3680.7 (Secretoneurin), these markers can distinguish Alzheimer's disease from non-Alzheimer's disease with sensitivities of at least 89% and specificities of at least 86%.

It is also noted that the specifics of a decision tree, in particular the cut-off values used in making branching decisions, depends on the details of the assay used to generate the discovery data set. The data acquisition parameters of the assay that produced the data used in the present analysis is provided in Example 3. In developing a classification algorithm from, for example, a new sample set or a different assay protocol, the operator uses a protocol that detects these biomarkers and keys the learning algorithm to include them.

In the decision tree set forth in FIG. 2, biomarkers M11753.4 (β2 microglobulin, therein "B2M"), M60976.2 (Hemopexin, therein "HPX"), M13391 (Cystatin C, therein "CysC"), M11.1K and M9.7K. are particularly useful in combination to classify Alzheimer's disease v. non-Alzheimer's disease. This combination is particularly useful in a recursive partitioning process as shown in FIG. 2. Again, the measure of each cut-off depends on the particulars of the assay protocol, of course. In this case, the cut-offs are based on the protocol set forth in Example 3.

In this decision tree, B2M is the root decision node of the decision tree. Subjects having an amount of this biomarker above the cut-off (i.e., M11753.4<=1.482) are sent to node 4 based on CysC.

Subjects having an amount of M13391 below the cut-off (i.e., CysC<=2.071) are classified as Alzheimer's. Subjects having an amount of M13391 above the cut-off (i.e., CysC<=2.071) are sent to node 5 based on M9.7K.

Subjects having an amount of M9.7K below the cut-off (i.e., M9.7K<=0.293) are classified as normal. Subjects having an amount of M9.7K above the cut-off (i.e., M9.7K<=0.293) are classified as Alzheimer's.

Subjects having an amount of the biomarker B2M below the cut-off (i.e., M11753.4<=1.482) are sent to node 2 based on HPX.

Subjects having an amount of HPX above the cut-off (i.e., M60976.2<=0.063) are classified as Alzheimer's. Subjects having an amount of HPX below the cut-off (i.e., M60976.2<=0.063) are sent to node three based on M11.1K.

Subjects having an amount of M11.1K below the cut-off (i.e., M11.1K<=2.659) are classified as normal. Subjects having an amount of M11.1K above the cut-off (i.e., M11.1K<=2.659) are classified as Alzheimer's.

As set forth in FIG. 2, this decision tree has a sensitivity of about 89%, and a specificity of about 86%.

C. Determining Risk of Developing Disease

In one embodiment, this invention provides methods for determining the risk of developing Alzheimer's disease in a subject. Biomarker amounts or patterns are characteristic of various risk states, e.g., high, medium or low. The risk of developing Alzheimer's disease is determined by measuring the relevant biomarker or biomarkers and then either submitting them to a classification algorithm or comparing them with a reference amount and/or pattern of biomarkers that is associated with the particular risk level.

D. Determining Stage of Disease

In one embodiment, this invention provides methods for determining the stage of Alzheimer's disease in a subject. Each stage of the disease has a characteristic amount of a biomarker or relative amounts of a set of biomarkers (a pattern). The stage of a disease is determined by measuring the relevant biomarker or biomarkers and then either submitting them to a classification algorithm or comparing them with a reference amount and/or pattern of biomarkers that is associated with the particular stage.

E. Determining Course (Progression/Remission) of Disease

In one embodiment, this invention provides methods for determining the course of Alzheimer's disease in a subject. Disease course refers to changes in disease status over time, including disease progression (worsening) and disease regression (improvement). Over time, the amounts or relative amounts (e.g., the pattern) of the biomarkers changes. For example, the concentrations of biomarkers M9984.6 and M10265.6 (Table IV-B) are increased in samples from Alzheimer's patients, while the concentration of hemopexin is decreased in samples from Alzheimer's patients. Therefore, the trend of these markers, either increased or decreased over time toward diseased or non-diseased indicates the course of the disease. Accordingly, this method involves measuring one or more biomarkers in a subject at least two different time points, e.g., a first time and a second time, and comparing the change in amounts, if any. The course of disease is determined based on these comparisons. Similarly, this method is useful for determining the response to treatment. If a treatment is effective, then the biomarkers will trend toward normal, while if treatment is ineffective, the biomarkers will trend toward disease indications.

F. Subject Management

In certain embodiments of the methods of qualifying Alzheimer's disease status, the methods further comprise managing subject treatment based on the status. Such management includes the actions of the physician or clinician subsequent to determining Alzheimer's disease status. For example, if a physician makes a diagnosis of Alzheimer's disease, then a certain regime of treatment, such as prescription or administration of cholinesterase inhibitors, antiglutamatergic therapy or antioxidants, might follow. Alternatively, a diagnosis of non-Alzheimer's disease or non-Alzheimer's disease dementia might be followed with further testing to determine a specific dementia that might the patient might be suffering from. Also, if the diagnostic test gives an inconclusive result on Alzheimer's disease status, further tests may be called for.

Additional embodiments of the invention relate to the communication of assay results or diagnoses or both to technicians, physicians or patients, for example. In certain embodiments, computers will be used to communicate assay results or diagnoses or both to interested parties, e.g., physicians and their patients. In some embodiments, the assays will be performed or the assay results analyzed in a country or jurisdiction which differs from the country or jurisdiction to which the results or diagnoses are communicated.

In a preferred embodiment of the invention, a diagnosis based on the presence or absence in a test subject of any the biomarkers of Tables I, II, IV-A, B or V is communicated to the subject as soon as possible after the diagnosis is obtained. The diagnosis may be communicated to the subject by the subject's treating physician. Alternatively, the diagnosis may be sent to a test subject by email or communicated to the subject by phone. A computer may be used to communicate the diagnosis by email or phone. In certain embodiments, the message containing results of a diagnostic test may be generated and delivered automatically to the subject using a combination of computer hardware and software which will be familiar to artisans skilled in telecommunications. One example of a healthcare-oriented communications system is described in U.S. Pat. No. 6,283,761; however, the present invention is not limited to methods which utilize this particular communications system. In certain embodiments of the methods of the invention, all or some of the method steps, including the assaying of samples, diagnosing of diseases, and communicating of assay results or diagnoses, may be carried out in diverse (e.g., foreign) jurisdictions.

V. Generation of Classification Algorithms for Qualifying Alzheimer's Disease Status In some embodiments, data derived from the spectra (e.g., mass spectra or time-of-flight spectra) that are generated using samples such as "known samples" can then be used to "train" a classification model. A "known sample" is a sample that has been pre-classified. The data that are derived from the spectra and are used to form the classification model can be referred to as a "training data set." Once trained, the classification model can recognize patterns in data derived from spectra generated using unknown samples. The classification model can then be used to classify the unknown samples into classes. This can be useful, for example, in predicting whether or not a particular biological sample is associated with a certain biological condition (e.g., diseased versus non-diseased).

The training data set that is used to form the classification model may comprise raw data or pre-processed data. In some embodiments, raw data can be obtained directly from time-of-flight spectra or mass spectra, and then may be optionally "pre-processed" as described above.

Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review", *IEEE Transactions on Pattern Analysis and Machine Intelligence*, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART—classification and regression trees), artificial neural networks such as back propagation networks, discriminant analyses (e.g., Bayesian classifier or Fischer analysis), logistic classifiers, and support vector classifiers (support vector machines).

A preferred supervised classification method is a recursive partitioning process. Recursive partitioning processes use recursive partitioning trees to classify spectra derived from unknown samples. Further details about recursive partitioning processes are provided in U.S. Patent Application Ser. No. 2002 0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application Ser. No. 2002 0193950 A1 (Gavin et al., "Method or analyzing mass spectra"), U.S. Patent Application Ser. No. 2003 0004402 A1 (Hitt et al., "Process for discriminating between biological states based on hidden patterns from biological data"), and U.S. Patent Application Ser. No. 2003 0055615 A1 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows™ or Linux™ based operating system. The digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including C, C++, visual basic, etc.

The learning algorithms described above are useful both for developing classification algorithms for the biomarkers already discovered, or for finding new biomarkers for Alzheimer's disease. The classification algorithms, in turn, form the base for diagnostic tests by providing diagnostic values (e.g., cut-off points) for biomarkers used singly or in combination.

VI. Kits for Detection of Biomarkers for Alzheimer's Disease

In another aspect, the present invention provides kits for qualifying Alzheimer's disease status, which kits are used to detect biomarkers according to the invention. In one embodiment, the kit comprises a solid support, such as a chip, a microtiter plate or a bead or resin having a capture reagent attached thereon, wherein the capture reagent binds a biomarker of the invention. Thus, for example, the kits of the present invention can comprise mass spectrometry probes for SELDI, such as ProteinChip® arrays. In the case of biospecfic capture reagents, the kit can comprise a solid support with a reactive surface, and a container comprising the biospecific capture reagent.

The kit can also comprise a washing solution or instructions for making a washing solution, in which the combination of the capture reagent and the washing solution allows capture of the biomarker or biomarkers on the solid support for subsequent detection by, e.g., mass spectrometry. The kit may include more than type of adsorbent, each present on a different solid support.

In a further embodiment, such a kit can comprise instructions for suitable operational parameters in the form of a label or separate insert. For example, the instructions may inform a consumer about how to collect the sample, how to wash the probe or the particular biomarkers to be detected.

In yet another embodiment, the kit can comprise one or more containers with biomarker samples, to be used as standard(s) for calibration.

VII. Determining the Quality of an Immunoassay Calibrator

Calibration of an immunoassay is important for ensuring the quality of results generated in the immunoassay. Calibration generally involves the use of an immunoassay calibrator that contains the target analyte in a prescribed amount or concentration. The signal produced by the calibrator in an immunoassay is correlated to the amount of target analyte in the calibrator. This calibration, in turn, is used to correlate the amount of signal measured in a test sample with an amount of target analyte in the test sample. However, the signal generated by the calibrator may not represent the true amount of analyte in the calibrator if, for example, the target analyte in the calibrator is degraded or otherwise modified so as to corrupt the signal.

For example, in one embodiment, this invention provides a method for determining the quality of a Cystatin immunoassay calibrator. The method involves capturing molecules from a immunoassay calibrator used in an immunoassay against Cystatin with an antibody that captures Cystatin, and specifically measuring the amount of Cystatin or one or more modified forms of Cystatin captured by the antibody. Alternatively, the immunoassay could be directed to measuring a particular modified form of Cystatin and involve the use of antibodies against this form and a calibrator that included this form.

As mentioned above, once calibrated, an immunoassay capable of accurately measuring levels of modified Cystatin polypeptides, e.g., Cystatin C $\Delta$N1-8, may be used to determine the likelihood that a subject diagnosed with dementia is suffering from Alzheimer's disease as opposed to some form of non-Alzheimer's dementia.

Similarly, the invention also provides a method for determining the quality of any immunossay calibrator used in an immunassay against any of the biomarkers disclosed herein, comprising the same steps described above with respect to a Cystatin immunoassay calibrator.

VIII. Determining the Quality of an Antibody in an Antibody Reagent Used in an Immunoassay Immunoassays typically involve the use an immunoassay reagent that comprises an antibody directed against the target analyte. The accuracy of such assays depends upon the integrity and purity of the antibody in the immunoassay reagent. The presence of contaminants in an antibody reagent can interfere with an accurate measurement of the amount of antibody in the antibody reagent. For example, the present invention provides methods for determining the quality of an antibody against an AD biomarker, as used in an immunoassay reagent, by specifically detecting modified, e.g., degraded, forms of the antibody in the reagent.

The performance of the assay will be tested alone and in combination with other markers to diagnose and monitor treatment of patients, e.g., dementia patients. Initially, different types of dementia samples including AD and non-AD dementias along with aged normal samples will be analysed to determine assay sensitivity and specificity. The utility of the assay will be determined both for cerebrospinal fluid and matched serum samples. The ultimate objectives are to produce a test that will improve the early diagnosis of AD patients, help with stratification of patients for enrollment in clinical trials and provide a surrogate marker for drug treatment response.

IX. Use of Biomarkers for Alzheimer's Disease in Screening Assays and Methods of Treatment The methods of the present invention have other applications as well. For example, the biomarkers can be used to screen for compounds that modulate the expression of the biomarkers in vitro or in vivo, which compounds in turn may be useful in treating or preventing Alzheimer's disease in patients. In another example, the biomarkers can be used to monitor the response to treatments for Alzheimer's disease. In yet another example, the biomarkers can be used in heredity studies to determine if the subject is at risk for developing Alzheimer's disease.

Thus, for example, the kits of this invention could include a solid substrate having an cation exchange function, such as a protein biochip (e.g., a Ciphergen WCX2 ProteinChip array, e.g., ProteinChip array) and a sodium acetate buffer for washing the substrate, as well as instructions providing a protocol to measure the biomarkers of this invention on the chip and to use these measurements to diagnose Alzheimer's disease.

Compounds suitable for therapeutic testing may be screened initially by identifying compounds which interact with one or more biomarkers listed in Tables I, II, IV-A, IV-B or V. By way of example, screening might include recombinantly expressing a biomarker listed in Tables I, II, IV-A, IV-B or V, purifying the biomarker, and affixing the biomarker to a substrate. Test compounds would then be contacted with the substrate, typically in aqueous conditions, and interactions between the test compound and the biomarker are measured, for example, by measuring elution rates as a function of salt concentration. Certain proteins may recognize and cleave one or more biomarkers of Tables I, II, IV-A, IV-B or V, such as Cystatin C, in which case the proteins may be detected by monitoring the digestion of one or more biomarkers in a standard assay, e.g., by gel electrophoresis of the proteins.

In a related embodiment, the ability of a test compound to inhibit the activity of one or more of the biomarkers of Tables I, II, IV-A, IV-B, or V may be measured. One of skill in the art will recognize that the techniques used to measure the activity of a particular biomarker will vary depending on the function and properties of the biomarker. For example, an enzymatic activity of a biomarker may be assayed provided that an appropriate substrate is available and provided that the concentration of the substrate or the appearance of the reaction product is readily measurable. The ability of potentially therapeutic test compounds to inhibit or enhance the activity of a given biomarker may be determined by measuring the rates of catalysis in the presence or absence of the test compounds. The ability of a test compound to interfere with a non-enzymatic (e.g., structural) function or activity of one of the biomarkers of Tables I, II, IV-A, IV-B or V may also be measured. For example, the self-assembly of a multi-protein complex which includes one of the biomarkers of Tables I, II, IV-A, IV-B or V may be monitored by spectroscopy in the presence or absence of a test compound. Alternatively, if the biomarker is a non-enzymatic enhancer of transcription, test compounds which interfere with the ability of the biomarker to enhance transcription may be identified by measuring the levels of biomarker-dependent transcription in vivo or in vitro in the presence and absence of the test compound.

Test compounds capable of modulating the activity of any of the biomarkers of Table I may be administered to patients who are suffering from or are at risk of developing Alzheimer's disease or other dementia's. For example, the administration of a test compound which increases the activity of a particular biomarker may decrease the risk of Alzheimer's in a patient if the activity of the particular biomarker in vivo prevents the accumulation of proteins for Alzheimer's disease. Conversely, the administration of a test compound which decreases the activity of a particular biomarker may decrease the risk of Alzheimer's disease in a patient if the increased activity of the biomarker is responsible, at least in part, for the onset of Alzheimer's disease.

In an additional aspect, the invention provides a method for identifying compounds useful for the treatment of disorders such as Alzheimer's disease which are associated with increased levels of modified forms of any of the biomarkers of Tables I, II, IV-A, IV-B or V, such as cystatin C. For example, in one embodiment, cell extracts or expression libraries may be screened for compounds which catalyze the cleavage of full-length biomarkers, e.g., cystatin C, to form truncated forms of the biomarkers, e.g., Cystatin C $\Delta$N1-8. For example, in one embodiment of such a screening assay, cleavage of cystatin C may be detected by attaching a fluorophore to cystatin C which remains quenched when cystatin C is uncleaved but which fluoresces when the protein is cleaved between positions 8 and 9. Alternatively, a version of full-length cystatin C modified so as to render the amide bond between amino acids 8 and 9 uncleavable may be used to selectively bind or "trap" the cellular protease which cleaves full-length cystatin C at that site in vivo. Methods for screening and identifying proteases and their targets are well-documented in the scientific literature, e.g., in Lopez-Ottin et al. (Nature Reviews, 3:509-519 (2002)).

In yet another embodiment, the invention provides a method for treating or reducing the progression or likelihood of a disease, e.g., Alzheimer's disease, which is associated with the increased levels of one or more of the biomarkers described herein, for example, Cystatin C $\Delta$1-8. For example, after one or more proteins have been identified which cleave full-length cystatin C between amino acids 8 and 9, combinatorial libraries may be screened for compounds which inhibit the cleavage activity of the identified proteins. Methods of screening chemical libraries for such compounds are well-known in art. See, e.g., Lopez-Otin et al. (2002). Alternatively, inhibitory compounds may be intelligently designed based on the structure of cystatin C.

The compounds tested as modulators of the relative levels of full-length versus truncated biomarkers, e.g., cystatin C versus truncated Cystatin C $\Delta$1-8, can be any small chemical compound, or a biological entity, such as a protein, sugar, nucleic acid or lipid. Alternatively, modulators can be proteases or genetically engineered proteases. Typically, test compounds will be small chemical molecules and peptides. Essentially any chemical compound can be used as a potential modulator or binding compound in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

Where the modification of a particular biomarker is associated with Alzheimer's disease or a non-Alzheimer's dementia, and where the modification is non-proteolytic, e.g., where the biomarker is glycosylated, acetylated, or phosphorylated, the modulating enzyme can be similarly targeted by compounds which inhibit the modulating enzyme's activity, specifically or generally. Likewise, where an increased concentration of an unmodified form of a particular biomarker is associated with Alzheimer's disease or a non-Alzheimer's dementia, the activity of the appropriate modulating enzyme may be increased by the addition of exogenous compounds which enhance the activity of the modulating enzyme, directly or indirectly, or by the recombinant addition of the appropriate modulating enzyme(s). Note that virtually any activity which affects the amount of a biomarker or the extent to which the biomarker found in modified form can be targeted. For example, chromogranin peptide fragments that are generated by disease regulated prohormone convertases (PC) can be modulated by targeting the activity of the prohormone convertases.

In one preferred embodiment, high throughput screening methods involve providing a combinatorial chemical or peptide library containing a large number of potential therapeutic compounds (potential modulator or binding compounds). Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

Full-length cystatin C is believed to bind to and inhibit the activity of human lysosomal proteases such as cathepsins B and L. N-terminal truncations of cystatin C are thought to diminish cystatin C's protease inhibitory activity. See, e.g., Abrahamson et al. (Biochem. J. 273:621-626 (1991)). Compounds which impart truncated cystatin C with the functionality of full-length cystatin C are likely therefore to be useful in treating conditions, such as Alzheimer's disease, which are associated with the truncated form of cystatin C. Therefore, in a further embodiment, the invention provides methods for identifying compounds which increase the affinity of truncated cystatin C for its target proteases, e.g., various cathepsins. For example, compounds may be screened for their ability to impart truncated cystatin C with the protease inhibitory activity of full-length cystatin C. Test compounds capable of modulating the inhibitory activity of cystatin C or the activity of molecules which interact with cystatin C may then be tested in vivo for their ability to slow or stop the progression of Alzheimer's disease in a subject.

At the clinical level, screening a test compound includes obtaining samples from test subjects before and after the subjects have been exposed to a test compound. The levels in the samples of one or more of the biomarkers listed in Table I may be measured and analyzed to determine whether the levels of the biomarkers change after exposure to a test compound. The samples may be analyzed by mass spectrometry, as described herein, or the samples may be analyzed by any appropriate means known to one of skill in the art. For example, the levels of one or more of the biomarkers listed in Table I may be measured directly by Western blot using radio- or fluorescently-labeled antibodies which specifically bind to the biomarkers. Alternatively, changes in the levels of mRNA encoding the one or more biomarkers may be measured and correlated with the administration of a given test compound to a subject. In a further embodiment, the changes in the level of expression of one or more of the biomarkers may be measured using in vitro methods and materials. For example, human tissue cultured cells which express, or are capable of expressing, one or more of the biomarkers of Tables I, II, IV-A, IV-B or V may be contacted with test compounds. Subjects who have been treated with test compounds will be routinely examined for any physiological effects which may result from the treatment. In particular, the test compounds will be evaluated for their ability to diminish the likelihood of disease in a subject. Alternatively, if the test compounds are administered to subjects who have previously been diagnosed with Alzheimer's disease, test compounds will be screened for their ability to slow or stop the progression of the disease.

The invention will be described in greater detail by way of specific examples. The following examples are offered for illustrative purposes, and are not intended to limit the invention in any manner. Those of skill in the art will readily recognize a variety of non-critical parameters that can be changed or modified to yield essentially the same results.

X. Use of Biomarkers for Imaging

Non-invasive medical imaging techniques such as Positron Emisson Tomography (PET) or single photon emission computerized tomography (SPECT) imaging are particularly useful for the detection of cancer, coronary artery disease and brain disease. PET and SPECT imaging shows the chemical functioning of organs and tissues, while other imaging techniques—such as X-ray, CT and MRI—show structure. The use of PET and SPECT imaging has become increasingly useful for qualifying and monitoring the development of brain diseases such as Alzheimer's disease. In some instances, the use of PET or SPECT imaging allows Alzheimer's disease to be detected several years earlier than the onset of symptoms.

Different strategies are being used to develop compounds suitable for in vivo imaging of amyloid deposits in human brains. Monoclonal antibodies against A-beta and peptide fragments have had limited uptake by the brain when tested in patients with AD. The small molecular approach for amyloid imaging has so far been most successful, as described by, e.g., Nordberg A, Lancet Neurol., 3(9):519-27 (2004); Kung M P et al, Brain Res., 1025(1-2):98-105 (2004); Herholz K et al., Mol Imaging Biol., 6(4):239-69 (2004); Neuropsychol Rev., Zakzanis K K et al., 13(1):1-18 (2003); Herholz K, Ann Nucl Med., 17(2):79-89 (2003).

The peptide biomarkers disclosed herein, or fragments thereof, can be used in the context of PET and SPECT imaging applications. After modification with appropriate tracer residues for PET or SPECT applications, peptide biomarkers which interact with amyloid plaque proteins can be used to image the deposition of amyloid plaques in Alzheimer's patients. For example, the AD biomarker alpha(1)-antichymotrypsin (ACT) is associated with neurotoxic amyloid deposits. The M4357 ACT CT fragment described in Table IV-B, or a sub-fragment thereof, may therefore be used as a probe for PET or SPECT imaging applications.

XI. Examples

Example 1

Discovery of Biomarkers for Alzheimer's Disease

The protocols described in the Example below were used to generate mass spectra from 65 Swedish patient samples, 30 of whom were diagnosed with Alzheimer's disease and 35 of whom did not exhibit dementia. For this study, patients were diagnosed as AD patients according to NINCDS-ADRDA criteria, which includes cognitive testing, routine blood and urine tests, MRI or CT imaging when applicable, and measurements of CSF Tau and A-Beta(42). Severity of dementia assessed using Mini Mental State Examination (MMSE). The 30 Alzheimer's samples were taken from patients with an average MMSE of 21 (range from 5 to 30). The 35 control patients were age-matched, with a mean MMSE of 29 (range from 25-30). MMSE scores greater than 18 are considered evidence of mild dementia and patients with MMSE scores greater than 24 are considered to be extremely mild cases.

1. Anion Exchange Fractionation
Buffer List for anion exchange fractionation:
U1 (1M urea, 0.22% CHAPS, 50 mM Tris-HCl pH9)
50 mM Tris-HCl with 0.1% OGP pH9 (Wash buffer 1)
50 mM Hepes with 0.1% OGP pH7 (Wash buffer 2)
100 mM NaAcetate with 0.1% OGP pH5 (Wash buffer 3)
100 mM NaAcetate with 0.1% OGP pH4 (Wash buffer 4)
33.3% isopropanol/16.7% acetonitrile/0.1% trifluoracetic acid (Wash buffer 5)

Note: do not aliquot wash buffer 5 into the buffer tray until wash buffer 4 is being applied to the resin. This ensures that evaporation of the volatile organic solvents will not be an issue.

Material List:
Filter plate
5 v-well 96 well dishes, labeled F1-F5.
a. Wash Resin
Prepare resin by washing Hyper Q DF resin (BioSepra, Cergy, France) 3 times with 5 bed volumes 50 mM Tris-HCl pH9. Then store in 50 mM Tris-HCl pH9 in a 50% suspension.
b. Equilibrate Resin
Add 125 µL Hyper Q DF to each well in filter plate
Filter buffer
Add 150 µL U1 to each well
Filter buffer
Add 150 µL U1 to each well
Filter buffer
Add 150 µL U1 to each well
Filter buffer
c. Bind CSF with Resin
Pipet 150 µL of sample from each tube to appropriate well in filter plate
Vortex 30' at 4°
d. Collect Fractions
Place v-well 96 well plate F1 under filter plate
Collect flow-through in plate F1
Add 100 µL of wash buffer 1 to each well of filter plate
Vortex 10' at Room Temperature (RT)
Collect pH 9 eluant in plate F1
Fraction 1 contains the flow through and the pH 9 eluant.
Add 100 µL of wash buffer 2 to each well of filter plate
Vortex 10' at Room Temperature (RT)
Place v-well 96 well plate F2 under filter plate
Collect fraction 2 in plate F2
Add 100 µL of wash buffer 2 to each well of filter plate
Vortex 10' at Room Temperature (RT)
Collect remainder of fraction 2 in plate F2
Fraction 2 contains the pH 7 eluant.
Add 100 µL of wash buffer 3 to each well of filter plate
Vortex 10' at Room Temperature (RT)
Place v-well 96 well plate F3 under filter plate
Collect fraction 3 in plate F3
Add 100 µL of wash buffer 3 to each well of filter plate
Vortex 10' at Room Temperature (RT)
Collect remainder of fraction 3 in plate F3
Fraction 3 contains the pH 5 eluant
Add 100 µL of wash buffer 4 to each well of filter plate
Vortex 10' at Room Temperature (RT)
Place v-well 96 well plate F4 under filter plate
Collect fraction 4 in plate F4
Add 100 µL of wash buffer 4 to each well of filter plate
Vortex 10' at Room Temperature (RT)
Collect remainder of fraction 4 in plate F4
Fraction 4 contains the pH 4 eluant.
Add 100 µL of wash buffer 5 to each well of filter plate
Vortex 10' at Room Temperature (RT)
Place v-well 96 well plate F5 under filter plate
Collect fraction 5 in plate F5
Add 100 µL of wash buffer 5 to each well of filter plate Vortex 10' at Room Temperature (RT)
Collect remainder of fraction 5 in plate F5
Fraction 5 contains the organic solvent eluant.
Freeze until proceeding with chip binding protocol
2. Chip Binding Protocol.
Bind CSF fractions to chips
Add 60 μL of corresponding buffer into each well
Add 20 μL of Q column fraction
Chip Washing Buffer list:
IMAC3 array (Ciphergen Biosystems, Inc.)
100 mM $CuSO_4$
100 mM Sodium Phosphate+0.5M NaCl pH 7
WCX2 array (Ciphergen Biosystems, Inc.)
100 mM Sodium Acetate pH 4
H50 array (Ciphergen Biosystems, Inc.)
10% Acetonitrile+0.1% TFA
Array preparation
Place arrays into bioprocessor
Load IMAC arrays with copper
Load 50 μl of $CUSO_4$ onto each spot of the IMAC3 array
Vortex 5' at Room Temperature (RT)
Remove $CuSO_4$ and repeat
Water rinse
Equilibrate arrays
Add 100 μl chip washing buffer appropriate to the array to each well
Vortex 5' at RT
Remove buffer after vortex
Add 100 μl chip washing buffer appropriate to the array to each well
Vortex 5' at RT
Remove buffer after vortex
Bind CSF fractions to arrays
Add 60 μl chip washing buffer appropriate to the array to each well
Add 20 μl CSF fraction
Vortex 30' at RT
Remove sample and buffer
Wash arrays
Add 100 μl chip washing buffer appropriate to the array to each well
Vortex 5' at RT
Remove buffer after vortex
Add 100 μl chip washing buffer appropriate to the array to each well
Vortex 5' at RT
Remove buffer after vortex
Add 100 μl chip washing buffer appropriate to the array to each well
Vortex 5' at RT
Remove buffer after vortex
Water rinse 2 times
Add matrix
Remove Bioprocessor top and gasket
Allow the arrays to dry
SPA:
Add 1 μl 50% SPA (sinapinic acid) in 50% Acetonitrile and 0.5% TFA
Air dry
Add 1 μl 50% SPA
Air dry
3. Data Acquisition Settings:
Energy absorbing molecule: 50% SPA
Set high mass to 100000 Daltons, optimized from 2000 Daltons to 100000 Daltons
Set starting laser intensity to 200
Set starting detector sensitivity to 8
Focus mass at 8000 Daltons
Set Mass Deflector to 1000 Daltons
Set data acquisition method to Seldi Quantitation
Set Seldi acquisition parameters 20. delta to 4. transients per to 10 ending position to 80
Set warming positions with 2 shots at intensity 225 and do not include warming shots
Process sample.
4. Determination of Biomarker Identity.

The spectra obtained were analyzed by Ciphergen Express™ Data Manager Software with Biomarker Wizard and Biomarker Pattern Software from Ciphergen Biosystems, Inc. The mass spectra for each group were subjected to scatter plot analysis. A Mann-Whitney test analysis was employed to compare Alzheimer's disease and control groups for each protein cluster in the scatter plot, and proteins were selected that differed significantly ($p<0.0001$) between the two groups.

Examples of the biomarkers thus discovered are presented in Table I below. The "ProteinChip assay" column refers to chromatographic fraction in which the biomarker is found, the type of biochip to which the biomarker binds and the wash conditions.

TABLE I

| Marker | P-Value | Up or down regulated in Alzheimer's Disease | ProteinChip ® assay |
| --- | --- | --- | --- |
| M2579.3 | <0.0001 | Down | Fraction 3, WCX, wash with 100 mM Na acetate pH 4 |
| M2986.5 | <0.0001 | Down | Fraction 4, WCX, wash with 100 mM Na acetate pH 4 |
| M3147.2 | <0.0001 | Up | Fraction 3, WCX, wash with 100 mM Na acetate pH 4 |
| M3205.4 | <0.0001 | Down | Fraction 4, WCX, wash with 100 mM Na acetate pH 4 |
| M3258.4 | <0.0001 | Down | Fraction 4, WCX, wash with 100 mM Na acetate pH 4 |
| M3733.3 | <0.0001 | Down | Fraction 4, WCX, wash with 100 mM Na acetate pH 4 |
| M4636.6 | <0.0001 | Up | Fraction 5, WCX, wash with 100 mM Na acetate pH 4 |
| M4934.8 | <0.0001 | Up | Fraction 5, WCX, wash with 100 mM Na acetate pH 4 |
| M5865.3 | <0.0001 | Up | Fraction 4, IMAC, wash with 100 mM Na Phosphate 0.5 M NaCl pH 7 |
| M5974.5 | <0.0001 | Up | Fraction 3, WCX, wash with 100 mM Na acetate pH 4 |
| M6876.4 | <0.0001 | Up | Fraction 4, IMAC, wash with 100 mM Na Phosphate 0.5 M NaCl pH 7 |
| M7466.2 | <0.0001 | Up | Fraction 3, WCX, wash with 100 mM Na acetate pH 4 |
| M7748.6 | <0.0001 | Up | Fraction 4, IMAC, wash with 100 mM Na Phosphate 0.5 M NaCl pH 7 |
| M8295.7 | <0.0001 | Down | Fraction 5, WCX, wash with 100 mM Na acetate pH 4 |
| M8623.2 (C4ades-Arg, SEQ ID NO: 1) | <0.0001 | Up | Fraction 3, WCX, wash with 100 mM Na acetate pH 4 |
| M9758.9 | <0.0001 | Up | Fraction 3, WCX, wash with 100 mM Na acetate pH 4 |
| M9786.8 | <0.0001 | Up | Fraction 3, WCX, wash with 100 mM Na acetate pH 4 |
| M11465.5 | <0.0001 | Up | Fraction 4, WCX, wash with 100 mM Na acetate pH 4 |
| M11498.2 | <0.0001 | Up | Fraction 3, WCX, wash with 100 mM Na acetate pH 4 |
| M11621.2 | <0.0001 | Up | Fraction 3, WCX, wash with 100 mM Na acetate pH 4 |

TABLE I-continued

| Marker | P-Value | Up or down regulated in Alzheimer's Disease | ProteinChip ® assay |
|---|---|---|---|
| M11728.3 (β2 microglobulin) | <0.0001 | Up | Fraction 3, WCX, wash with 100 mM Na acetate pH 4 |
| M11938.4 | <0.0001 | Up | Fraction 3, WCX, wash with 100 mM Na acetate pH 4 |
| M12193 | <0.0001 | Up | Fraction 3, WCX, wash with 100 mM Na acetate pH 4 |
| M13059.2 | <0.0001 | Up | Fraction 3, WCX, wash with 100 mM Na acetate pH 4 |
| M13175.6 | <0.0001 | Up | Fraction 4, WCX, wash with 100 mM Na acetate pH 4 |
| M13212.7 | =0.0001 | Up | Fraction 3, WCX, wash with 100 mM Na acetate pH 4 |
| M15827.5 | <0.0001 | Up | Fraction 3, WCX, wash with 100 mM Na acetate pH 4 |
| M15983.9 | <0.0001 | Up | Fraction 3, WCX, wash with 100 mM Na acetate pH 4 |
| M16037.5 | <0.0001 | Up | Fraction 3, WCX, wash with 100 mM Na acetate pH 4 |
| M44698.7 | <0.0001 | Down | Fraction 3, IMAC, wash with 100 mM Na Phosphate 0.5 M NaCl pH 7 |
| M59127.8 | <0.0001 | Down | Fraction 4, IMAC, wash with 100 mM Na Phosphate 0.5 M NaCl pH 7 |
| M66550.5 (Albumin) | <0.0001 | Down | Fraction 3, WCX, wash with 100 mM Na acetate pH 4 |

The identity of biomarkers were determined as follows. Proteins were separated on an acrylamide gel and a band containing the biomarker was cut out of the gel. The protein in the band was destained. The gel was dried using acetonitrile and then subject to digestion in a solution of trypsin. The digest fragments were analyzed on a Ciphergen PBSII mass spectrometer. The determined masses were used to interrogate a protein database, which identified the protein having the same tryptic digest pattern. All of these identifications were further confirmed by tandem MS analysis. Finally, the identity of 0-microglobulin was determined by antibody capture. Antibodies were bound to Ciphergen PS20 ProteinChip arrays, which have reactive epoxide surfaces. Sample containing the biomarker was applied to the antibody spot. Unbound proteins were removed and the arrays were read with a Ciphergen PBSII reader. The detection of a protein having the mass of the target confirmed identity.

The identity of M8623.24 was found to be the C4ades-Arg protein, which is a cleavage product of anaphylatoxin C4a. Anaphylatoxin C4a is a biologically active fragment of Complement C4 (Swiss-Prot accession number P01028 http://us.expasy.org/cgi-bin/niceprot.pl?P01028). In serum as well as CSF, the carboxypeptidase N rapidly cleaves off the C-terminal arginine, thereby generating the relatively stable protein C4ades-Arg. The amino acid sequence of C4ades-Arg was determined by direct sequencing. The amino acid sequence of C4ades-Arg is as follows:

NVNFQKAINEKLGQYASPTAKRC-CQDGVTRLPMMRSCEQRAARVQQ PDCREP-FLSCCQFAESLRKKSRDKGQAGLQ (SEQ ID NO:1) (theoretical MW is 8607.88 Da).

In immunoassay experiments, it was found that an antibody against human C4ades-Arg, i.e., an affinity-purified anti-C4ades-Arg antibody, specifically pulls down the 8607 Da protein from CSF.

Example 2

Validation Study of B2 Microglobulin as a Marker for Alzheimer's Disease

To validate the use of β2 microglobulin as a marker for Alzheimer's disease, 158 cerebrospinal fluid (CSF) samples were taken from pre-diagnosed subjects in three groups: (1) Alzheimer's disease (AD), (2) Control, and (3) non-Alzheimer's dementia (Non AD). The distribution of samples in these groups is shown in Table III, below.

TABLE III

Distribution of Subjects in β2 Microglobulin Validation Study

| Subject Classification | | # of Subjects |
|---|---|---|
| Alzheimer's Disease | AD Mild (MMSE > 24) | 56 |
| | AD severe | 10 |
| Control | Depression | 6 |
| | Control | 45 |
| Non-Alzheimer's Dementia | FTD | 21 |
| | LBD | 20 |
| Total | | 158 |

Briefly, of the 158 samples, sixty six were taken from patients suffering from mild forms of Alzheimer's disease (characterized by a Mini-Mental State Examination (MMSE) score greater than twenty four) or suffering from more severe forms of Alzheimer's disease. Fifty one "control" samples were obtained from non-dementia patients, including six patients diagnosed as "depressed." Samples taken from forty one patients suffering from non-Alzheimer's dementia included twenty samples taken from patients suffering from Lewy body dementia (LBD) and twenty one samples taken from patients suffering from frontotemporal dementia (FTD).

SELDI-MS measurements of β2 microglobulin in each of the samples were obtained using a Ciphergen H50 Protein-Chip according to the following binding protocol, using 50% SPA as an EAM for reading the chip:

Bulk Wash H50 arrays in 50% acetonitrile for 30 minutes and then air dry for 30 minutes.

Add 100 μL of Binding buffer (10% Acetonitrile+0.1% Trifluoroacetic acid) into each well Shake 5 min at Room Temperature (RT)

Remove buffer after shaking

Add 100 μL of Binding buffer into each well

Shake 5 min at Room Temperature (RT)

Remove buffer after shaking

Add 45 μl of Binding buffer into each well

Add 5 μl of neat CSF sample

Shake 30 min at Room Temperature (RT)

Remove sample buffer after shaking

Add 100 μL of Binding buffer into each well

Shake 5 min at Room Temperature (RT)

Remove buffer after shaking

Add 100 μL of Binding buffer into each well

Shake 5 min at Room Temperature (RT)

Remove buffer after shaking

Add 1 μl 50% SPA (sinapinic acid) in 50% Acetonitrile and 0.5% TFA

Air dry
Add 1 µl 50% SPA
Air dry
Analyze arrays.

Figure 3:
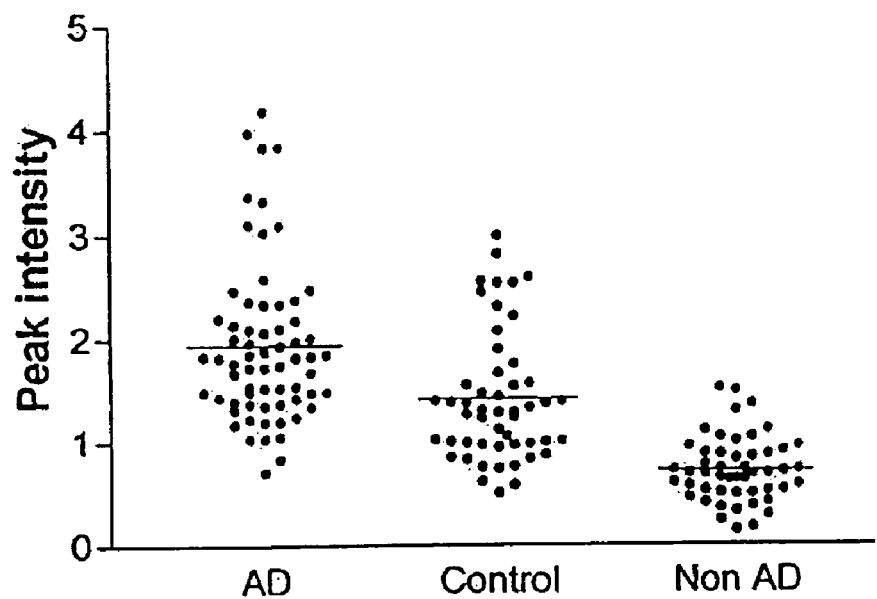
FIG. 3 shows the results of statistical tests used to validate the measurement of $\beta 2$ microglobulin in CSF as a means for distinguishing between patients suffering from Alzheimer's disease ("AD") versus non-Alzheimer's dementia ("non AD") and versus patients who are not showing symptoms of dementia ("Control"). In particular, the data indicates a statistically significant difference in the average peak intensities of $\beta 2$ microglobulin between Alzheimer's patients and the control group ("A-C"); between Alzheimer's patients and patients with non-Alzheimer's dementia ("A-N"); and between patients with non-Alzheimer's dementia and the control group ("C-N"). Measurements of peak intensities were performed as described in the Examples, utilizing the Ciphergen H50 ProteinChip.
Figure 4A:
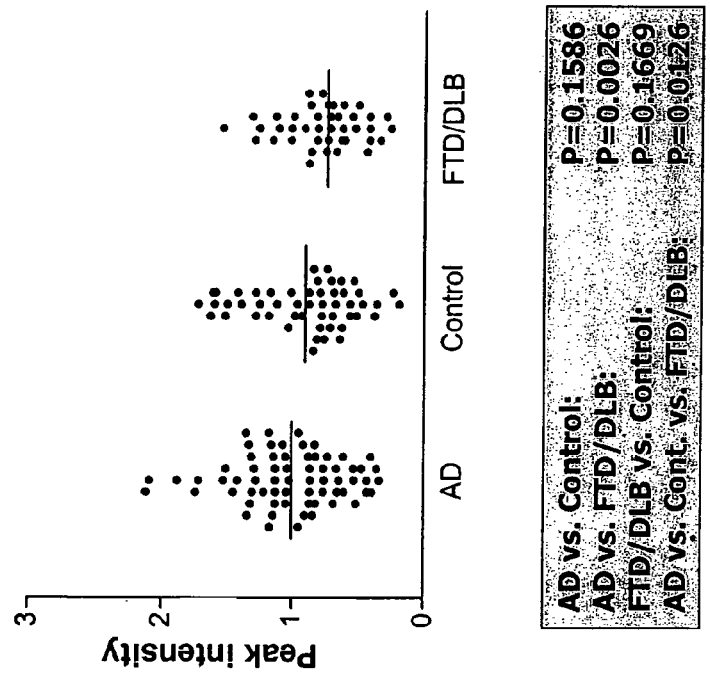
Figure 4B:
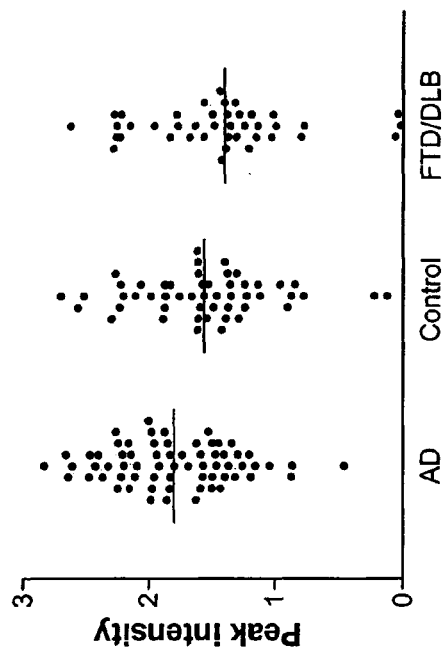
Figure 4B:
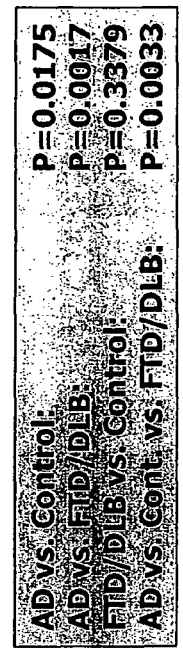
Figure 4B:
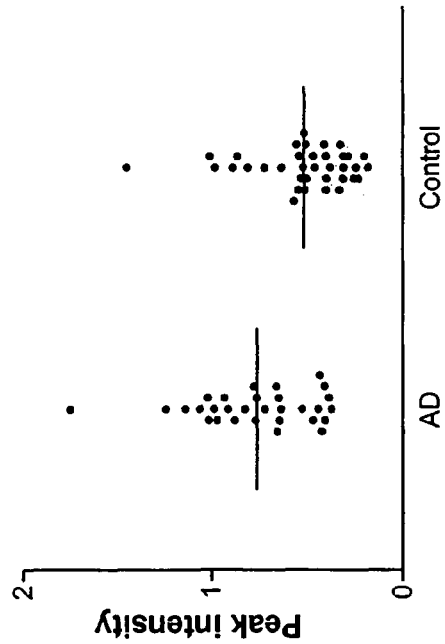
Figure 4C:
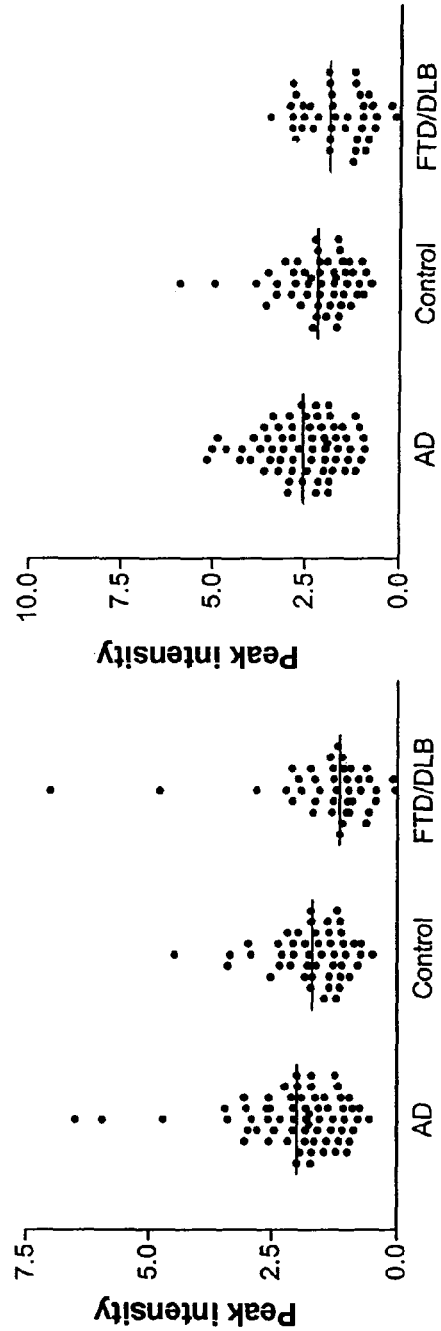
Figure 4D:
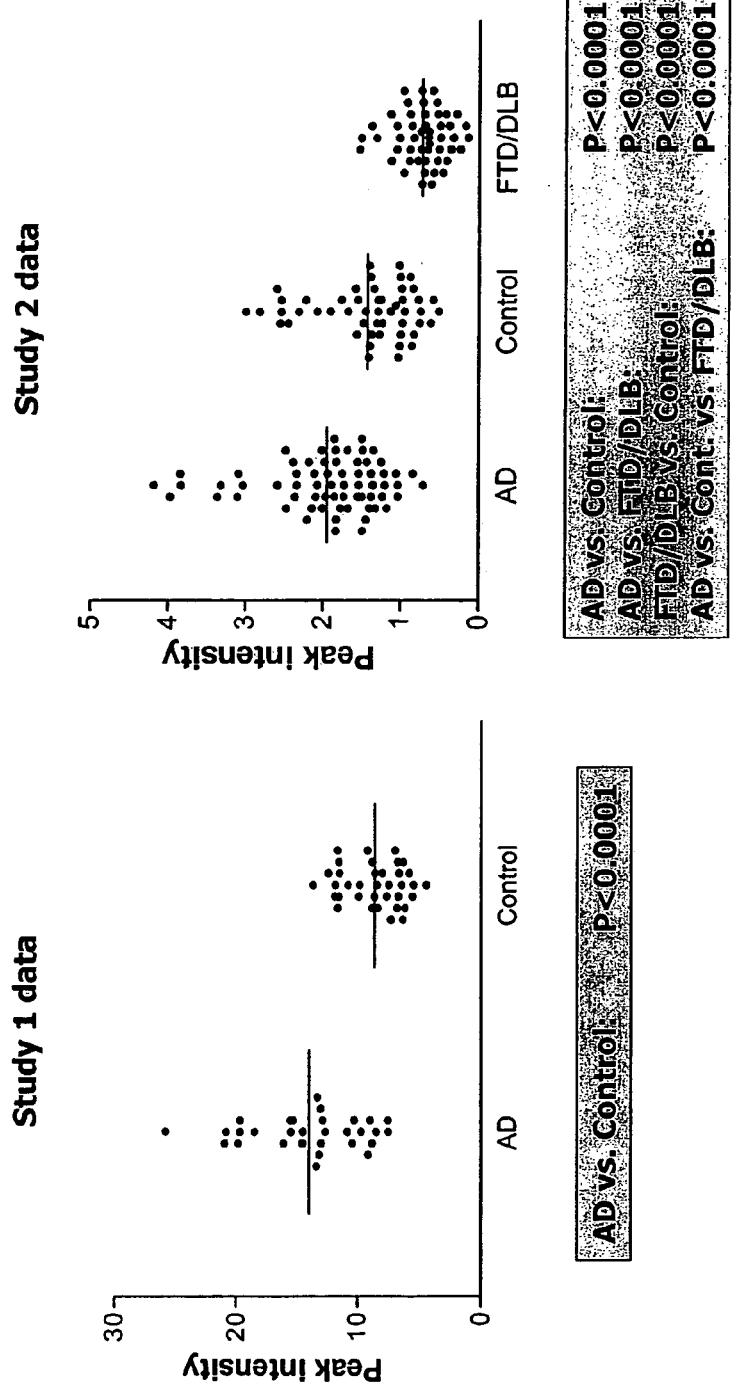
Figure 4F:
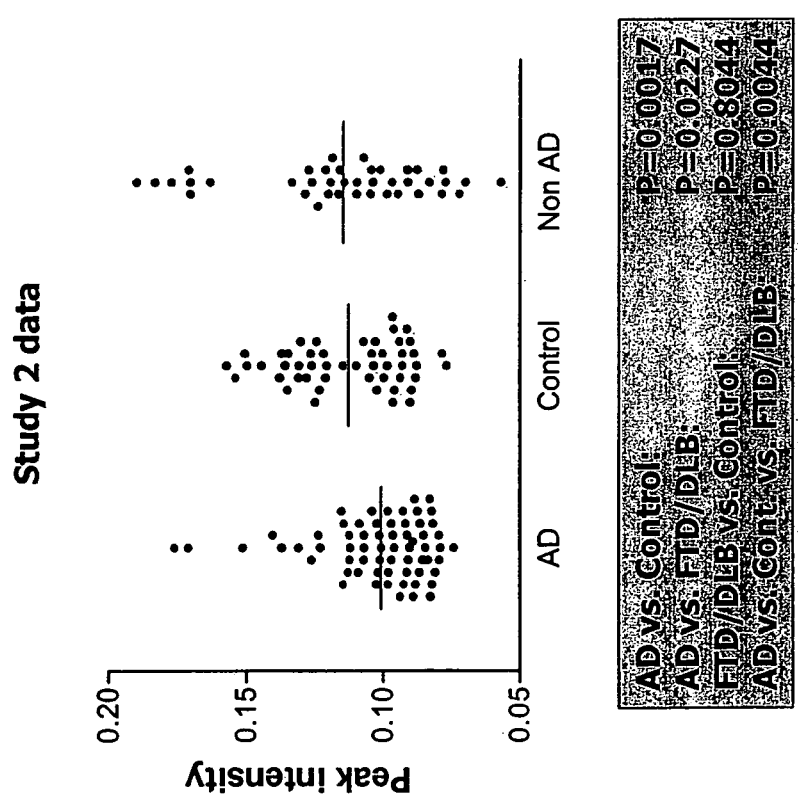
Figure 4G:
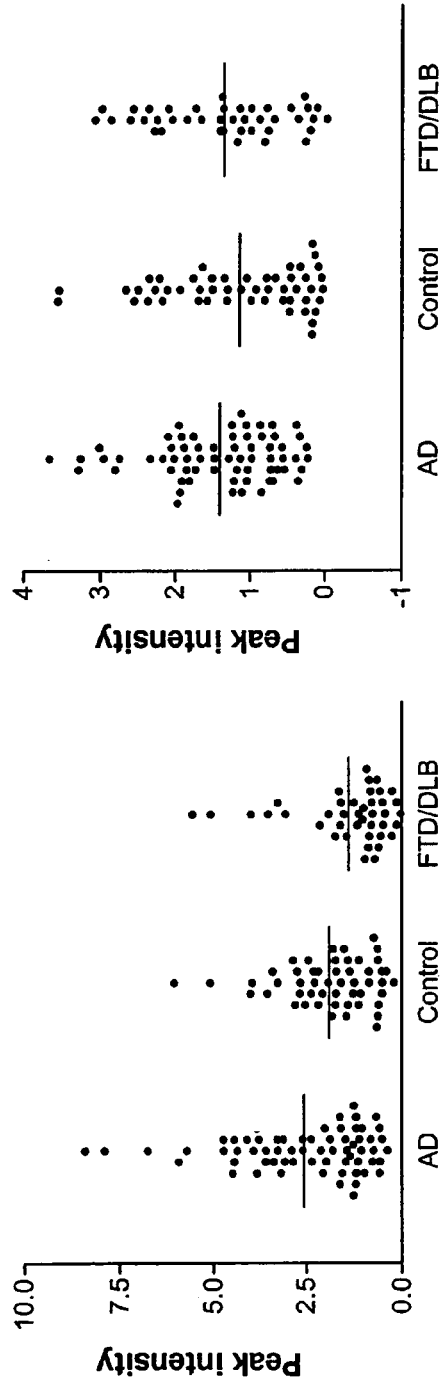
Figure 4H:
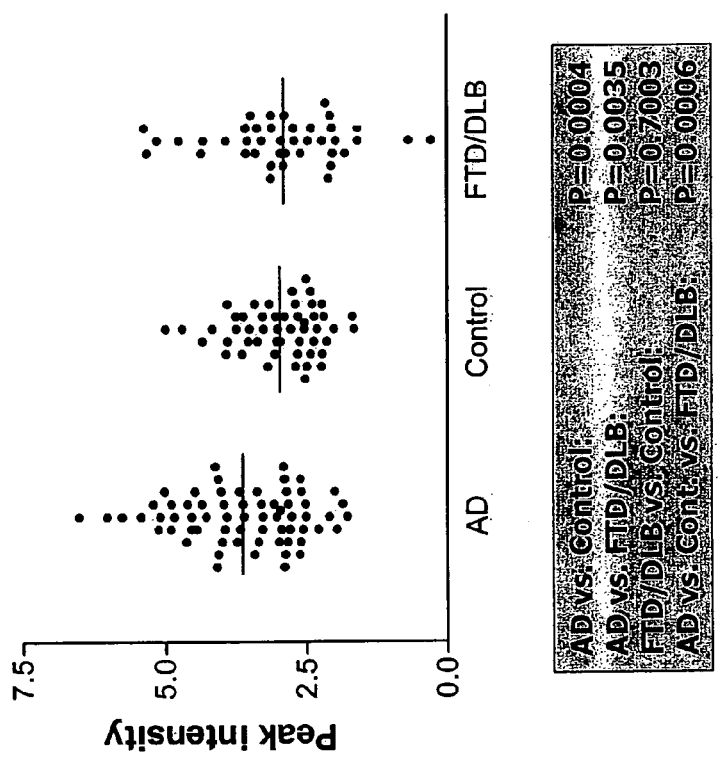
Figure 4I:
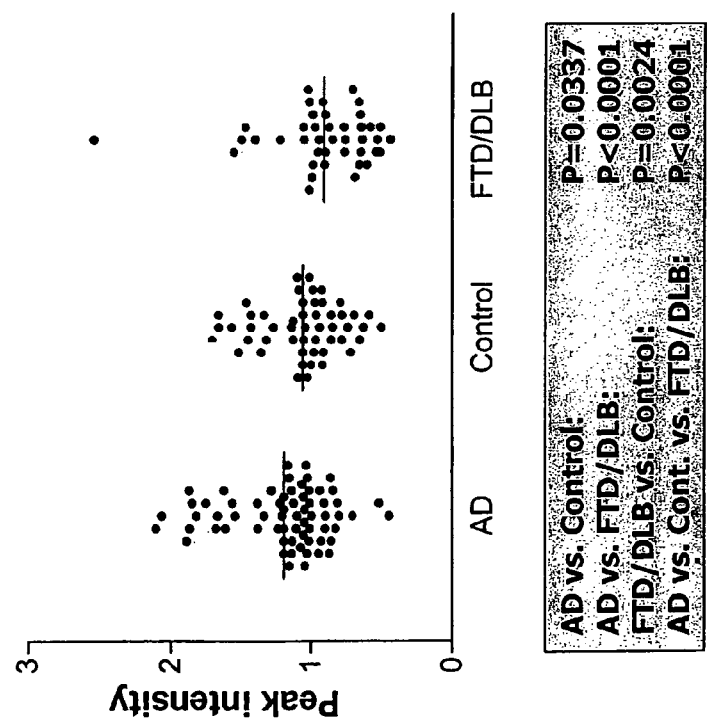
Figure 4J:
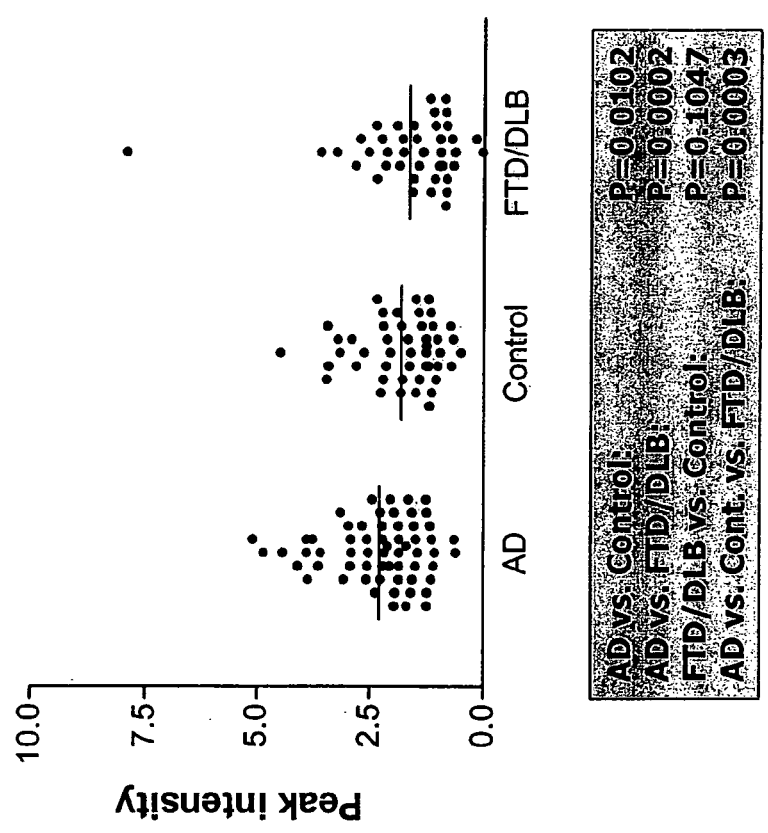
Figure 4K:
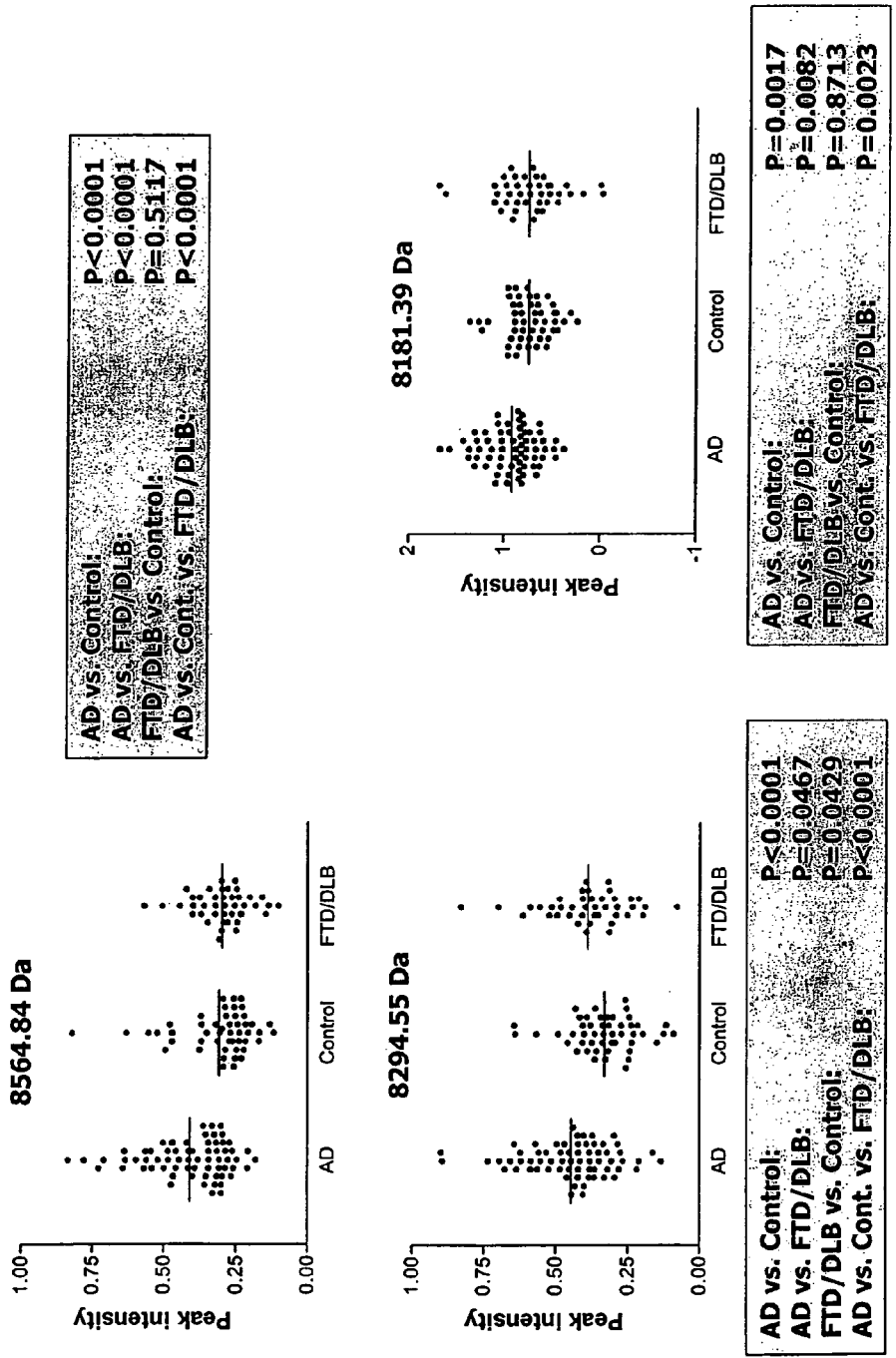
Figure 5:
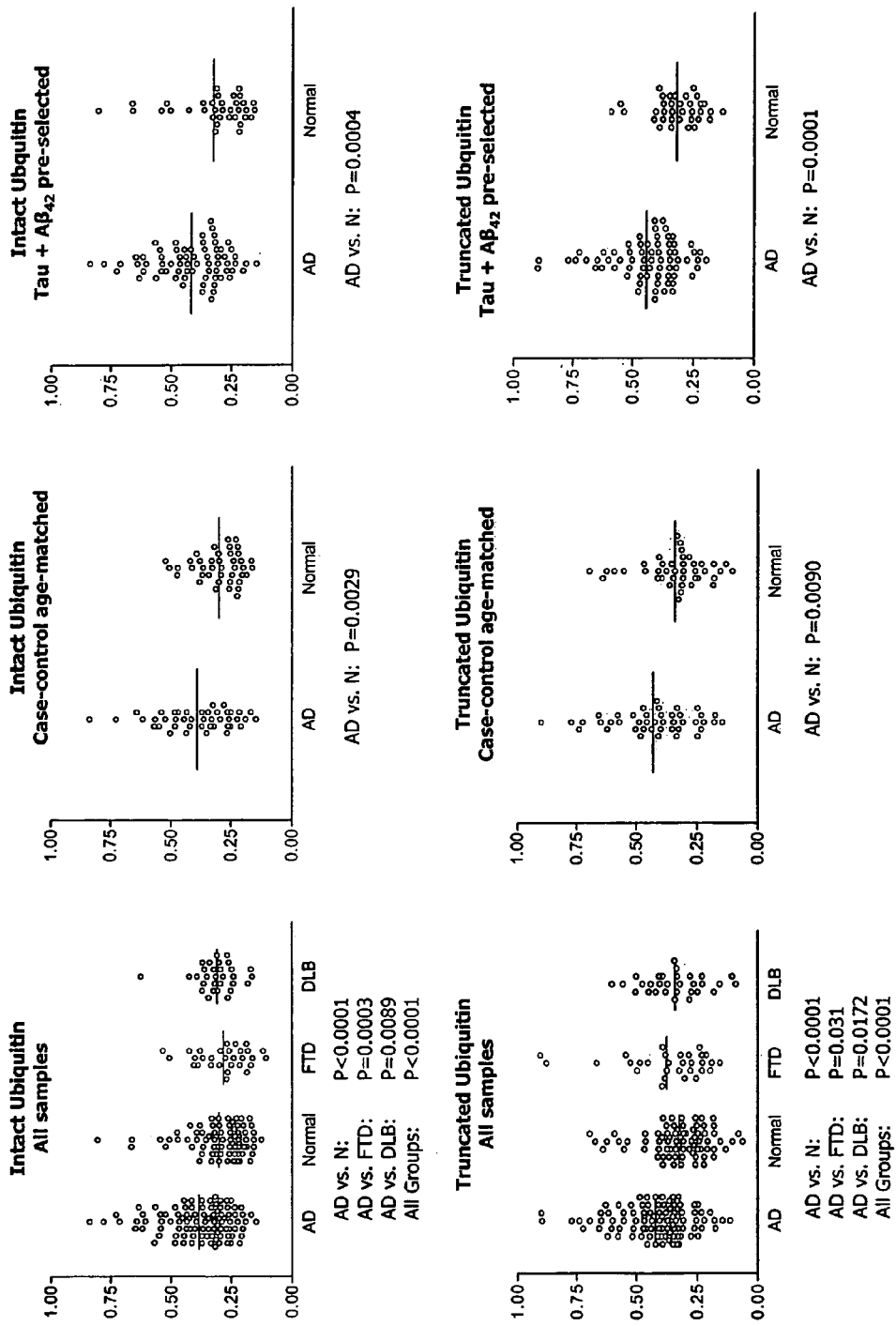
FIG. 5 shows the distribution of peak intensities observed for full-length and truncated ubiquitin biomarkers, and the results of Mann-Whitney or Kruskal-Wallis tests used to determine the significance of any differences observed. Results are also presented for comparisons between disease and control groups using age-matched samples and using samples restricted by specific Tau/AB42 cut-off levels.
Figure 6:
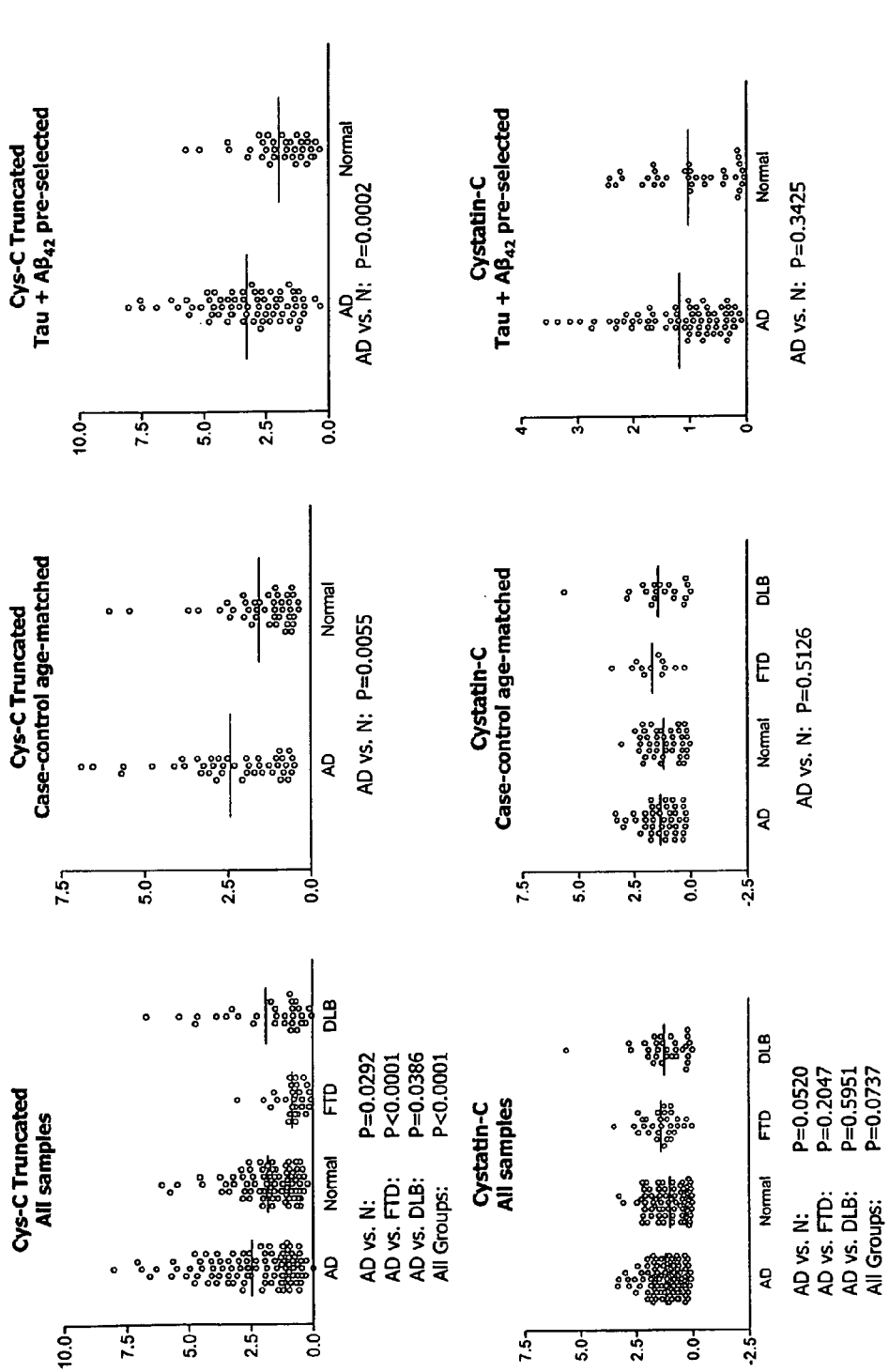
FIG. 6 shows the distribution of peak intensities observed for full-length and truncated Cystatin C biomarkers and the results of Mann-Whitney or Kruskal-Wallis tests used to determine the significance of any differences observed. Results are also presented for comparisons between disease and control groups using age-matched samples and using samples restricted by specific Tau/AB42 cut-off levels.
Figure 7:
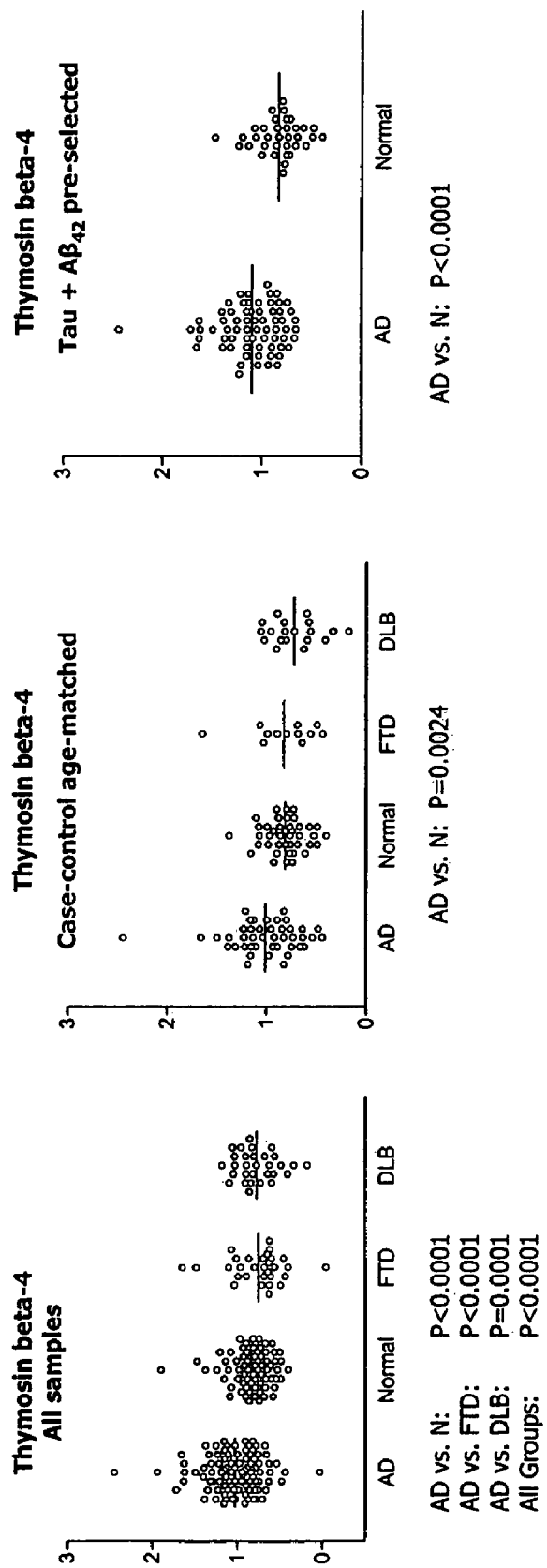
FIG. 7 shows the distribution of peak intensities observed for the Thymosin beta-4 biomarker and the results of Mann-Whitney or Kruskal-Wallis tests used to determine the significance of any differences observed. Results are also presented for comparisons between disease and control groups using age-matched samples and using samples restricted by specific Tau/AB42 cut-off levels.
Figure 8:
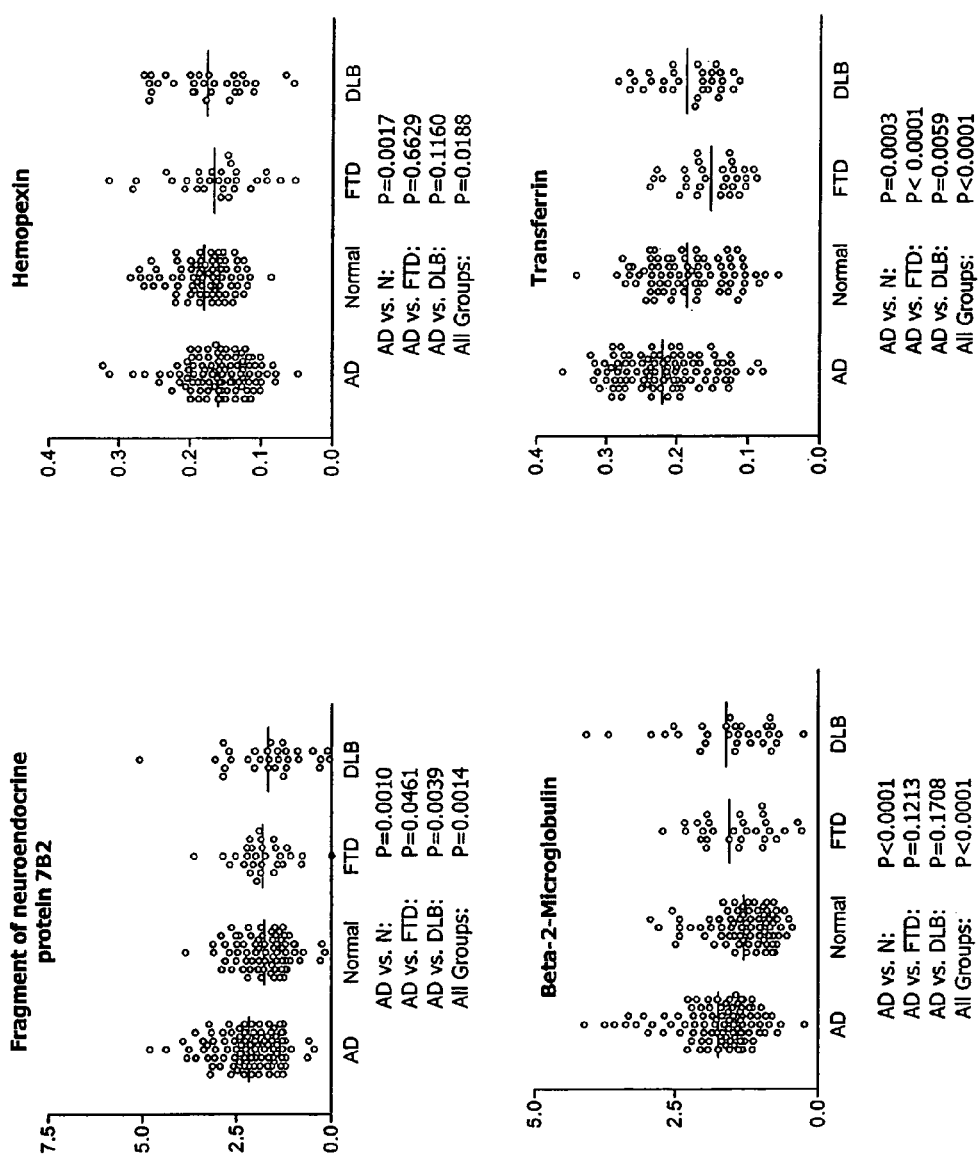
FIG. 8 shows the distribution of peak intensities observed for the neuroendocrine protein 7B2, hemopexin, beta-2-microglobulin and transferrin biomarkers.
Figure 9A:
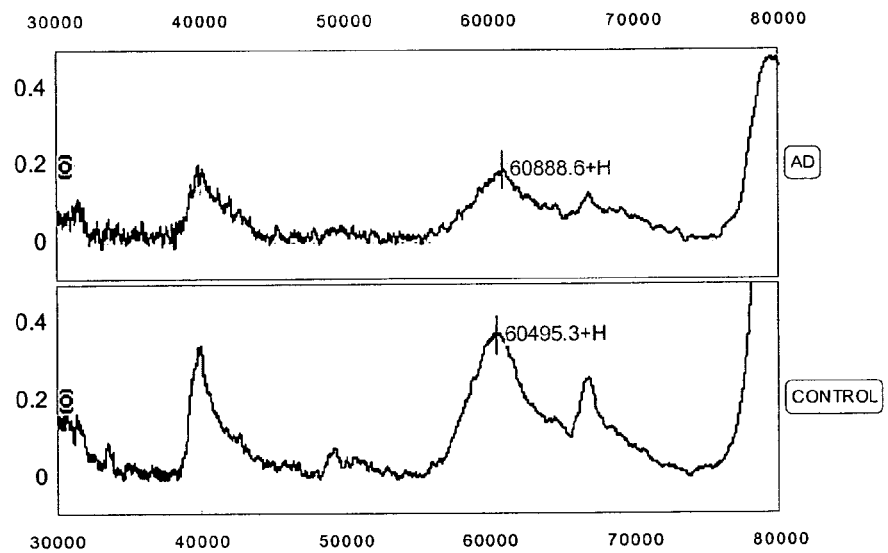
FIG. 9 shows mass spectra displaying biomarkers identified according to the techniques described in Example 3, utilizing neat CSF samples.
Figure 9B:
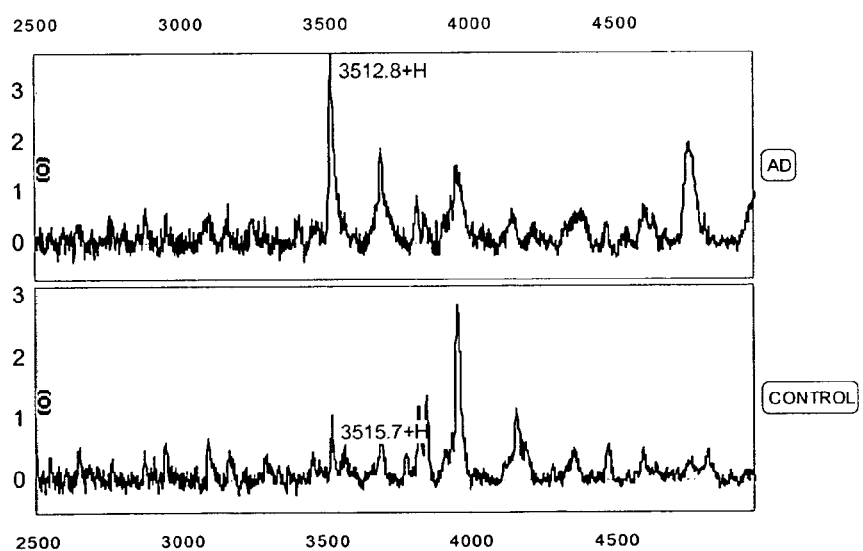
Figure 9C:
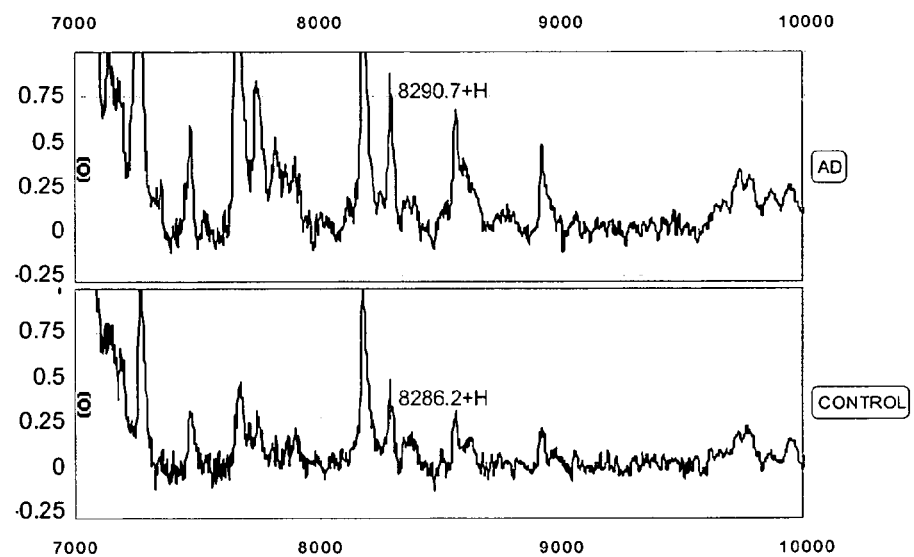
Figure 9D:
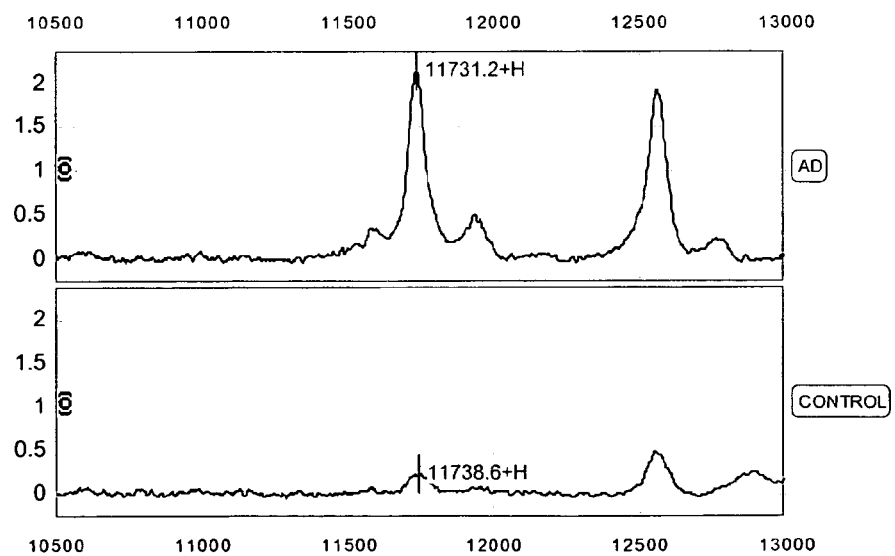
Figure 9E:
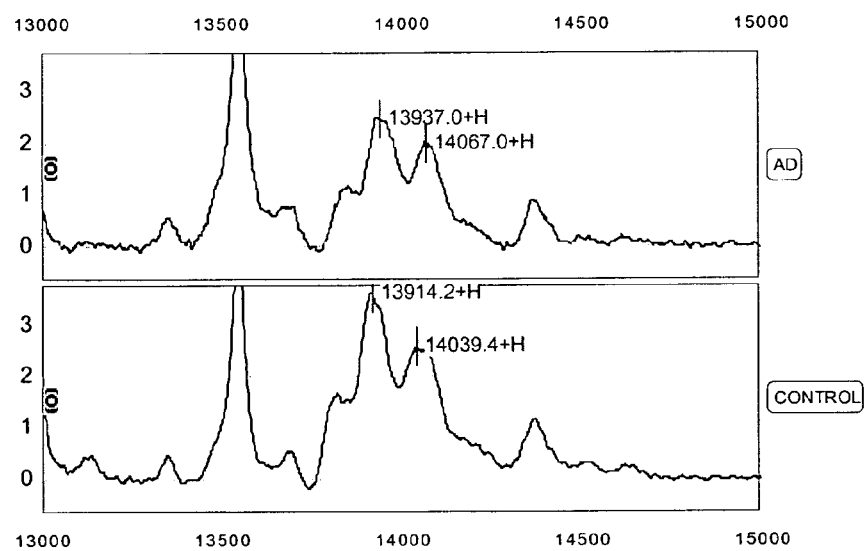
Figure 9F:
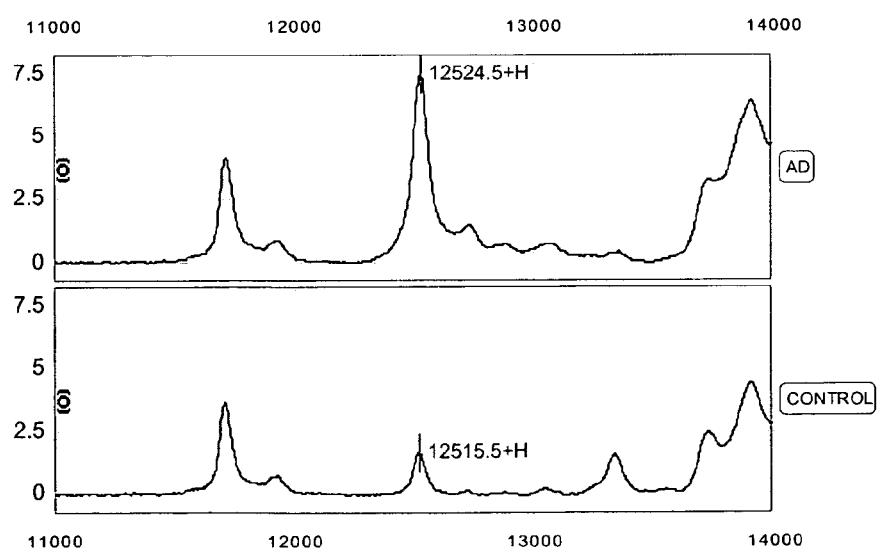
Figure 9G:
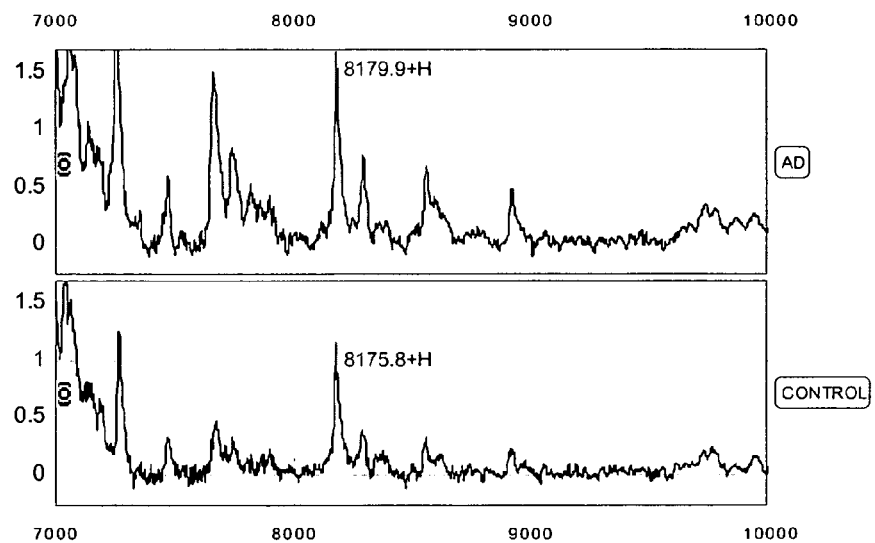
Figure 9H:
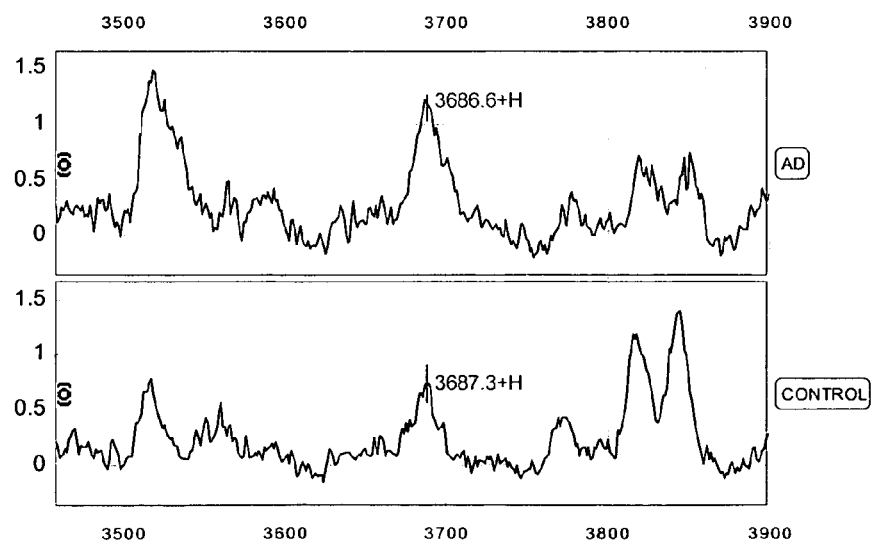
Figure 9I:
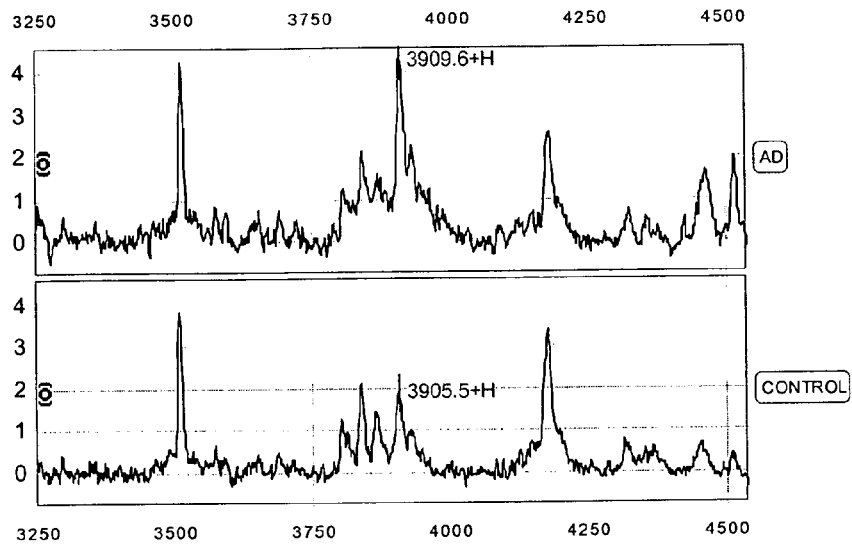
Figure 9J:
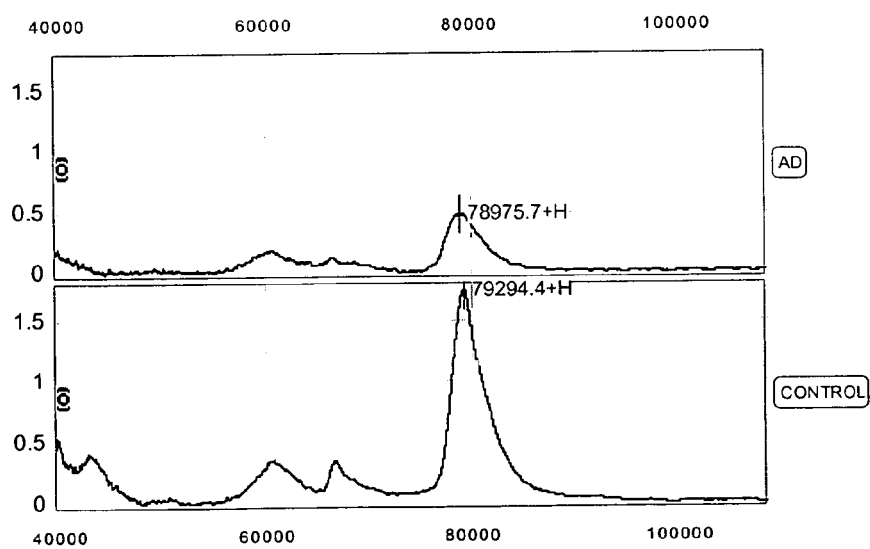
Figure 9K:
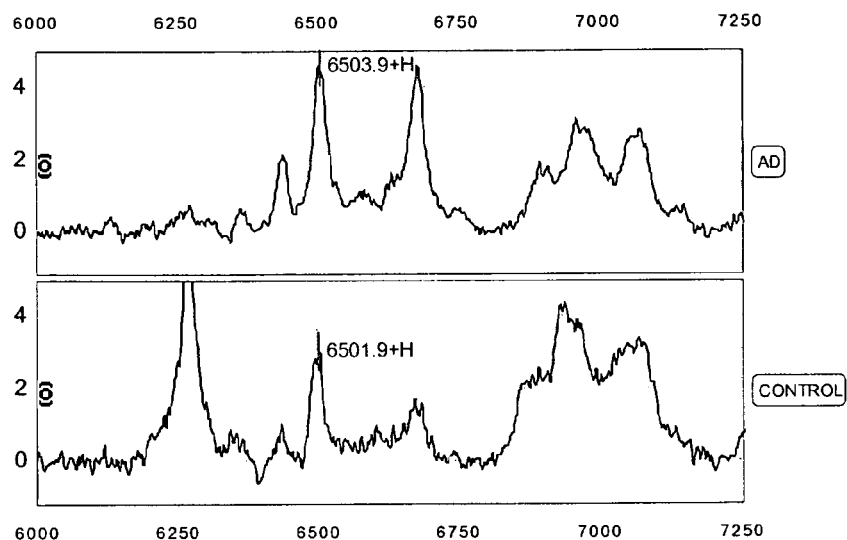
Figure 9L:
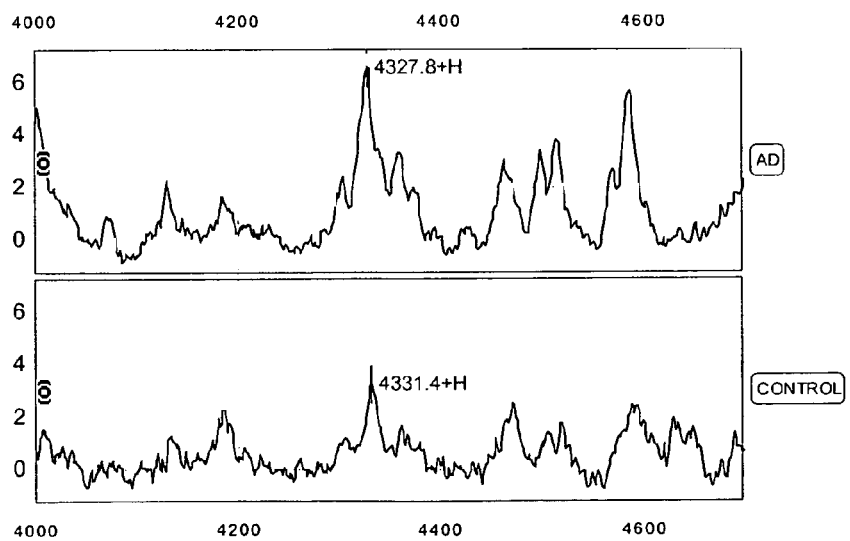
Figure 9M:
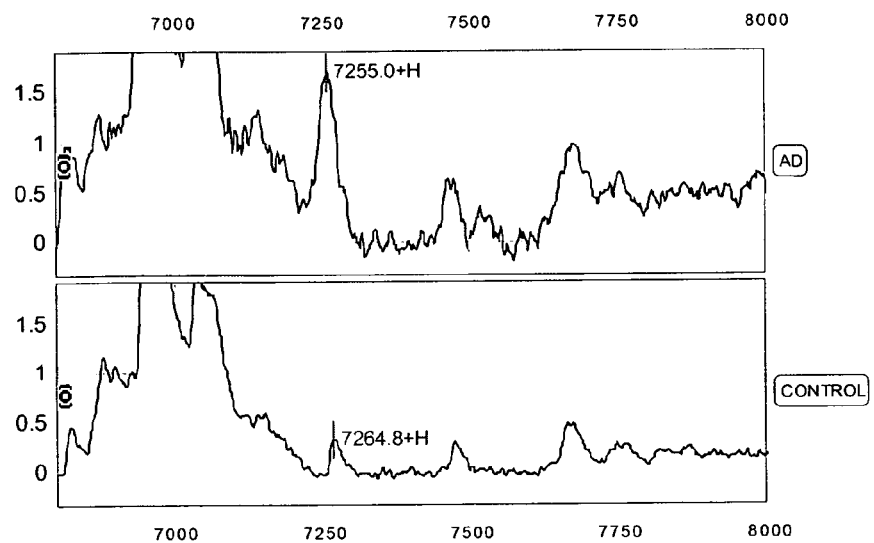
Figure 9N:
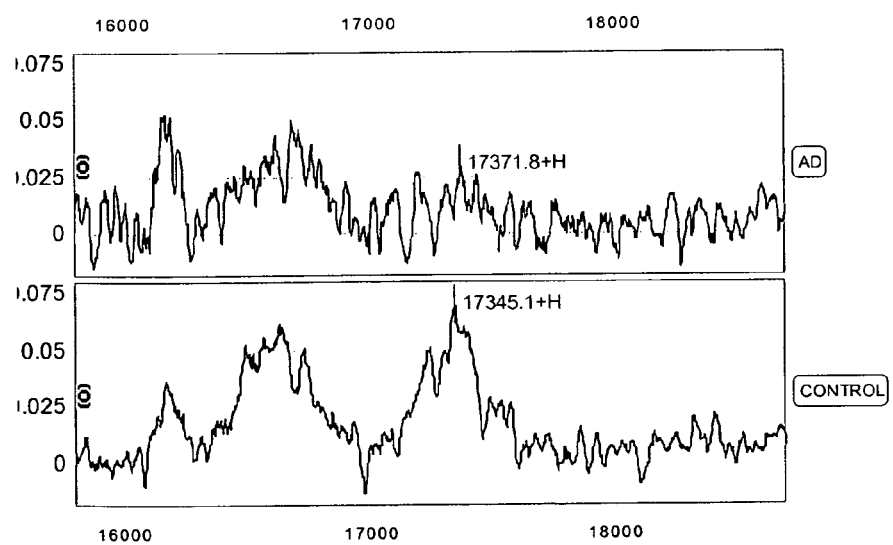
Figure 9O:
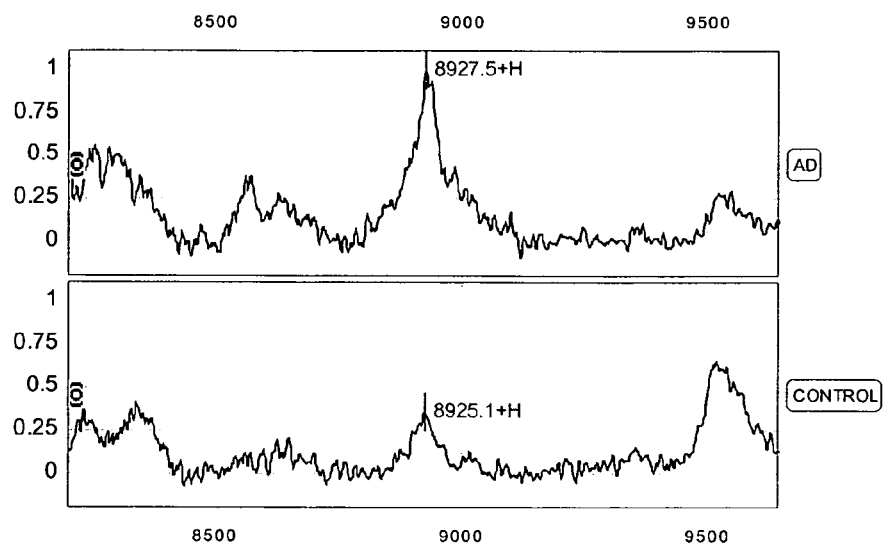
Figure 9P:
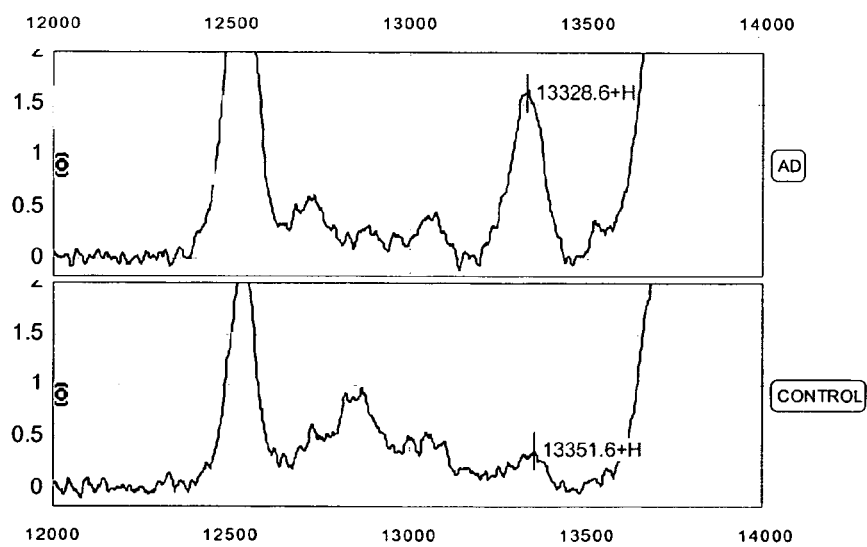
Figure 9Q:
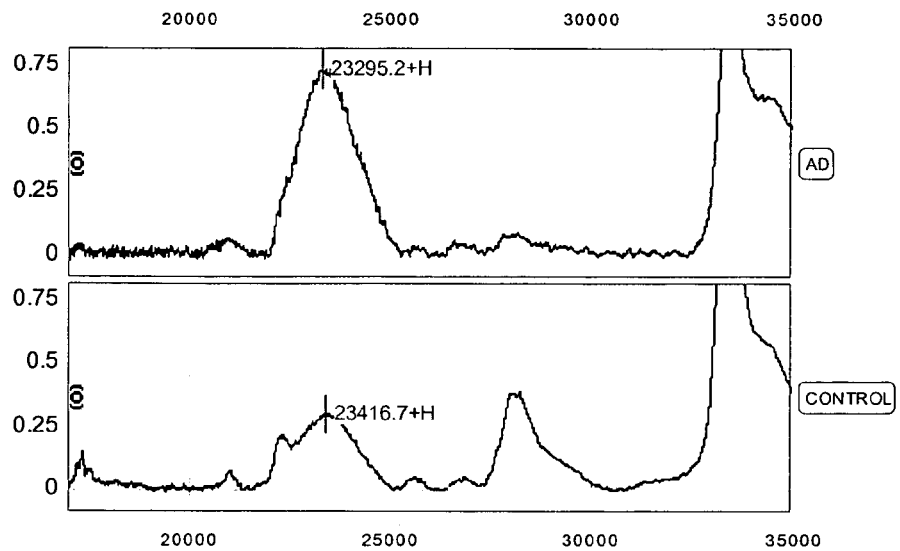
Figure 9R:
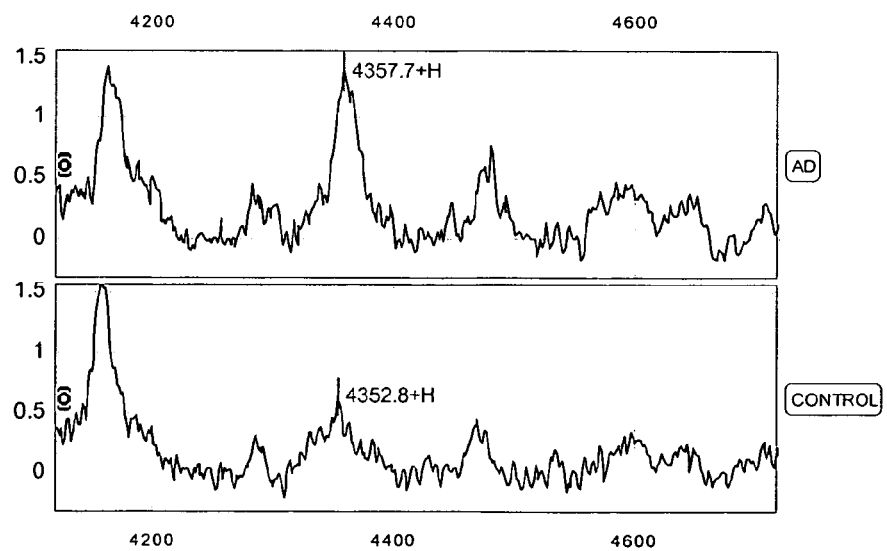
Figure 9S:
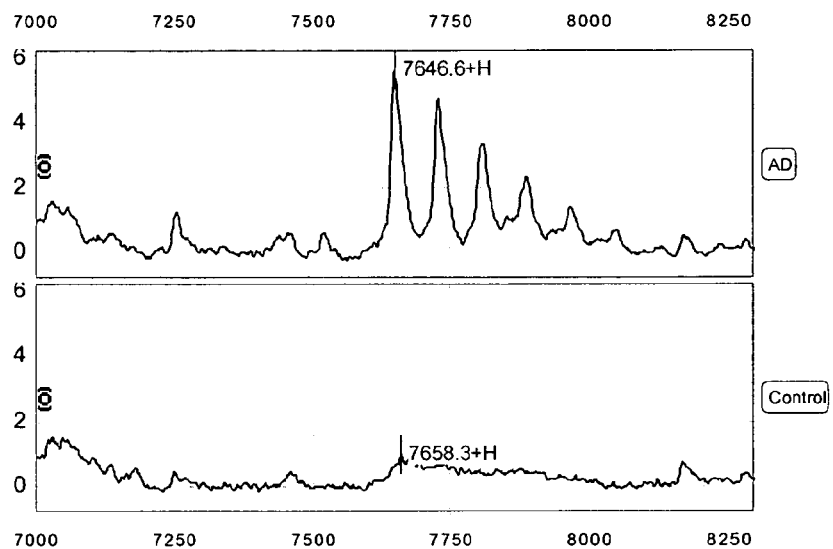
Figure 9T:
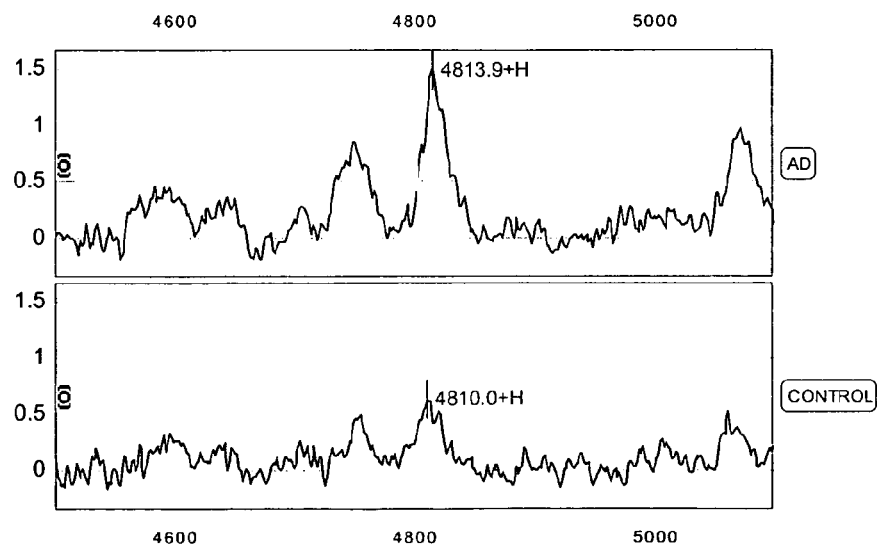
Figure 9U:
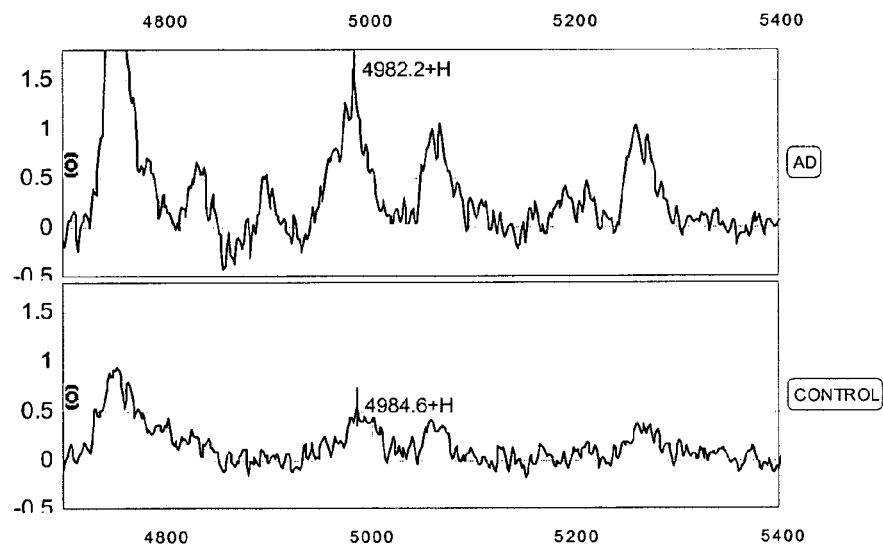
Figure 9V:
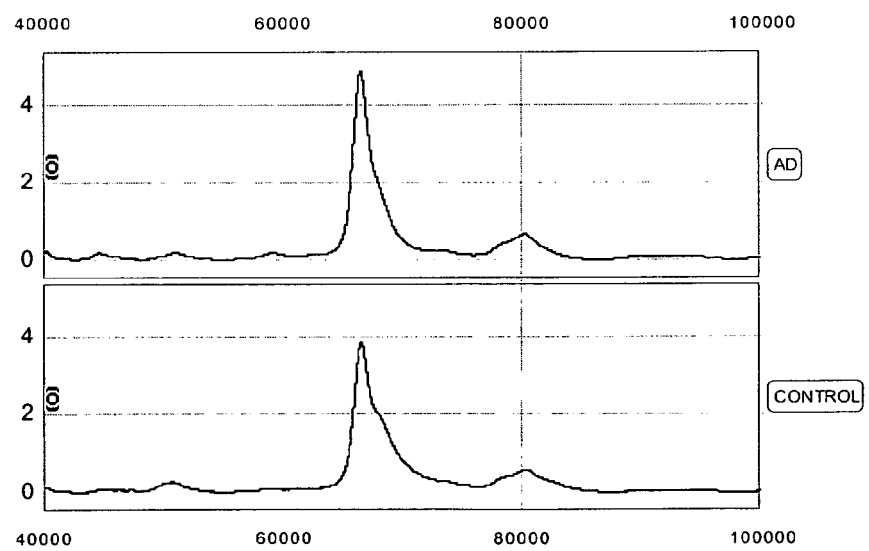
Figure 9W:
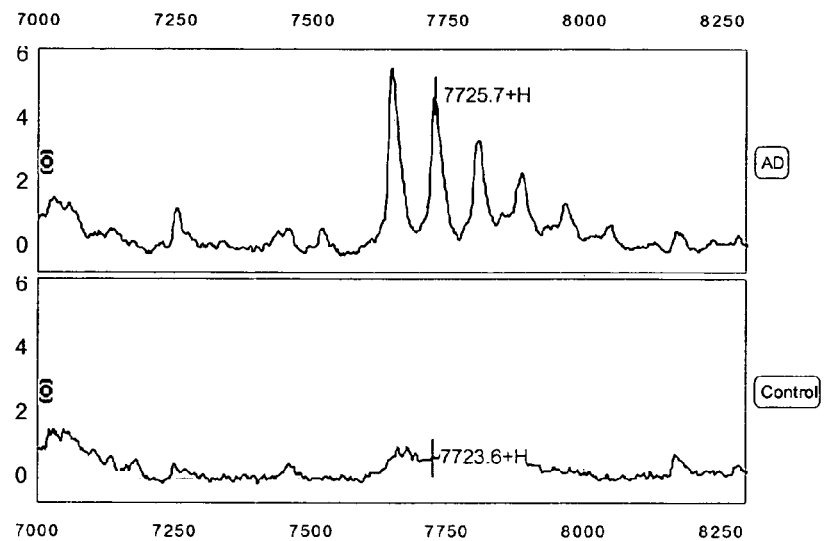
Figure 9X:
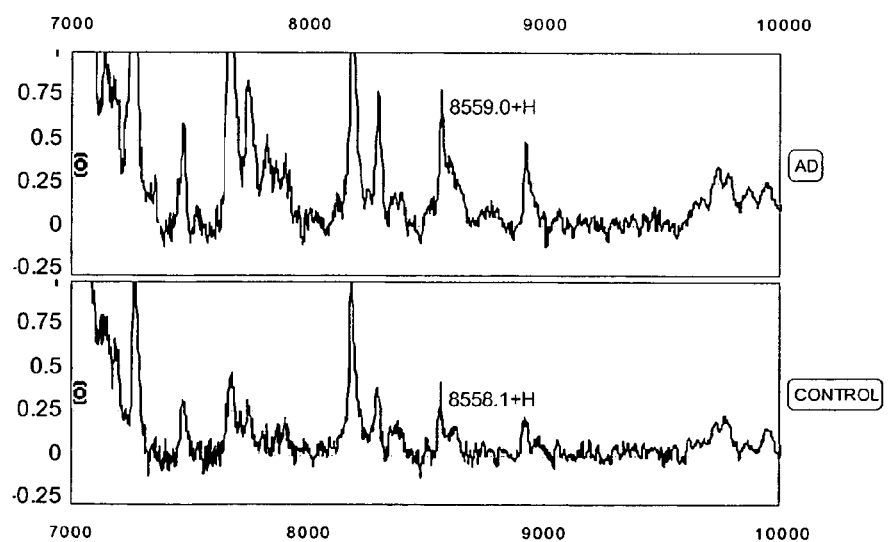
Figure 9Y:
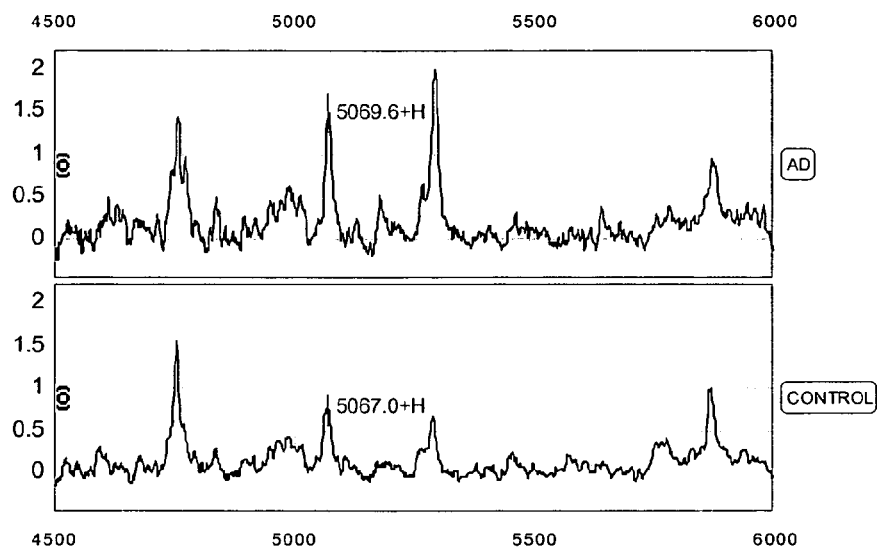
Figure 9Z:
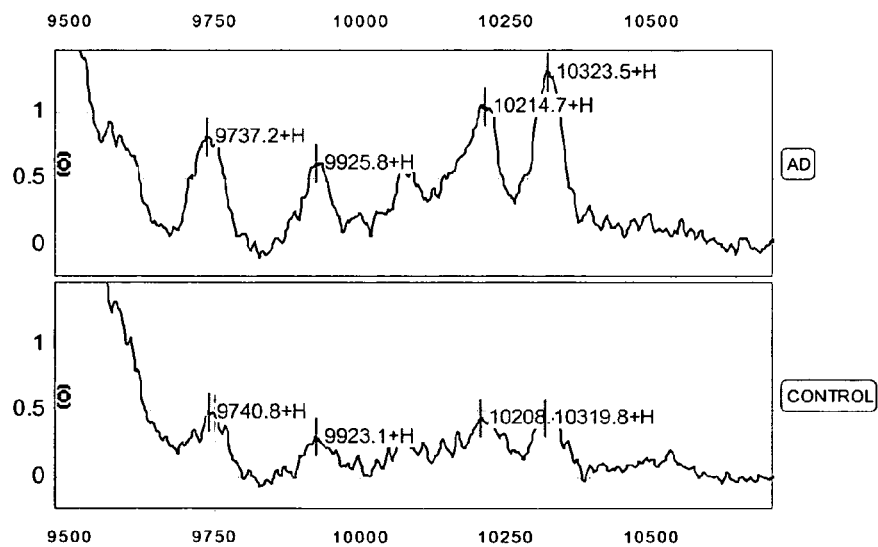
Figure 9A:
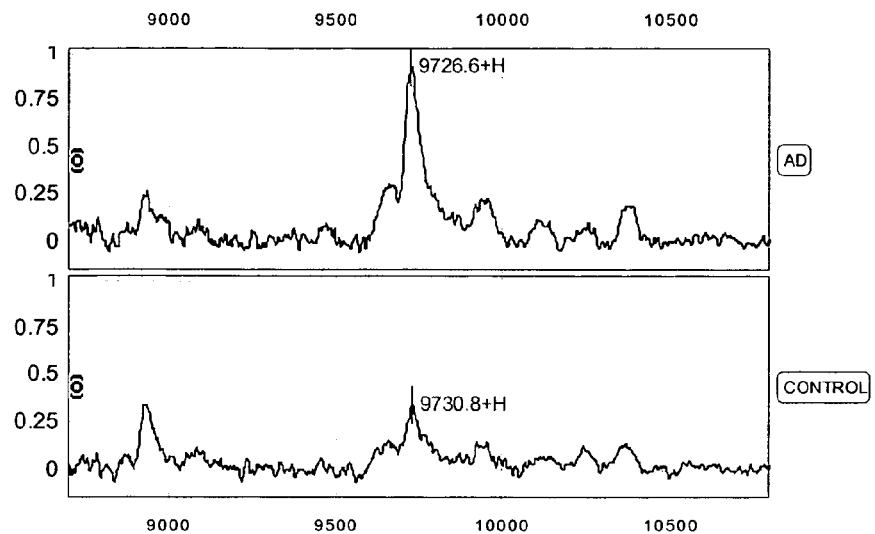
Figure 9B:
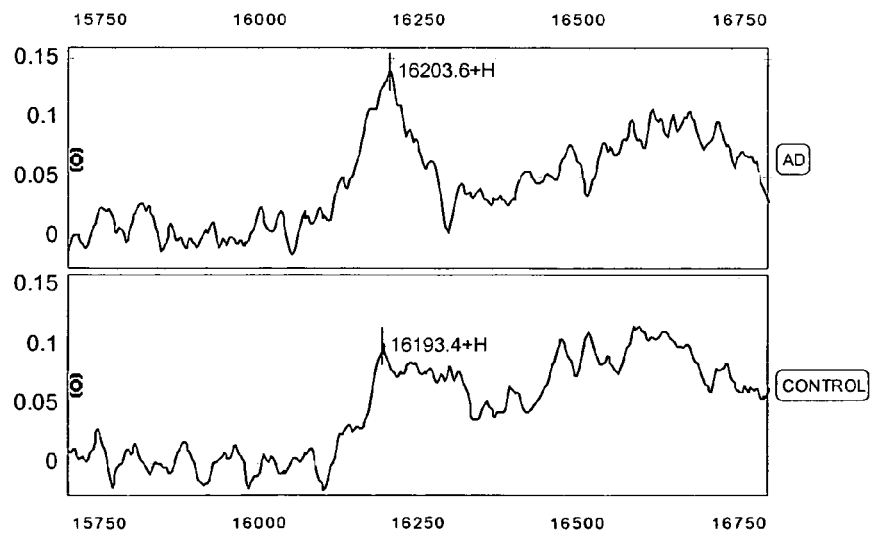
Figure 9C:
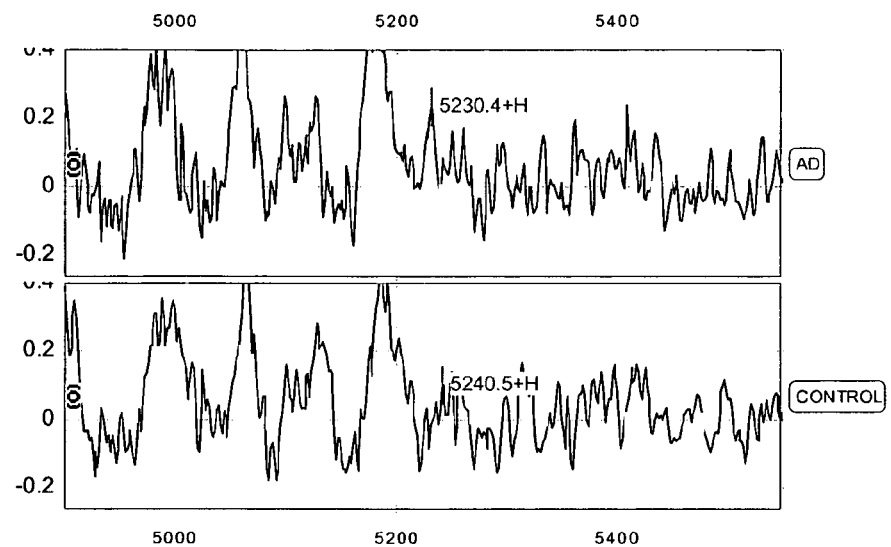
Figure 9D:
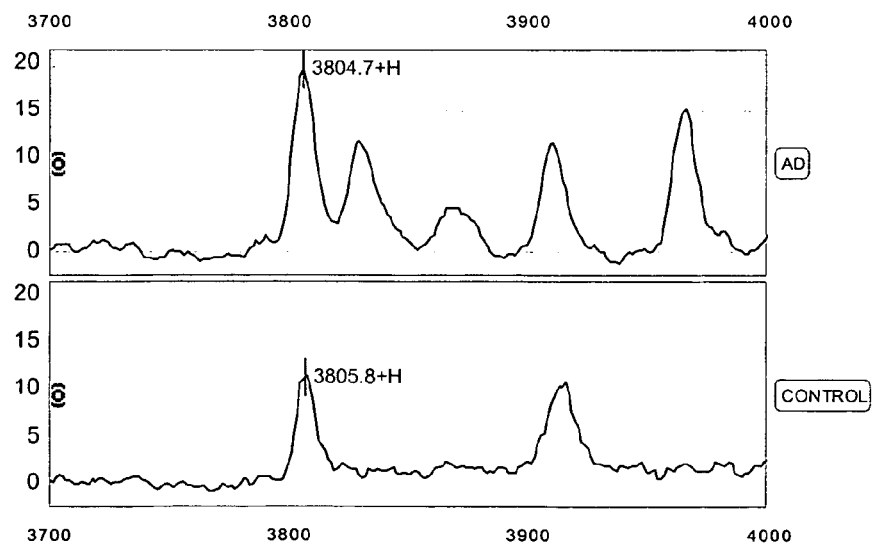
Figure 9E:
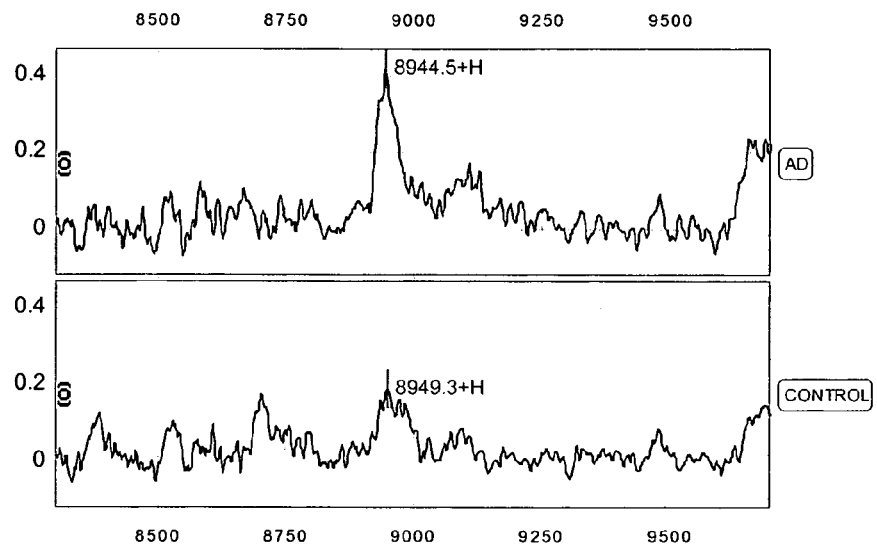
Figure 9F:
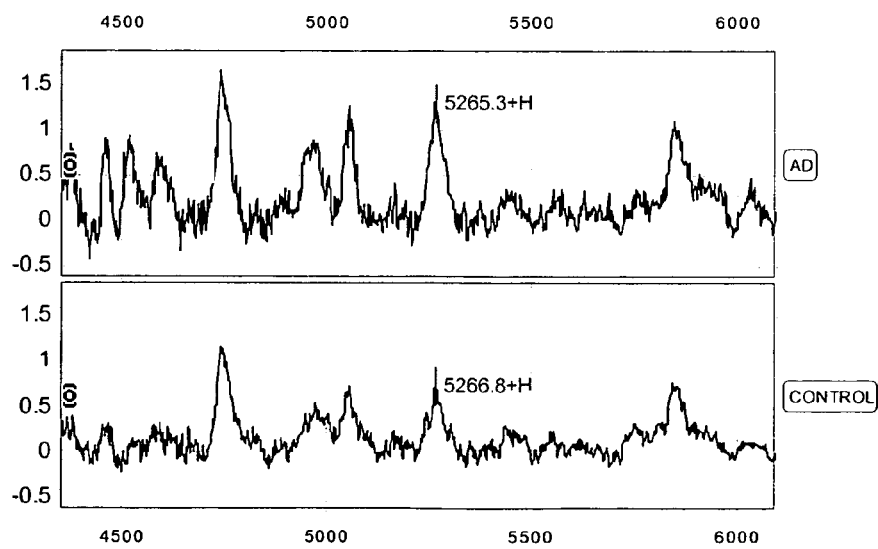
Figure 9G:
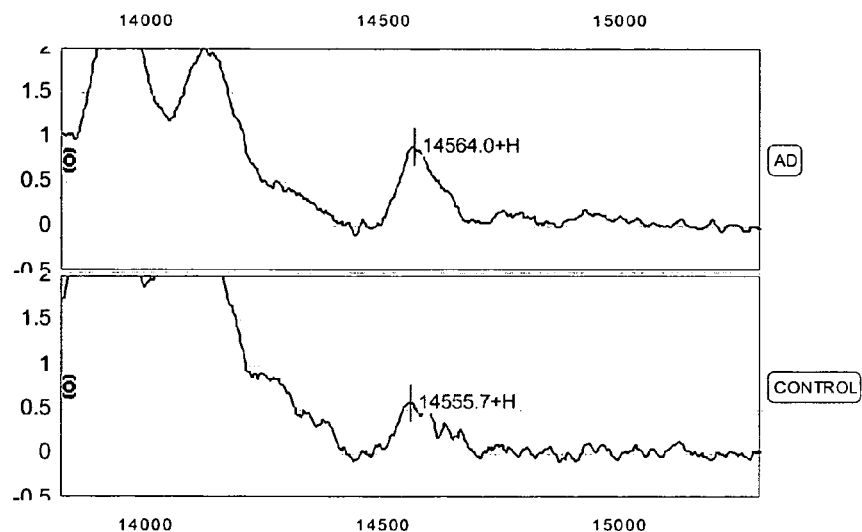
Figure 9H:
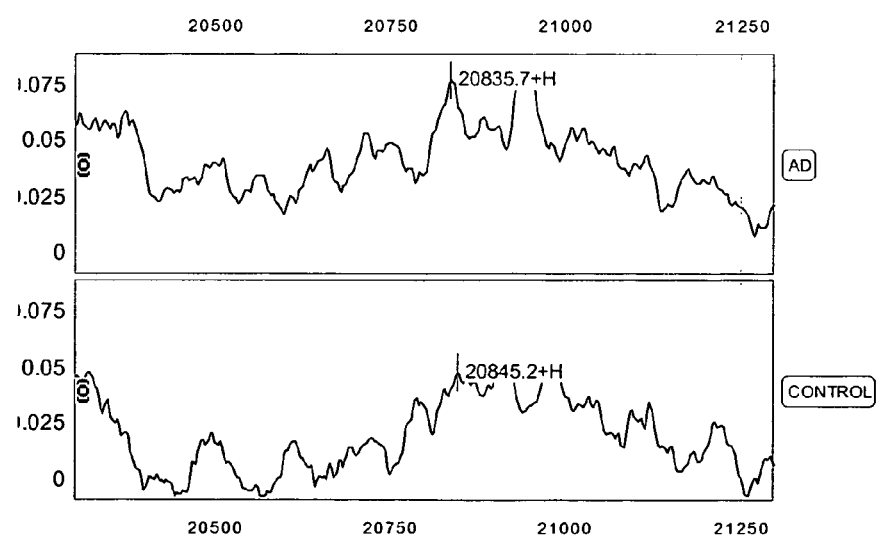
Figure 9I:
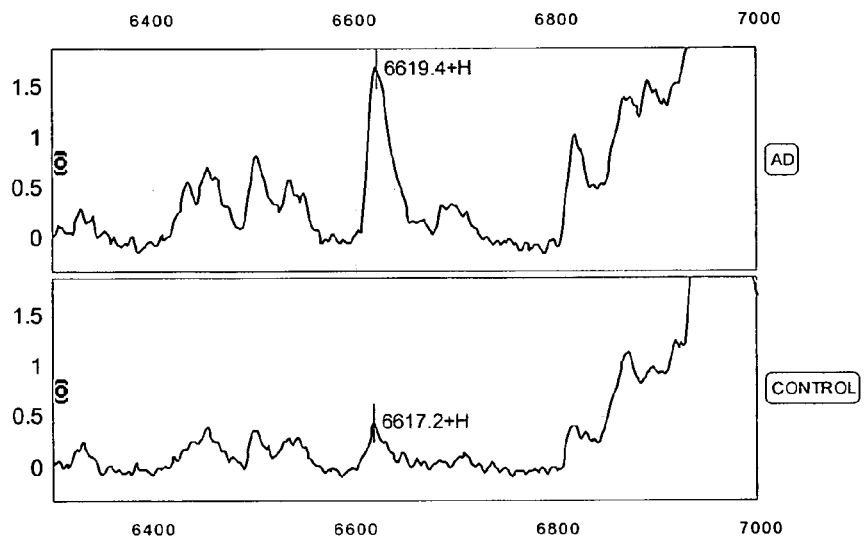
Figure 9J:
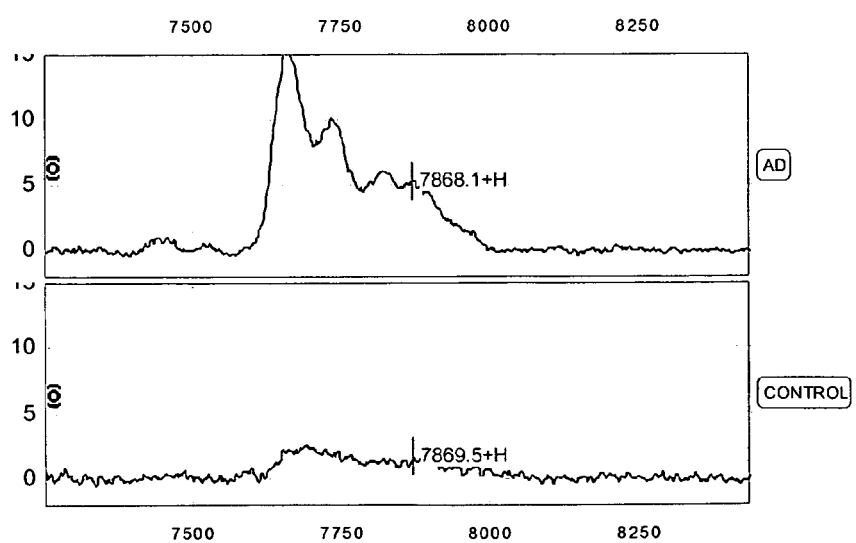
Figure 9K:
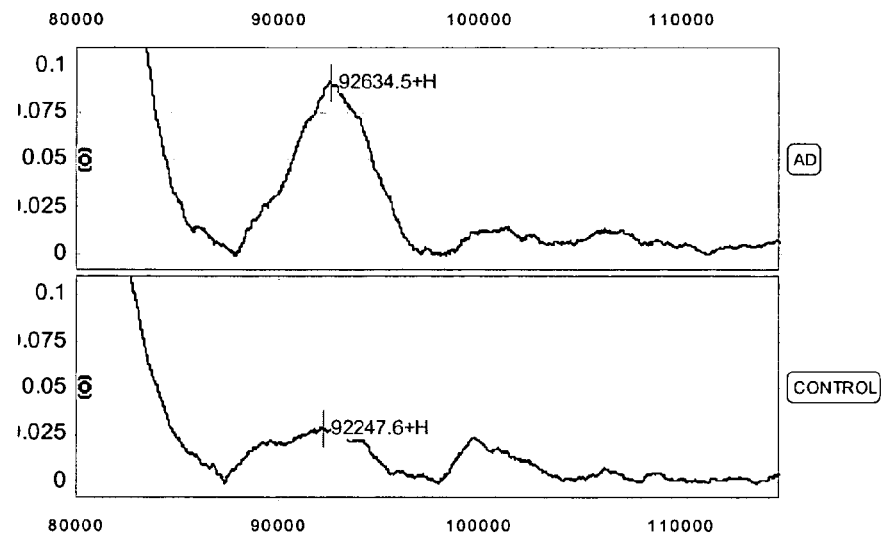
Figure 9L:
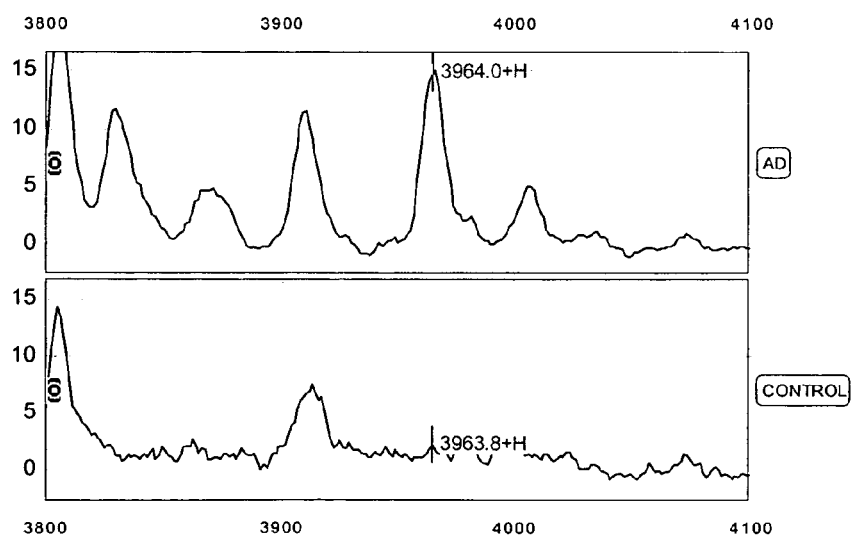
Figure 9M:
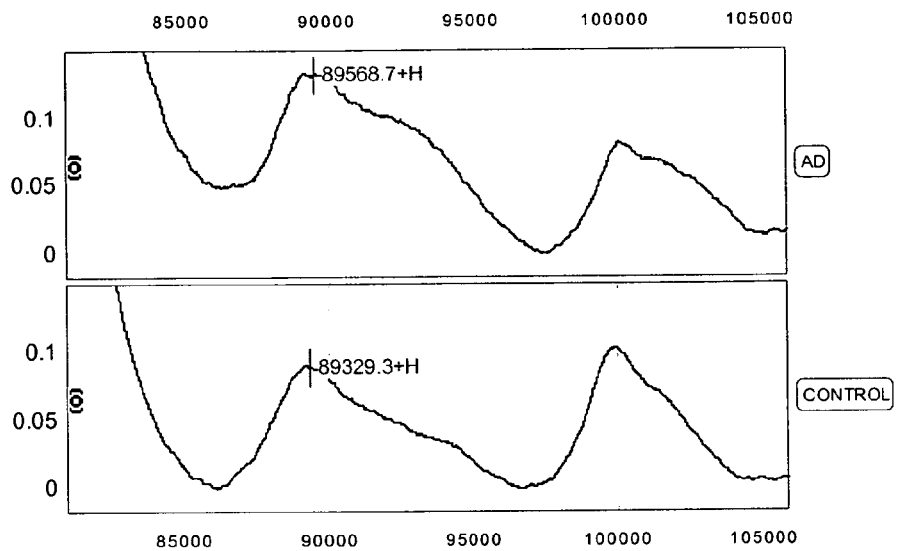
Figure 9N:
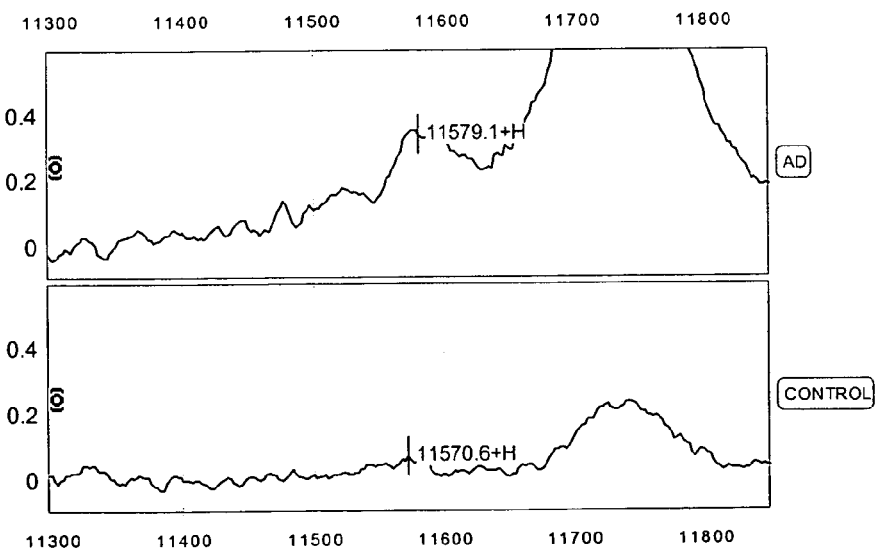
Figure 9O:
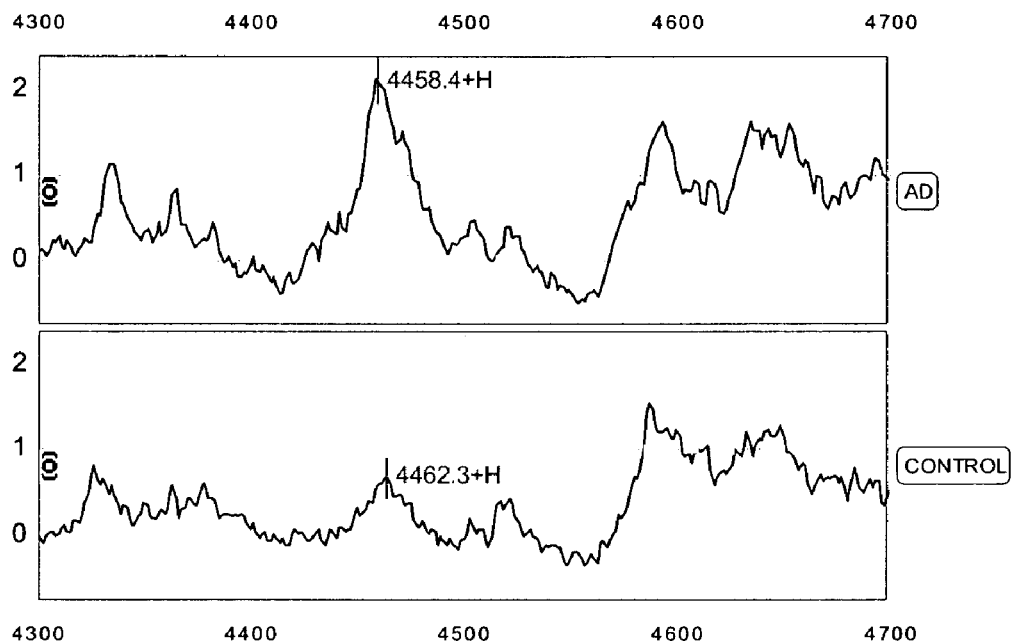
Figure 10:
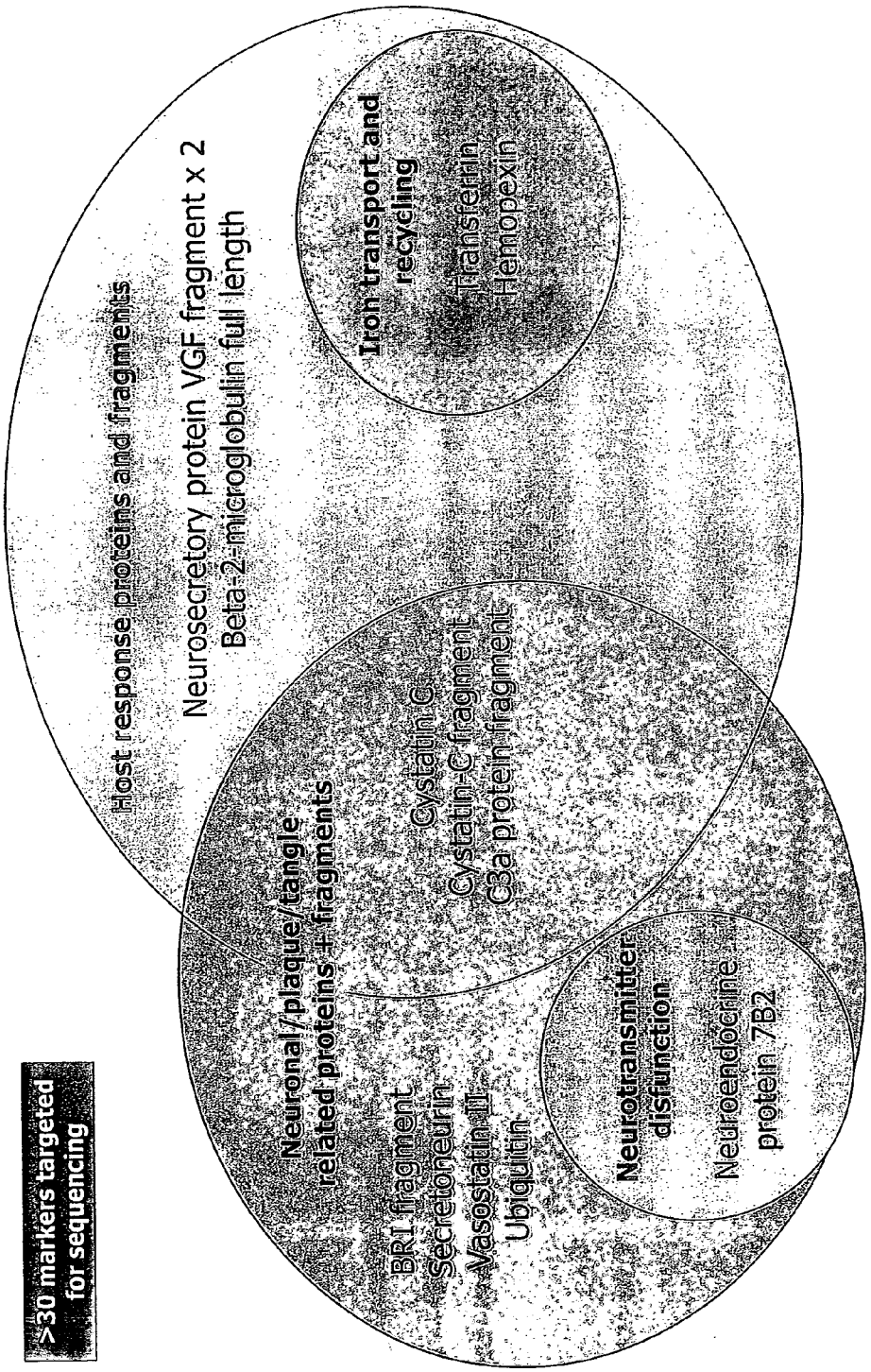

The results (FIG. 3) show that (1) the levels of β2 microglobulin in subjects suffering from Alzheimer's disease are significantly higher than the levels in subjects suffering from non-Alzheimer's dementia; (2) the levels of β2 microglobulin in subjects suffering from Alzheimer's disease are significantly higher than the levels in subjects who do not show symptoms of dementia; and (3) the levels of β2 microglobulin in subjects suffering from non-Alzheimer's dementia are significantly lower than the levels in subjects who do not show symptoms of dementia.

Example 3

Discovery of Additional Biomarkers for Alzheimer's Disease

For this Example, 237 CSF samples from Swedish and Finnish patients were used. These samples included: 98 samples from patients with Alzheimer's Disease (including 83 very mild cases with MMSE>24), 31 samples from patients with Frontotemporal Dementia (FTD), 29 samples from patients with dementia with Lewy Body (DLB), and 79 age-matched normal individuals including 9 depression controls. Diagnoses were made according to the NINCDS-ADRDA criteria discussed in the preceding Examples. The 237 samples were randomly divided into sets for training (⅔) and blind testing (⅓).

The anion exchange prefractionation step utilized in Example 1, above, was omitted for these CSF samples (note that for serum samples, the use of a pre-fractionation step is preferred). Instead, 5 µL of neat CSF sample was used per well on each chip. The chips used were Ciphergen's IMAC30 (activated with copper or nickel), Q10, CM10 and H50 ProteinChips. The samples were run in triplicate using multiple data collection settings using two different types of Energy Absorbing Molecules (EAM). A pooled normal reference CSF sample was run in parallel with clinical samples to monitor inter- and intra-assay reproducibility. All samples were processed and analyzed using a ProteinChip AutoBiomarker System that includes a Biomek® 2000 liquid-handling robot and ProteinChip TOF-MS Reader (Model PBS IIC) with chip Autoloader. Samples were randomized across different bioprocessors to eliminate any systematic bias.

1. General Chip Binding Protocol.
Bind CSF fractions to chips
Add 45 µL of corresponding buffer into each well
Add 5 µL of neat CSF
Chip Washing Buffer list:
IMAC30 array (Ciphergen Biosystems, Inc.):
100 mM $CuSO_4$ or $NiSO_4$, as appropriate
100 mM Sodium Phosphate+0.5M NaCl pH 7
H50 array (Ciphergen Biosystems, Inc.):
10% Acetonitrile+0.1% TFA
Q10 array (Ciphergen Biosystems, Inc.):
100 mM Tris pH 9.0
CM10 array (Ciphergen Biosystems, Inc.):
100 mM Sodium Acetate pH 4
Array Preparation
Place arrays into bioprocessor
Load IMAC30 arrays with copper or nickel, as appropriate
Load 50 µl of $CUSO_4$ (or $NiSO_4$) onto each spot of the IMAC30 array
Vortex 5' at Room Temperature (RT)
Remove $CuSO_4$ (or $NiSO_4$) and repeat
Water rinse
Equilibrate Arrays
Add 100 µl chip washing buffer appropriate to the array to each well
Vortex 5' at RT
Remove buffer after vortex
Add 100 µl chip washing buffer appropriate to the array to each well
Vortex 5' at RT
Remove buffer after vortex
Bind CSF fractions to arrays
Add 45 µl chip washing buffer appropriate to the array to each well
Add 5 µl CSF
Vortex 30' at RT
Remove sample and buffer
Wash Arrays
Add 100 µl chip washing buffer appropriate to the array to each well
Vortex 5' at RT
Remove buffer after vortex
Add 100 µl chip washing buffer appropriate to the array to each well
Vortex 5' at RT
Remove buffer after vortex
Add 100 µl chip washing buffer appropriate to the array to each well
Vortex 5' at RT
Remove buffer after vortex
Water rinse 2 times
Add Matrix
Remove Bioprocessor top and gasket
Allow the arrays to dry
SPA:
Add 1 µl 50% SPA (sinapinic acid) in 50% Acetonitrile and 0.5% TFA
Air dry
Add 1 µl 50% SPA
Air dry
CHCA
Add 1 µl 50% CHCA dissolved in 50% Acetonitrile+0.25% TFA
Air dry
Add 1 µl 50% CHCA
Air dry 2. Specific Chip Binding Protocols
Q10 Chip
Equilibrate Arrays
1. Add 100 µL 100 mM Tris pH9 to each well.
2. Mix 5 min at room temperature.
3. Remove buffer after mixing.
4. Add 100 µL 100 mM Tris pH9 to each well.
5. Mix 5 min at room temperature.
6. Remove buffer after mixing.
Add Sample to Arrays
1. Add 50 µL 100 mM Tris pH9 to each well.
2. Add 5 µL CSF.
3. Mix 30 min at room temperature.
4. Remove sample and buffer.
Wash Arrays
1. Add 100 µL 100 mM Tris pH9 to each well.
2. Mix 5 min at room temperature.
3. Remove buffer after mixing.
4. Add 100 µL 100 mM Tris pH9 to each well.
5. Mix 5 min at room temperature.
6. Remove buffer after mixing.

7. Add 100 µL 100 mM Tris pH9 to each well.
8. Mix 5 min at room temperature.
9. Remove buffer after mixing.
10. Rinse twice with deionized water
Add EAM
1. Remove Bioprocessor reservoir and gasket.
2. Briefly allow the arrays to dry.
3. Apply EAM:
For SPA
a. Add 400 µL of 50% acetonitrile, 0.5% TFA to SPA tube.
b. Mix 5 min at room temperature.
c. Add 1 µL to each spot.
d. Air dry.
e. Add 1 µL to each spot.
f. Air dry.
For CHCA
a. Add 200 µL of 50% ACN, 0.25% TFA to CHCA tube.
b. Mix 5 min at room temperature.
c. Centrifuge for 1 min at 10,000 rpm at room temperature.
d. Remove the supernatant and dilute with an equal volume of 50% acetonitrile, 0.25% TFA.
e. Apply 1 µL to each spot.
f. Air dry.
g. Apply 1 µL to each spot.
h. Air dry.
CM10
Equilibrate Arrays
1. Add 100 µL 100 mM Sodium acetate pH 4 to each well.
2. Mix 5 min at room temperature.
3. Remove buffer after mixing.
4. Add 100 µL 100 mM Sodium acetate pH 4 to each well.
5. Mix 5 min at room temperature.
6. Remove buffer after mixing.
Add Sample to Arrays
1. Add 50 µL 100 mM Sodium acetate pH 4 to each well.
2. Add 5 µL CSF.
3. Mix 30 min at room temperature.
4. Remove sample and buffer.
Wash Arrays
1. Add 100 µL 100 mM Sodium acetate pH 4 to each well.
2. Mix 5 min at room temperature.
3. Remove buffer after mixing.
4. Add 100 µL 100 mM Sodium acetate pH 4 to each well.
5. Mix 5 min at room temperature.
6. Remove buffer after mixing.
7. Add 100 µL 100 mM Sodium acetate pH 4 to each well.
8. Mix 5 min at room temperature.
9. Remove buffer after mixing.
10. Rinse twice with deionized water
Add EAM
1. Remove Bioprocessor reservoir and gasket.
2. Briefly allow the arrays to dry.
3. Apply EAM:
For SPA
a. Add 400 µL of 50% acetonitrile, 0.5% TFA to SPA tube.
b. Mix 5 min at room temperature.
c. Add 1 µL to each spot.
d. Air dry.
e. Add 1 µL to each spot.
f. Air dry.
For CHCA
a. Add 200 µL of 50% ACN, 0.25% TFA to CHCA tube.
b. Mix 5 min at room temperature.
c. Centrifuge for 1 min at 10,000 rpm at room temperature.
d. Remove the supernatant and dilute with an equal volume of 50% acetonitrile, 0.25% TFA.
e. Apply 1 µL to each spot.
f. Air dry.
g. Apply 1 µL to each spot.
h. Air dry.
IMAC30 and H50 ProteinChips
See the protocols in Examples 1 and 2, respectively, for IMAC 30 and H50 ProteinChip protocols. The protocol for the IMAC30 ProteinChips is essentially the same as that given for the IMAC3 ProteinChip except that, as with the all the chips in this Example, the anion exchange fractionation step as been eliminated. The IMAC30 ProteinChip is an alternative to the IMAC3 arrays with the added feature of a hydrophobic barrier for sample containment. Like the IMAC3 arrays, the IMAC30 arrays are activated with transition metals (e.g., copper or nickel) prior to use.

3. Data acquisition settings:
The following conditions were used for data acquisition.
IMAC30 Cu: CHCA, SPA low, SPA high (50% SPA used as the energy absorbing molecule)
IMAC30 Ni: CHCA; SPA low, SPA high
Q10: CHCA, SPA low, SPA high
CM10: CHCA; SPA low, SPA high
H50: CHCA; SPA low, SPA high
CHCA
Set Detector Voltage 2850 Volts.
Set high mass to 200000 Daltons, optimized from 1000 Daltons to 200000 Daltons.
Set starting laser intensity to 170.
Set starting detector sensitivity to 7.
Focus mass at 4000 Daltons.
Set Mass Deflector to 1000 Daltons.
Set data acquisition method to Seldi Quantitation
Set Seldi acquisition parameters 22. delta to 5. transients per to 5 ending position to 82.
Set warming positions with 2 shots at intensity 220 and Don't include warming shots.
Process sample.
SPA low
Set Detector Voltage 2850 Volts.
Set high mass to 200000 Daltons, optimized from 1000 Daltons to 200000 Daltons.
Set starting laser intensity to 194.
Set starting detector sensitivity to 8.
Focus mass at 4000 Daltons.
Set Mass Deflector to 1000 Daltons.
Set data acquisition method to Seldi Quantitation
Set Seldi acquisition parameters 20. delta to 5. transients per to 5 ending position to 80.
Set warming positions with 2 shots at intensity 220 and Don't include warming shots.
Process sample.
SPA high
Set Detector Voltage 2850 Volts.
Set high mass to 200000 Daltons, optimized from 10000 Daltons to 200000 Daltons.
Set starting laser intensity to 199.
Set starting detector sensitivity to 8.
Focus mass at 12000 Daltons.
Set Mass Deflector to 4000 Daltons.
Set data acquisition method to Seldi Quantitation
Set Seldi acquisition parameters 22. delta to 5. transients per to 5 ending position to 82.

Set warming positions with 2 shots at intensity 220 and Don't include warming shots.
Process sample.

4. Data Analysis:

Spectral data was collected using ProteinChip Software version 3.1. with large scale data handling and univariate analysis performed using CiphergenExpress™ Data Manager 2.1. Spectral pre-processing included baseline subtraction and internal molecular weight calibration using known masses from endogenous sample analytes. Normalization of peak intensity was performed by total ion current using an external coefficient of 0.2. Peak labelling and clustering across different spectra was done automatically by the software employing user-defined settings. Peak intensity P values for individual peaks across each group were calculated using a Mann-Whitney test for two group comparisons and Kruskal-Wallis Test for three or more groups. Multivariate data analysis was performed using the Biomarker Patterns™ Software 5.0 to best classify the samples based on pre-determined phenotype.

Results

Using the ProteinChips and conditions described above, a set of univariate biomarkers (P<0.005) was identified after analysis of the training set ("Study 2", i.e., ⅔ of the sample set described above) under all conditions. The results are summarized in Table II, below.

TABLE II

| ROC area | p-value | P value comparison | Cluster mass | Assay | Up/Down in AD | ID |
|---|---|---|---|---|---|---|
| 0.26 | 0.00000083 | AD/N | 4332.9 (4330.4) | IMAC 30 Cu SPA Low and Ni CHCA | Up | |
| 0.39 | 0.00000300 | AD/C + N | 4342.1 | IMAC 30 Ni SPA low | Up | |
| 0.28 | 0.00000698 | AD/N | 3680.7 | Q10 SPA low | Up | Secretogranin II peptide (secretoneurin) |
| 0.28 | 0.00001000 | AD/N | 5078.4 (5078.3) (5082.6) | H50, IMAC 30 Cu, CM10 SPA high | Up | |
| 0.32 | 0.00001278 | AD/C + N | 4757.9 | H50 SPA low | Up | |
| 0.34 | 0.00002000 | AD/C + N | 10362.1 | H50 CHCA | Up | |
| 0.38 | 0.00002055 | AD/N | 2431.2 (2433.1) | IMAC30 Cu CHCA, CM10 SPA low | Up | Truncated ABri/ADan amyloid peptide of Integral membrane protein 2B |
| 0.37 | 0.00003000 | AD/C | 11753.4 (11763.7) (11747.0) (11749.4) | H50, IMAC 30 Ni, CM10 and Q10 SPA low | Up | Beta-2-microglobulin |
| 0.37 | 0.00003000 | AD/N | 12583.4 (12544.7) (12556.3) | H50, IMAC 30 Cu, CM10 SPA low | Up | 8 aa truncated Cystatin C |
| 0.35 | 0.00007220 | AD/N | 4352.4 (4353.7) | Q10 CHCA and SPA low | Up | alpha-1-antichymotrypsin C-terminal fragment |
| 0.34 | 0.00007977 | AD/C + N | 4737.8 | IMAC 30 Ni | Up | |
| 0.36 | 0.00010089 | AD/C + N | 3234.3 (3235.5) (3236.8) | CM10 CHCA, IMAC 30 Cu and Ni CHCA | Up | |
| 0.32 | 0.00010151 | AD/N | 6634.3 | Q10 SPA low | Up | |
| 0.63 | 0.00013746 | AD/N | 11127.8 | CM10 CHCA | Down | |
| 0.38 | 0.00016000 | AD/C + N | 5062.5 (5063.0) (5067.4) | CM10 CHCA and Q10 CHCA and SPA low | Up | |
| 0.31 | 0.00016894 | AD/N | 3687.7 | CM10 CHCA | Up | N-terminal fragment of Neurosecretory protein VGF (-3aa) (Fragment 2) |
| 0.32 | 0.00021243 | AD/N | 3951.6 (3966.2) | CM10 CHCA and SPA low | Up | N-terminal fragment of Neurosecretory protein VGF (Fragment 1) |
| 0.37 | 0.00021656 | AD/C | 4971.3 | CM10 CHCA | Up | Thymosin beta-4 (N-acetylated) |
| 0.33 | 0.00027133 | AD/N | 3912.8 | Q10 SPA low | Up | |
| 0.35 | 0.00030200 | AD/C + N | 9742.3 (9752.4) | Q10 CHCA and SPA low | Up | |
| 0.43 | 0.00033000 | AD/C + N | 3982.6 | IMAC 30 Ni CHCA | Up | |
| 0.32 | 0.00039159 | AD/C + N | 4813.3 | Q10 SPA low | Up | |

TABLE II-continued

| ROC area | p-value | P value comparison | Cluster mass | Assay | Up/Down in AD | ID |
|---|---|---|---|---|---|---|
| 0.34 | 0.00041439 | AD/N | 6501.9 | IMAC 30 Ni CHCA | Up | |
| 0.37 | 0.00050908 | AD/C + N | 8183.6 | CM10 CHCA | Up | Ubiquitin truncated from C-terminus (-4aa) |
| 0.37 | 0.00051300 | AD/N | 6527.1 | IMAC 30 Ni SPA low | Up | |
| 0.64 | 0.00056603 | AD/C + N | 3821.2 | Q10 SPA low | Down | |
| 0.33 | 0.00065202 | AD/N | 4184.3 | IMAC 30 Cu CHCA | Up | |
| 0.36 | 0.00067000 | AD/C + N | 4743.5 (4753.7) | CM10 CHCA and Q10 SPA low | Up | |
| 0.36 | 0.00075331 | AD/C | 9789.1 | H50 SPA low | Up | |
| 0.36 | 0.00080000 | AD/N | 7269.3 (7276.9) | CM10 SPA low and IMAC30 Cu SPA high | Up | |
| 0.61 | 0.00091828 | AD/C | 60976.2 | IMAC 30 Cu SPA Low and Ni CHCA | Down | Hemopexin |
| 0.38 | 0.00107103 | AD/C | 89874.1 (90605.3) | CM10 SPA high and Q10 SPA high | Up | |
| 0.35 | 0.00115893 | AD/N | 2248.2 | CM10 CHCA | Up | |
| 0.34 | 0.00151443 | AD/N | 8933.2 (8936.9) | IMAC 30 Cu SPA low and Ni CHCA | Up | Complement 3a des-Arg |
| 0.38 | 0.00165366 | AD/C + N | 21100.1 | Q10 SPA high | Up | |
| 0.35 | 0.00179305 | AD/N | 7281.7 | Q10 SPA high | Up | |
| 0.43 | 0.00193474 | AD/C | 5281.9 | IMAC 30 Ni SPA high | Up | |
| 0.39 | 0.00197628 | AD/N | 6519.2 (6515.2) | IMAC 30 Cu SPA high and Ni SPA low | Up | |
| 0.41 | 0.00200779 | AD/C | 4019.8 | IMAC 30 Ni | Up | |
| 0.64 | 0.00205481 | AD/N | 6441.6 | H50 SPA low | Down | |
| 0.41 | 0.00237350 | AD/C + N | 4007.1 | IMAC 30 Ni CHCA | Up | |
| 0.39 | 0.00249026 | AD/C + N | 3514.5 (3511.3) (3517.7) | IMAC 30 Cu, CM10 CHCA and SPA low | Up | C-terminal fragment of Neuroendocrine protein 7B2 |
| 0.61 | 0.00256521 | AD/C + N | 14152.3 | IMAC 30 Ni SPA low | Down | Transthyretin S-glutathionylated |
| 0.35 | 0.00294281 | AD/C | 7676.9 | IMAC 30 Cu CHCA | Down | |
| 0.40 | 0.00299932 | AD/C | 8207.8 | CM10 SPA high | Up | |
| 0.35 | 0.00300866 | AD/N | 3253.5 | IMAC 30 Ni CHCA | Up | |
| 0.42 | 0.00342646 | AD/C + N | 3818.0 | IMAC 30 Ni SPA low | Up | |
| 0.37 | 0.00362052 | AD/N | 158656.8 | CM10 SPA high | Up | |
| 0.35 | 0.00385295 | AD/N | 2628.2 | CM10 CHCA | Up | |
| 0.38 | 0.00397209 | AD/C + N | 6642.3 | IMAC 30 Cu SPA high | Up | |
| 0.44 | 0.00418700 | AD/C | 4986.4 | IMAC 30 Ni | Up | |
| 0.39 | 0.00441947 | AD/C + N | 3705.0 | CM10 SPA low | Up | |
| 0.36 | 0.00448691 | AD/N | 8981.5 | IMAC 30 Ni SPA low | Up | |
| 0.38 | 0.00497339 | AD/C | 14619.6 | IMAC 30 Ni SPA high | Up | |

An additional analysis was performed utilizing a complete sample set (i.e., 236 samples comprising 98 AD (including 83 very mild cases with an MMSE>24), 78 normals, 31 FTD and 29 Lewy Body Dementia cases). Using this complete sample set, a set of unique peaks were found which were able to separate the AD samples from one of the other groups with a P value of <0.001. The biomarkers range in size from 2-90 kDa. These peaks are presented in Table IV-A, below. Note that the masses listed in Table IV-A differ slightly from those in Table II. The masses in Table IV-A reflect additional instrument calibration using the theoretical molecular weights of the biomarkers identified in earlier studies.

A further analysis was performed utilizing a subset of the samples derived solely from the Gothenburg site (i.e., 113 samples comprising 64 AD (including 49 very mild cases with an MMSE>24) and 49 clinically normal individuals). A set of unique peaks were found which were able to separate AD samples from clinically normal with a P value of <0.005. The biomarkers range in size from 3.5-92.1 kDa. These peaks are presented in Table IV-B, below. Reported in the table are masses using internal spectral calibration (using the masses of known proteins and peptides as calibrants) and theoretical mass predicted from sequenced where available.

TABLE IV-A

| Cluster mass, Da | AD vs. Normal | AD vs. FTD | AD vs. DLB | Up/Down in AD | ProteinChip Assay | Identification |
|---|---|---|---|---|---|---|
| 2429.8 | 0.95487612 | 0.00017162 | 0.26538695 | Up | ICc | Integral Membrane 2B C-terminal fragment |
| 3215.5 | 0.23273391 | 0.00001642 | 0.01118477 | Down | Hc | |
| 3235.8 | 0.00006439 | 0.00225532 | 0.14515129 | Up | Cc + ICc + INc | |
| 3315.9 | 0.69596856 | 0.00002396 | 0.03491240 | Down | Hc | |
| 3513.8 | 0.00098304 | 0.04572348 | 0.00386392 | Up | Cs + ICc + ICs | Neuroendocrine protein 7B2 C-terminal fragment |
| 3669.9 | 0.09454931 | 0.10767137 | 0.00041166 | Up | Cc | |
| 3681.3 | 0.11666086 | 0.00436488 | 0.00001668 | Up | Qs | Secretogranin II fragment (secretoneurin) |
| 3691.2 | 0.12619916 | 0.06923653 | 0.00000279 | Up | Cc + Cs | VGF N-terminal fragment 2 |
| 3909.2 | 0.00648300 | 0.00955931 | 0.00035033 | Up | Qs | Chromogranin A fragment |
| 3932.9 | 0.01023885 | 0.00002062 | 0.00130144 | Up | Qs | |
| 3948.5 | 0.02027587 | 0.07735421 | 0.00000212 | Up | Cc | VGF N-terminal fragment 1 |
| 3966.1 | 0.00075979 | 0.01030175 | 0.00066025 | Up | Cs | |
| 4146.5 | 0.02001680 | 0.00051124 | 0.00032008 | Up | Qs | |
| 4183.1 | 0.05179624 | 0.00000000 | 0.10283792 | Up | Icc | |
| 4335.4 | 0.00032119 | 0.00000000 | 0.00051926 | Up | ICs + INc | |
| 4353.2 | 0.02412351 | 0.00156337 | 0.00005341 | Up | Qs | Alpha-1-antichymotrypsin C-terminal fragment |
| 4746.0 | 0.036828 | 0.000941 | 0.000370 | Up | Hs + Cs | |
| 4809.5 | 0.39862870 | 0.03111856 | 0.00001209 | Up | Qs | |
| 4974.0 | 0.00000187 | 0.00001239 | 0.00013077 | Up | Cc | Thymosin beta-4 (N-acetylated) |
| 5003.5 | 0.000081 | 0.000001 | 0.000219 | Up | Hs | |
| 5059.7 | 0.00089928 | 0.00504850 | 0.00067411 | Up | Cs + Qs + Ics + Hs | |
| 6256.9 | 0.04206642 | 0.01734302 | 0.00036644 | Up | Qs | |
| 6273.8 | 0.00321745 | 0.00013350 | 0.00644068 | Up | Cs + ICc + ICs + INc | |
| 6446.3 | 0.565441 | 0.000036 | 0.017879 | Down | Hs + Hc | Apolipoprotein C-I (2 aa deleted from N-terminus) |
| 6502.9 | 0.00090782 | 0.00050848 | 0.00266677 | Up | INc + INs | |
| 6674.1 | 0.24876618 | 0.10787226 | 0.00000515 | Up | Qs | |
| 6681.5 | 0.77039619 | 0.00022426 | 0.31943288 | Down | INc | |
| 8291.9 | 0.00000468 | 0.03077283 | 0.01707923 | Up | Cc | Ubiquitin (3 aa deleted from C-terminus) |
| 8575.5 | 0.00000969 | 0.00025594 | 0.00876087 | Up | Cc | Ubiquitin Full Length |
| 8934.5 | 0.11176238 | 0.00002279 | 0.09368956 | Up | ICs + INc + INs | C3a anaphylatoxin des-Arg |
| 9759.9 | 0.00119119 | 0.01428452 | 0.00089480 | Up | Qs | |
| 9804.6 | 0.000303 | 0.004270 | 0.067531 | Up | Hs | |
| 10377.7 | 0.000013 | 0.000125 | 0.021733 | Up | Hc + Hs | |
| 11371.9 | 0.80246140 | 0.00002687 | 0.50685072 | Up | INs | |
| 11733.2 | 0.00000240 | 0.00532157 | 0.00496514 | Up | Cs + Qs + ICc + INc + Ins + Hc + Hs | Beta-2-Microglobulin |
| 12542.2 | 0.01464240 | 0.00000416 | 0.01333416 | Up | Cc + Cs + ICc + ICs + INc + Ins + Hc + Hs | Cystatin-C N-terminal truncation |
| 13958.9 | 0.00096765 | 0.55798776 | 0.08726619 | Down | INs | Transthyretin S-Cys and/or S-CysGly |
| 14112.5 | 0.00081568 | 0.33747927 | 0.00238552 | Down | INs | Transthyretin S-glutathionylated |
| 14540.2 | 0.16249090 | 0.00005669 | 0.89261196 | Up | INs | |
| 21030.1 | 0.46655641 | 0.00015990 | 0.10034825 | Up | Qs | Retinol Binding Protein |
| 59280.8 | 0.00000119 | 0.67722736 | 0.17701643 | Down | ICs + INc + INs | Hemopexin |

TABLE IV-A-continued

| Cluster mass, Da | AD vs. Normal | AD vs. FTD | AD vs. DLB | Up/Down in AD | ProteinChip Assay | Identification |
|---|---|---|---|---|---|---|
| 66472.2 | 0.20360350 | 0.00014003 | 0.72727727 | Up | Cc | Albumin |
| 79098.4 | 0.00027794 | 0.00000018 | 0.00584688 | Up | Cc | Transferrin |
| 89388.0 | 0.01053139 | 0.00000151 | 0.83952605 | Up | Cc + ICc | |

Legend:

IC - IMAC chip, activated with Cu;

IN - IMAC chip, activated with Ni;

H - H50 chip;

C - CM10 chip;

Q - Q10 chip;

lower case "c" and "s" refer to the use of the energy absorbing molecules SPA and CHCA, respectively.

TABLE IV-B

| M/Z (int. cal) | P Total | ROC | AD v. N | Best Condition | # of Conditions | ID | Calculated MW, Da |
|---|---|---|---|---|---|---|---|
| 60464.7 | <0.0001 | 0.8409 | down | IM Ni SPA high | 2 | Hemopexin | glycosylated |
| 3513.9 | <0.0001 | 0.8219 | up | CM 10 SPA low | 6 | 7B2 CT fragment | 3,512.84 |
| 8291.0 | <0.0001 | 0.819 | up | CM 10 SPA high | 1 | Ubiquitin -3aa from CT | 8,294.55 |
| 11725.7 | <0.0001 | 0.8058 | up | H50 SPA high | 14 | Beta-2-Microglobulin | 11,731.17 |
| 5044.2 | <0.0001 | 0.7972 | up | CM 10 SPA high | 12 | | |
| 10379.8 | <0.0001 | 0.7943 | up | H50 CHCA | 1 | 10.3 kDa | |
| 9984.6 | <0.0001 | 0.7832 | up | H50 CHCA | 5 | related to 10.3 kDa | |
| 10265.6 | <0.0001 | 0.7796 | up | H50 CHCA | 1 | related to 10.3 kDa | |
| 9802.4 | <0.0001 | 0.7757 | up | Q10 SPA high | 5 | EA-92 (ChrA peptide) | 9,730.18 |
| 9757.0 | <0.0001 | 0.7735 | up | CM 10 SPA high | 2 | related to 10.3 kDa | |
| 16207.4 | <0.0001 | 0.7634 | up | IM Cu SPA high | 3 | Pancreatic ribonuclease | glycosylated |
| 14092.7 | <0.0001 | 0.7631 | down | IM Ni SPA high | 2 | Transthyretin S-glutathionylated | 14,067 |
| 13904.7 | <0.0001 | 0.758 | down | IM Ni SPA high | 6 | Transthyretin S-Cys/S-CysGly | 13,880/13,937 |
| 12545.9 | <0.0001 | 0.7503 | up | CM 10 SPA high | 5 | Cystatin-C -8aa from NT | 12,540.22 |
| 8183.6 | <0.0001 | 0.7481 | up | CM 10 SPA high | 2 | Ubiquitin -4aa from CT | 8,181.39 |
| 5227.4 | <0.0001 | 0.7477 | up | H50 CHCA | 1 | | |
| 3687.0 | <0.0001 | 0.7363 | up | Q10 SPA low | 1 | Secretoneurin (ChrC/SGII peptide) | 3,679.01 |
| 3906.4 | <0.0001 | 0.7321 | up | IM Cu CHCA | 5 | Vasostatin II (ChrA peptide) | 3,908.13 |
| 78936.5 | <0.0001 | 0.7315 | down | IM Ni SPA high | 4 | Transferrin | glycosylated |
| 3806.2 | <0.0001 | 0.7312 | up | IM Ni CHCA | 3 | | |
| 8955.1 | <0.0001 | 0.7312 | up | Q10 SPA high | 1 | | |
| 5263.9 | <0.0001 | 0.7309 | up | CM 10 SPA low | 1 | | |
| 14565.1 | <0.0001 | 0.7286 | up | IM Ni SPA high | 1 | Pancreatic ribonuclease | 14,574.33 |
| 20839.2 | <0.0001 | 0.7254 | up | IM Cu CHCA | 4 | | |
| 6509.6 | <0.0001 | 0.7235 | up | IM Ni CHCA | 1 | Chromogranin B peptide | 6,502.87 |
| 4320.6 | <0.0001 | 0.7213 | up | IM Ni CHCA | 3 | A-beta 1-40 | 4329.86 |
| 7258.2 | 0.0002 | 0.7205 | up | Q10 SPA high | 3 | Chromogranin B peptide | 7,262.42 |
| 17349.3 | 0.0001 | 0.7199 | down | CM 10 SPA high | 1 | Apolipoprotein A-II dimer | 17,379.82 |
| 58845.4 | <0.0001 | 0.7194 | down | IM Cu CHCA | 1 | | |
| 8938.5 | 0.0001 | 0.713 | up | IM Cu CHCA | 1 | C3a des-Arg | 8,932.50 |
| 6608.9 | 0.0003 | 0.7115 | up | Q10 SPA high | 2 | | |
| 13349.5 | 0.0001 | 0.7108 | up | H50 SPA low | 6 | CysC | 13,347.14 |
| 5838.3 | 0.0003 | 0.7083 | up | Q10 SPA high | 1 | | |
| 23477.4 | 0.0004 | 0.7063 | up | Q10 SPA high | 1 | Prostaglandin-D synthase | glycosylated |
| 4357.0 | 0.0005 | 0.704 | up | Q10 SPA low | 2 | Alpha-1-antichymotrypsin CT fragment | 4,354.19 |
| 7653.2 | 0.0006 | 0.6901 | up | IM Cu SPA high | 11 | Osteopontin CT fragment | 7658.19 |
| 16716.9 | 0.0007 | 0.6899 | up | CM10 CHCA | 5 | | |
| 4812.5 | 0.0021 | 0.6791 | up | Q10 SPA low | 1 | VGF(NCBI) peptide | 4,808.80 |
| 4989.4 | 0.0012 | 0.6783 | up | IM Cu SPA low | 7 | Thymosin beta-4-acetylated | 4,967.46 |
| 7878.7 | 0.0012 | 0.6779 | up | IM Ni SPA low | 1 | | |
| 92082.4 | 0.0016 | 0.6738 | up | IM Cu SPA high | 4 | | |
| 66479.2 | 0.0038 | 0.6685 | down | Q10 SPA high | 4 | Albumin | |
| 3967.6 | 0.0023 | 0.6677 | up | IM Ni CHCA | 1 | | |
| 7718.8 | 0.0023 | 0.6677 | up | IM Cu SPA high | 4 | Osteopontin CT fragment phosphorylated | 7738.19 |
| 89707.1 | 0.0032 | 0.667 | up | CM10 SPA high | 1 | | |
| 11579.2 | 0.0027 | 0.6652 | up | H50 SPA high | 1 | | |

TABLE IV-B-continued

| M/Z (int. cal) | P Total | ROC | AD v. N | Best Condition | # of Conditions ID | | Calculated MW, Da |
|---|---|---|---|---|---|---|---|
| 8585.9 | 0.0039 | 0.6635 | up | CM10 SPA high | 1 | Ubiquitin | 8564.84 |
| 4455.4 | 0.0034 | 0.6614 | up | IM Cu CHCA | 2 | | |

FIG. 4A-K shows the distribution of peak intensities observed for the various groups and the results of Mann-Whitney or Kruskal-Wallis tests used to determine the significance of any differences observed. FIGS. 5-8 also show results obtained from the analysis of (1) a set of case-control age-matched AD vs. Normal sample set (n=86) and (2) an Ab42/T-Tau pre-selected sample set (n=104) comprising 69 AD and 35 Normals (AD group with Tau>450+Ab42<550 and normals the reverse). FIG. 9 shows examples of mass spectra obtained for many of the biomarkers of Table IV-A and IV-B.

The identities of a number of the peaks detected in this study were established using methods similar to those described above. Biomarkers were purified using combinations of chromatography techniques employing a range of Biosepra sorbents typically followed by 1D-SDS-PAGE. The purification schemes were monitored using a ProteinChip system to track biomarkers of interest. For proteins smaller than 30 kDa, intact bands of interest were extracted from gels and reanalyzed using the ProteinChip Reader to confirm the mass matched with the original biomarker. The gel-extracted proteins were in-solution digested with trypsin and proteins larger than 30 kDa were in-gel digested. Tryptic digests were analyzed by peptide mapping using the ProteinChip Reader and by tandem MS using a Q-STAR (Applied Biosystems) instrument fitted with a PCI-1000 ProteinChip Interface. Biomarkers smaller than 4 kDa were enriched by combinations of chromatography techniques and identified directly by tandem MS without SDS-PAGE purification and/or trypsin digestion.

For instance, the following peptides/proteins were identified:

M11727: This protein was identified as β2 microglobulin (Swiss-Prot accession number P01884, http://us.expasy.org/cgi-bin/niceprot.p1?P01884), which finding is consistent with the findings of Example 1 and 2. β2 microglobulin (B2M) is a potential initiator of inflammatory responses in that (1) it directs intracellular transport of major histocompatibility complex class I molecules; and (2) it is modulated by interferons and certain cytokines that also play an important role in inflammation. Its role as a CSF biomarker for AD has previously been discussed. However, it has now been identified as a biomarker for AD in blood.

M3680.7: This peptide was identified as a Secretogranin II peptide (also known as secretoneurin), which has the italicized sequence of SEQ ID NO:2. Secretogranin II is a large dense-core synaptic vesicle protein. The levels of secretogranin II were observed to decrease in the temporal cortex of AD patients vs. age-matched controls. One of the main features of AD is a degeneration of synapses. The levels of secretoneurin peptide in CSF may therefore reflect synaptic loss. This loss of synapses, reflected by early cognitive impairments, precedes the appearance of extra cellular focal deposits of beta-amyloid peptide in the brain of patients.

M78677.3: This protein was identified as Transferrin (Swiss-Prot accession number P02787), which is consistent with the findings of Example 1. Transferrin is a major transport protein for iron, which is a major factor in free radical generation and oxidative stress in neurodegenerative diseases. Transferrin levels increase in AD frontal cortex, compared with elderly controls. C2 allele associated with AD in ApoE4 negative subjects. ApoE and Transferrin may be part of a complex mechanism in the pathogenesis of Alzheimer's disease.

M2431.2: This peptide was identified as a truncated ABri/ADan amyloid peptide of Integral Membrane Protein 2B (MMP2B or BRI), which has the underlined sequence of SEQ ID NO:3. The exact physiological role in the brain is yet to be fully understood. Mutations in BRI gene cause rare neurodegenerative conditions—familial British and Danish dementia—which involve deposition of the extended amyloidogenic peptides (ADan/ABri) and bear striking neuropathological similarities to AD. This is the first time the shorter WT form of the C-terminal peptide has been associated with a disease.

M13391 peptide was identified to be full-length Cystatin C, which has the italicized sequence of SEQ ID NO:4. Cystatin C is found in most bodily fluids and tissues and is a marker of renal function in urine. Cystatin C inhibits activity of lysosomal cysteine proteases (Cathepsins). Cystatin-C/Cathepsin balance is important for many disease processes including inflammation, cancer and AD. Cystatin C is associated with AD. For instance, CST3 B/B homozygosity is associated with an increased risk of developing AD; Cystatin C increases in AD brain at neuronal sites most susceptible to cell death in AD independent of cystatin C genotype; and Cystatin C co-localizes with A-beta in AD brain deposits.

M12583.4: This peptide was identified as a truncated Cystatin C peptide, which has the underlined sequence of SEQ ID NO:4. This truncated Cys-C, which lacks the first eight N-terminal residues, has a 20-fold lower affinity for Cathepsin B, but not other cathepsins. Cathepsin B plays key role in AD. It is identified in most early endosomes in Alzheimer brains, but detectable in only a minor proportion of endosomes in normal brain. Specific cathepsin B inhibitors abolish neurotoxic effects caused by Abeta42-activated microglial cells. It has been found that this truncated Cys-C is a biomarker for AD in both CSF and blood. This is the first time this 8aa N-terminal truncated version has been described in CSF or blood.

M3951.6: This peptide was identified to be a N-terminal fragment of the Neurosecretory protein VGF, which has the italicized sequence of SEQ ID NO:5. Similarly, the M3687.7 peptide was identified to be a N-terminal fragment of Neurosecretory protein VGF (-3amino acids), which has the bolded sequence of SEQ ID NO:5. The Neurosecretory protein VGF is a nerve growth factor selectively synthesized in neuroendocrine and neuronal cells. VGF mRNA levels are regulated by neuronal activity, including long-term potentiation, seizure, and injury. The sequence is rich in paired basic amino acid residues that are potential sites for proteolytic processing. Such fragments appear to be novel. A different fragment of the same protein was discovered by another group.

M60976.2: This protein was identified as Hemopexin (Swiss-Prot accession number P02790). Hemopexin is an acute phase reactant protein induced after inflammation by IL-6; a scavenger/transporter of heme to prevent heme-mediated oxidative stress; and also believed to play a role in nerve repair.

M8933.2: This peptide was identified to be C3a anaphylatoxin desArg, which has the underlined sequence of SEQ ID NO: 6. The full-length sequence for the C3a anaphylatoxin peptide is the italicized sequence of SEQ ID NO: 6. Complement activation known to occur in the AD brain: (1) contributes to the development of a local inflammatory state; and (2) correlated with cognitive dysfunction. Localization and potential mechanism for C3 in AD brain: (1) protein expression increases (5-10 fold) in cultured mice microglial cells in response to A-Beta synthetic peptides; and (2) inhibition of C3 in hAPP mice increases plaque deposition and neuronal degeneration—potential role in clearance. This peptide is a novel complement protein fragment marker of AD.

M3514.5: This peptide was identified as a C-terminal fragment of Neuroendocrine protein 7B2, which has the underlined sequence of SEQ ID NO: 7. The C-terminal fragment corresponds to amino acids 182-212; the full-length protein has the italicized sequence of SEQ ID NO: 7. Neuroendocrine protein 7B2 complexes with Prohormone Convertase 2 (PC2) in the endoplasmic reticulum (ER). PC2 processes somatostatin precursors. Once the proPC2/7B2 complex arrives at the trans-Golgi network, 7B2 is internally cleaved into two domains, the 21-kDa fragment and a carboxy-terminal 31 residue peptide. If proPC2 has not encountered 7B2 intracellularly, it cannot generate a catalytically active mature species. A marked decrease in the ratio of the PC2 precursor to the total enzymatic pool is observed in the frontal cortex of Alzheimer patients. This decrease coincides with an increase in the binding protein 7B2. A somatostatin deficit occurs in the cerebral cortex of Alzheimer's disease patients without a major loss in somatostatin-containing neurons. This deficit could be related to a reduction in the rate of proteolytic processing of peptide precursors. There is a body of evidence to suggest that certain forms of somatostatin in CSF correlate with dementia severity.

M3912.8: This peptide was identified as a fragment of chromogranin A (CMGA_HUMAN (SwissProt # P10645)) corresponding to the italicized sequence in SEQ ID NO: 8. The underlined sequence in SEQ ID NO: 8 is vasostatin I. The protein consisting of the underlined sequence and the italicized sequence is vasostatin II, a fragment of chromogranin A with vasoinhibitory properties. Chromogranin A is the major protein of large dense-core synaptic vesicles. The ratio of chromogranin A to secretogranin II in the temporal cortex is significantly correlated to the clinical severity of dementia and to the extent of neuropathological changes. The levels of the vasostatin II peptide in CSF may reflect synaptic loss.

M4352.4: This peptide was identified as a C-terminal fragment of alpha-1-antichymotrypsin (SwissProt # P01011; theoretical MW 4354.19 Da; SEQ ID NO: 9). This is an acute phase/inflammatory protein overproduced in the AD brain that can promote the formation of, and is associated with, neurotoxic amyloid deposits. Increase in brain levels is reflected by higher levels in the CSF. The peptide was directly sequenced and the identify was confirmed using an anti-alpha-1-antichymotrypsin antibody.

M21100.1: This protein was identified as full-length Retinol-binding protein (SwissProt # P02753; theoretical. MW 21,071.60 Da). The identity of this marker was established by direct sequencing of 8 tryptic-digest fragments and a pull-down assay using an anti-Retinol-binding protein antibody.

M8575, M8292, M8184: These proteins were identified as ubiquitin and C-terminus fragments thereof. Neurofibrillary tangles (NFT) are composed of a hyperphosphorylated and ubiquitinated form of tau protein. With maturation, tau-based neurofibrillary tangles are increasingly ubiquitinated. Levels of tau and conjugated ubiquitin are elevated both in AD brain and CSF. CSF-ubiquitin levels are also associated with increasing degree of cortical and central brain atrophy as measured by computerized tomography.

M4971: This protein was identified as an N-acetylated form of Thymosin beta-4 (the N-terminal serine is acetylated). It is thought that Thymosin beta-4 may act as a marker for activated microglia, a central part of the chronic inflammatory processes in AD. The amino acid sequence of this protein is shown as SEQ ID: 10 (SwissProt Accession Number P62328).

M13960 and M14110: These biomarkers were identified as full-length Transthyretin S-Cys (and/or S-CysGly) and Transthyretin S-gluathionylated proteins, respectively. Transthyretin has been previously characterized as an A-beta sequestering protein which is present at lower concentrations in the CSF of AD patients versus healthy controls. This decrease is negatively correlated with senile plaque abundance.

M6502 and 7262: These biomarkers were identified as fragments of Chromogranin B (ChB) peptide found in neuronal large dense-core vesicles. ChB is highly processed by prohormone convertase (PC) enzymes to form smaller peptides from the precursor protein. A disease associated imbalance in PC enzymes could lead to changes in the processing of chromogranin proteins. Chromogranin proteins (ChA, ChB and SecretograninII) show distinct changes in their distribution in the brains of AD patients and are often associated with amyloid plaques. Chromogranin peptides including ChB have a potential as neuronal markers for synaptic degeneration in Alzheimer's disease.

M7658 and M7738: These biomarkers are Osteopontin C-terminal fragments, unphosphorylated and singly phosphorylated species respectively. Osteopontin is a cytokine regulating tissue repair that may play a key role in the pathogenesis of neuroinflammation.

M17380: This biomarker is a dimer of Apolipoprotein A-II. ApoA-II forms a complex with the protein ApoE which binds strongly to a-beta possibly playing a role in clearance. Levels of ApoA-II have previously been shown to be decreased in the serum of dementia patients.

M23477: This biomarker is prostaglandin D-synthase, a glycoprotein also known as beta-trace protein that catalyzes the formation of prostaglandin D2 (PGD2) from PGH2.

7653 Da/7718 Da (IMAC-Cu SPA): This protein was identified as a C-terminal fragment of Osteopontin (SwissProt# P10451, MW 7658.19 Da; SEQ ID NO: 11). Osteopontin is known to be extensively phosphorylated at serine residues. The 7653 Da is an unphosphorylated form, while the 7718 Da is a phosphorylated peptide. The sequence highlighted in bold in SEQ ID NO: 11 corresponds to the 7653 Da biomarker.

7258 Da (Q10 SPA): This protein is a processed fragment of Chromogranin B (Secretogranin I; SG1_HUMAN (SwissProt# P05060)). The sequence highlighted in bold in SEQ ID NO: 12 corresponds to the 7258 Da biomarker. Three underlined fragments were identified by MSMS with high scores. Y341 is sulfotyrosine, therefore the predicted MW is 7262.42 Da. The biochemistry to generate this peptide is exactly the same as for the 6502 Da peptide. The 7262 Da peptide sequence is flanked by cleavage sequences for prohormone convertase 1/3 and prohormone convertase 2: -KK-, -RR-, and -KR- (and carboxypeptidase H trims C-terminal Lys and Arg).

23 kDa biomarker: This protein is Prostaglandin-H2 D-isomerase (SwissProt# P41222). The predicted MW is 18.7 kDa, but the protein is very heavily glycosylated.

17.3 kDa biomarker: This protein is a Cys-Cys dimer of Apolipoprotein A-II (SwissProt# P02652). The MW of the plain monomer is 8707.91 Da, however the N-terminal Q is known to be modified to pyrrolidone carboxylic acid (−17 Da). Therefore the dimer of two full-length monomers is 17379.82 Da.

9.8 kDa (Q10 SPA): The protein was identified as the EA-92 peptide of Chromogranin A (SwissProt# P10645, MW 9730.18 Da; SEQ ID NO: 13). The sequence highlighted in bold in SEQ ID NO: 13 corresponds to the 9730 Da biomarker. Three fragments underlined were identified by MSMS with high scores. The 9730 Da peptide sequence is flanked by cleavage sequences for prohormone convertase ⅓ and prohormone convertase 2. Note that the 9.8 kDa biomarker (Q10) is not the same as the 9750 Da biomarker which appears under other (CM10, H50) assay conditions.

4812 Da (Q10): This biomarker was identified as processed fragment of VGF nerve growth factor inducible precursor (NCBI# gi17136078, MW 4808.80 Da; SEQ ID NO: 14). The sequence highlighted in bold in SEQ ID NO: 14 corresponds to the 4808 Da biomarker. Two fragments underlined were identified by MSMS and cover all the sequence of the peptide. The 4808 Da peptide sequence is flanked by cleavage sequences for prohormone convertase ⅓ and prohormone convertase 2.

4320 (IMAC-Ni): This biomarker was identified as A-beta 1-40 peptide (MW 4329.86 Da). This peak was found in Q fraction 3 using IMAC-Ni array, purified by RPC, YM30, and SDS-PAGE, digested with trypsin, and major ions in the digest were identified as fragments of Amyloid beta A4 precursor (SwissProt# P05067; SEQ ID NO: 15). The sequence in SEQ ID NO: 15 highlighted in bold corresponds to the 4330 Da biomarker. Three fragments underlined were identified by MSMS.

0194116.2 kDa (IMAC-Cu): This biomarker is glycosylated Pancreatic Ribonuclease (SwissProt# P07998). All peaks after the 16.2 kDa peak co-purify as an entity and appear to be various glycosylation forms. Ribonuclease is known to be only partially glycosylated. The 14.6 kDa peak, which co-purifieds with the 16.2 kDa biomarker, corresponds to the plain non-glycosylated form of Pancreatic Ribonuclease (MW 14,574.33 Da).

4146 Da (Q10): This polypeptide was identified as C-terminal fragment (SEQ ID NO: 16) of Protease C1 inhibitor (SwissProt # P05155, MW 4152.87 Da).

Figure 10:
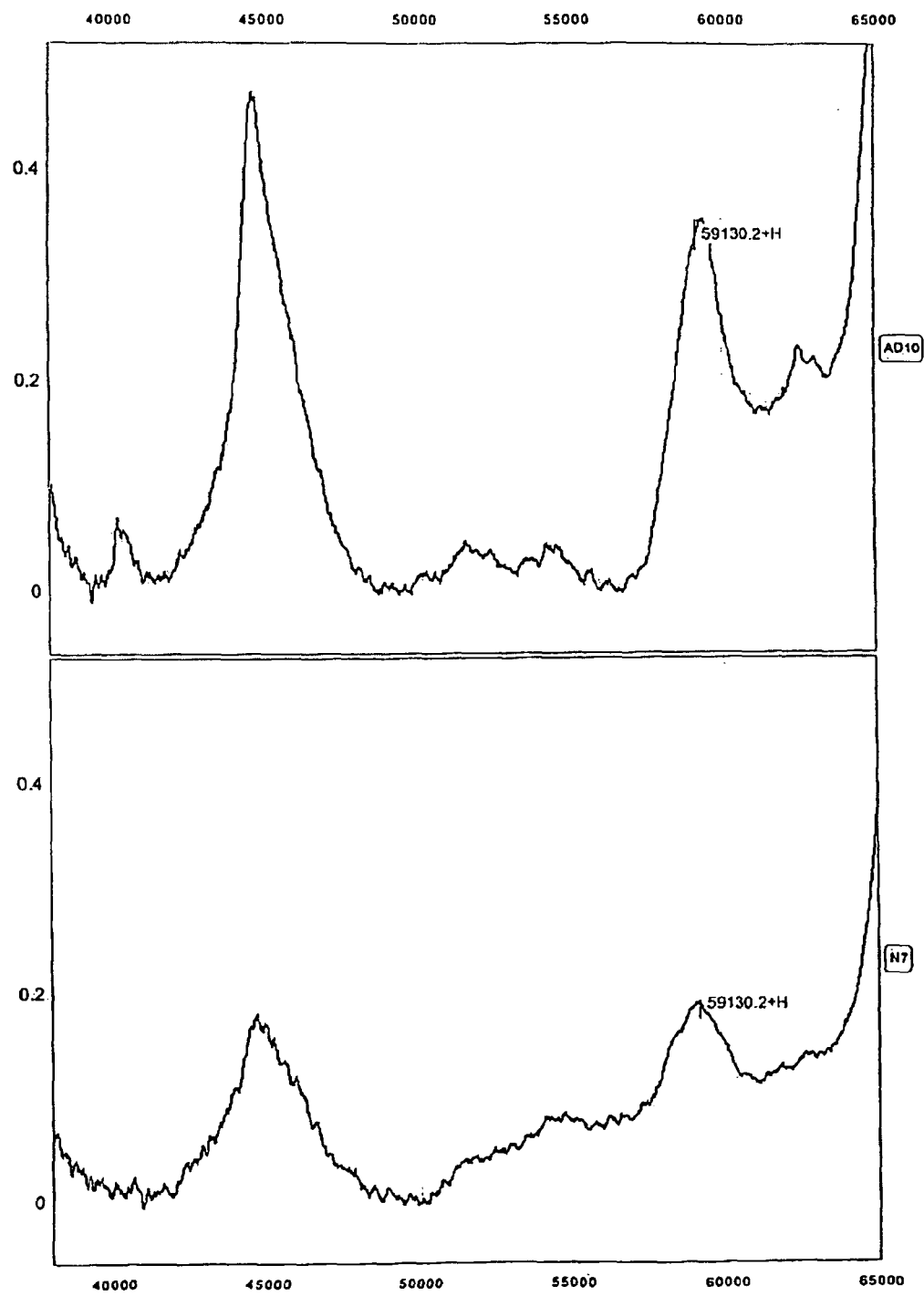
FIG. 10 summarizes the mechanistic relationships between a number of the biomarkers identified and described herein.
Figure 1P:
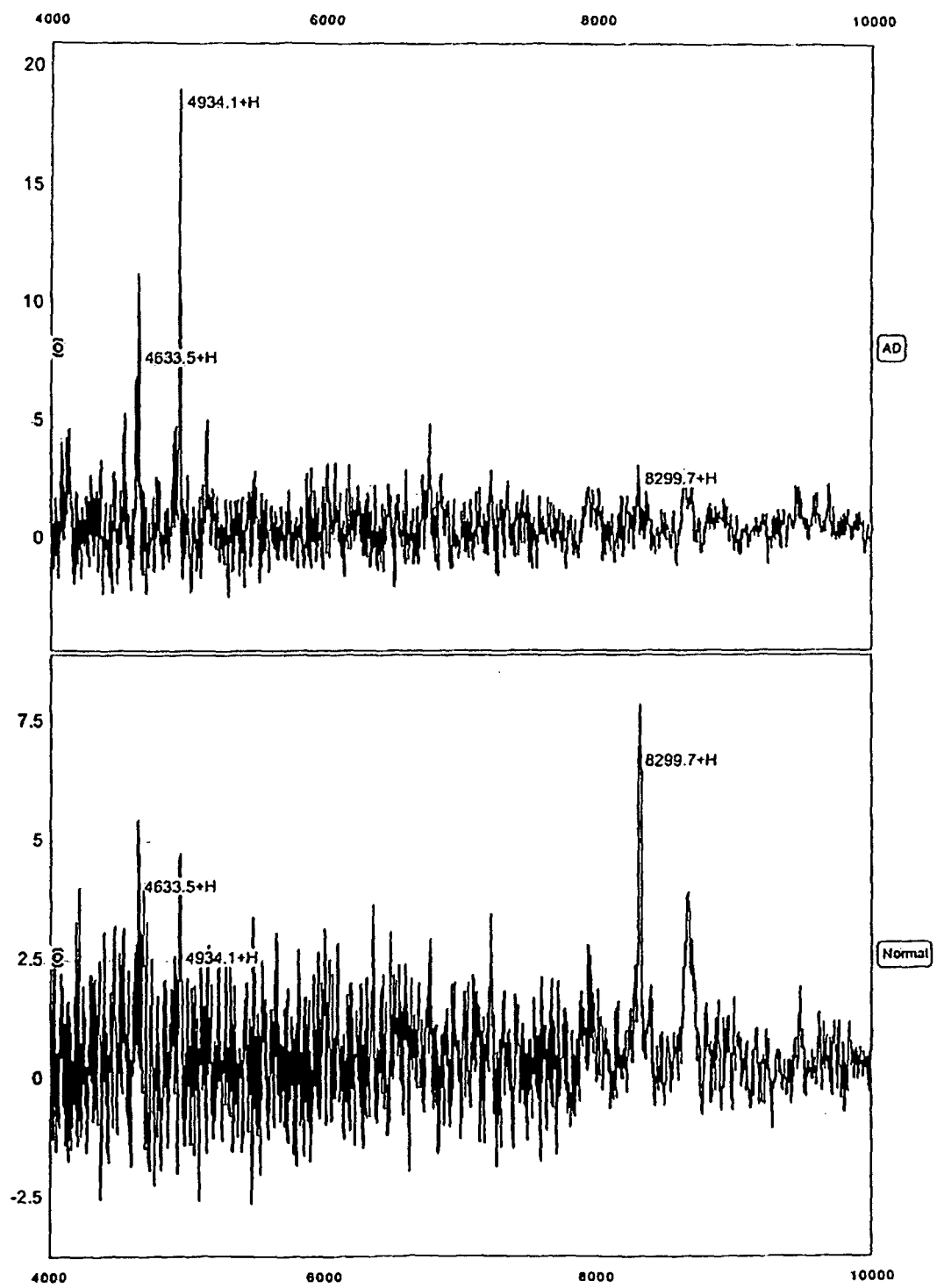
Figure 1Q:
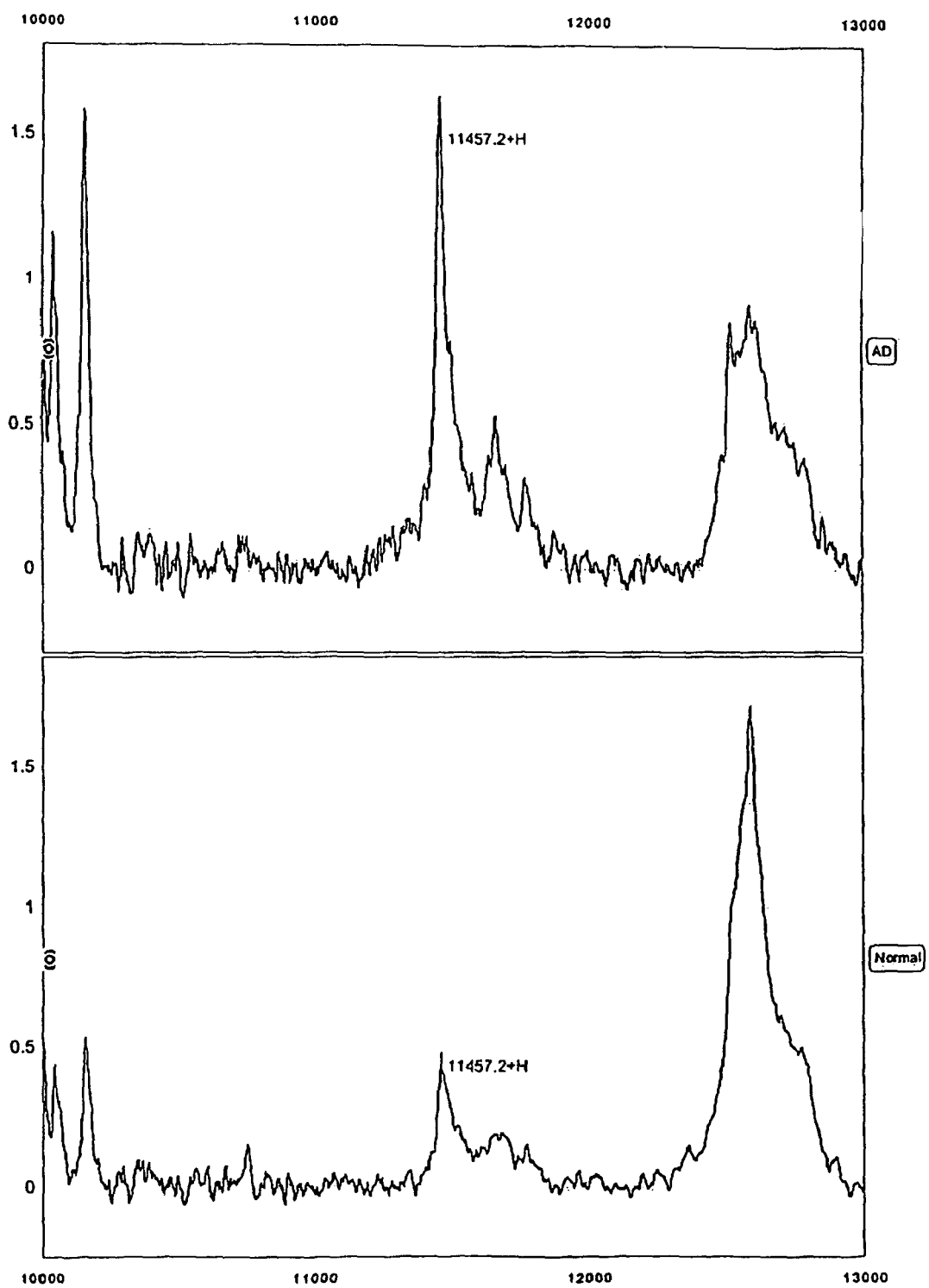

The foregoing biomarkers have a number of interesting mechanistic links to AD. For instance, the following are host response proteins and fragments: neurosectretory protein VGF (fragment); and Beta-2-microglobulin (full-length). The following are plaque "related" proteins/peptides: BRI membrane protein (fragment); A-Beta (fragments/forms); Cystatin C and truncated Cystatin-C (fragment); secreteoneurin; vasostatin II; ubiquitin and ubiquitin fragments; neuroendocrine protein 7B2; and Complement 3a protein (fragment). Finally, the following proteins play a role in iron transport and recycling: Transferrin (full-length); and Hemopexin (full-length). The mechanistic relationships between these biomarkers are summarized in FIG. 10 and in Table V, below.

TABLE V

List of characterized markers with Neuropathological associations

| | |
|---|---|
| Plaque Associated | Alpha1-antichymotrypsin (fragment) |
| | Retinol-binding protein |
| | Transthyretin (modified forms) |
| | Cystatin C (N-terminal truncation) |
| Neurofibrillary Tangle Associated | Ubiquitin full length (+2 fragments) |
| Synaptic Loss | Secretogranin II (fragment) |
| | Chromogranin A (fragment) |
| Neurotransmitter dysfunction | Neuroendocrine protein 7B2 fragment (fragment) |
| Lipid metabolism | Apolipoprotein C-I (truncated) |
| Inflammatory proteins | Alpha1-antichymotrypsin (fragment) |
| | Cystatin C (N-terminal truncation) |
| | Beta-2-microglobulin |
| | Thymosin beta-4 (modified) |
| | Complement 3a (fragment) |
| Iron metabolism and Oxidative Stress | Transferrin |
| | Hemopexin |
| Unknown | Neurosecretory protein VGF (3 fragments) |
| | BRI protein C-terminal fragment |

Example 4

Cystatin C and Modified Forms as Markers for Alzheimer's Disease

A. Sample Protocol

1. Manually apply 2 μL of a solution containing 0.25 mg/mL of Cystatin C antibody to each spot of an PS-20 array (Ciphergen Biosystems, Inc., Fremont, Calif.). For a negative control, use the same concentration of IgG on another spot.

2. Incubate for 2 h in a humidity chamber at room temperature to allow the antibodies to covalently bind to the spots.

3. Transfer the bioprocessor to Biomek 2000 liquid handling robot.

4. Block residual active sites by adding 25 μL 1 M ethanolamine. Incubate for 30 min at room temperature in a humidity chamber.

5. Remove unbound proteins by washing the array with 3 times 100 μL PBS+0.5% Triton X-100 5 min. each.

6. Wash with 100 μL PBS for 5 min.

7. Apply 20 μL neat CSF to each spot and incubate at 4° C. overnight.

8. Wash the spots with 3×100 μL PBS+0.5% Triton X-100 10 min each.

9. Wash with 3×100 μL PBS for 1 min each.

10. Rinse the array with 100 μL 1 mM HEPES.

11. Remove the bioprocessor from the Biomek 2000 robot.

12. Remove the bioprocessor gasket and allow the spots to air dry.

13. Manually apply 2×0.8 μL saturated SPA solution to each spot of the array.

14. Analyze the array using the ProteinChip Reader.

B. Validation of CysC Δ1-8 Marker

To validate the use of CysC Δ1-8 as a marker for Alzheimer's disease, 158 cerebrospinal fluid (CSF) samples were taken from pre-diagnosed subjects in three groups: (1) Alzheimer's disease (AD), Control, and Non-Alzheimer's dementia (Non AD). The distribution of samples in these groups is shown in Table III, above.

SELDI-MS measurements of CysC Δ1-8 in each of the samples were obtained according to standard protocols, using a Ciphergen H50 ProteinChip and 50% SPA as an EAM. The results are shown in the graph at the bottom left in FIG. 11.

Figure 11:
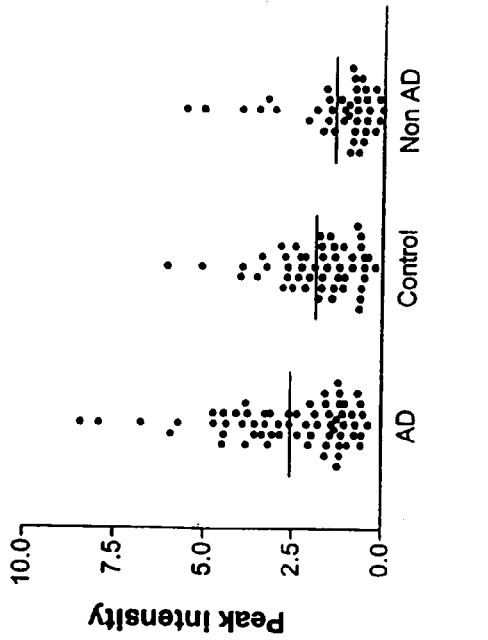
FIG. 11 shows the results of statistical tests used to validate the measurement of truncated CysC as a means for distinguishing between patients suffering from Alzheimer's dementia versus non-Alzheimer's dementia. In particular, the Figure shows a statistically significant difference in the average peak intensities of the truncated form of CysC (the 12583.8 Da marker) in Alzheimer's patients versus patients with non-Alzheimer's dementia ("A-N" p-value<0.0001).
Figure 11:
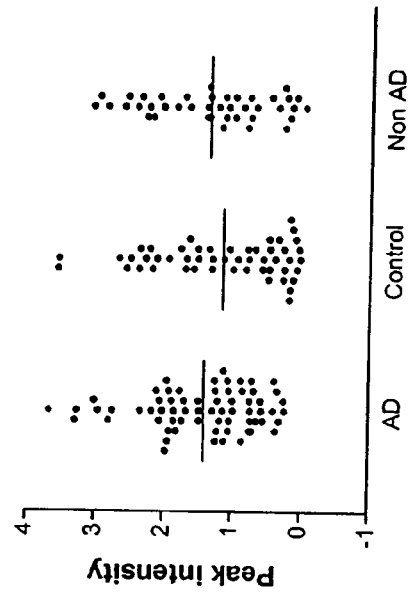

Similar measurements of full-length CysC were also made using the same set of samples (FIG. 11, bottom right). The results show that the levels of CysC Δ1-8 in subjects suffering from Alzheimer's disease are significantly higher than the levels in subjects suffering from non-Alzheimer's dementia.

Example 5

Marker Combination for Detecting Alzheimers

As discussed above, a combination of biomarkers can provide greater predictive value of a particular status than single biomarkers alone. A plurality of biomarkers in a sample can increase the sensitivity and/or specificity of the test. A preferred set of biomarkers for qualifying Alzheimer's status in a patient is one in which the biomarkers of the set are regulated in vivo independently of each other. A preferred test has greater than 80% sensitivity and specificity. Even more preferred are tests where both the sensitivity and specificity are greater than 90%. One example of a set of biomarkers which is preferred for a combination test includes M17349.3 (Apolipoprotein A-II dimer), M60464.7 (Hemopexin), and M3513.9 (7B2 CT fragment). Another example of a preferred set of biomarkers is the set which includes M17349.3 (Apolipoprotein A-II dimer), M60464.7 (Hemopexin), M10379.8 (10.3 kDa) and M11725.7 (Beta-2-Microglobulin).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for qualifying Alzheimer's disease status in a subject comprising:
    (a). measuring at least one biomarker in a CSF sample from the subject, wherein said at least one biomarker consists of residues 35-121 of SEQ ID NO:4;
    (b). comparing the level of the biomarker in said subject to a diagnostic cut-off level; and
    (c). correlating the measurement with Alzheimer's disease status, wherein elevated levels of the biomarker in said CSF sample relative to said diagnostic cut-off level are indicative of an increased likelihood of Alzheimer's disease in said subject.

2. The method of claim 1, wherein said at least one biomarker is a single biomarker, and.

3. The method of claim 1, further comprising measuring Pancreatic ribonuclease.

4. The method of claim 1, further comprising measuring Apolipoprotein C-I.

5. The method of claim 1, further comprising measuring Cystatin C.

6. The method of claim 1, further comprising measuring at least each of the following biomarkers: Pancreatic ribonuclease, C3a des-Arg, Apolipoprotein C-I and Cystatin C.

7. The method of claim 1, wherein the at least one biomarker is measured by a means of detection other than by mass.

8. The method of claim 7, wherein the at least one biomarker is measured by immunoassay.

9. The method of claim 1 or 2, wherein the at least one biomarker is measured by immunoassay.

10. The method of claim 1 or 2, wherein the at least one biomarker is measured by capturing the biomarker on an adsorbent surface of a SELDI probe and detecting the captured biomarkers by laser desorption-ionization mass spectrometry.

11. The method of claim 10, wherein the adsorbent is a cation exchange adsorbent.

12. The method of claim 10, wherein the adsorbent is a biospecific adsorbent.

13. The method of claim 10, wherein the adsorbent is a hydrophobic adsorbent.

14. The method of claim 1 or 2, wherein the correlating is performed by a software classification algorithm.

15. The method of claim 1 or 2, further comprising (d) managing subject treatment based on the status.

16. The method of claim 15, further comprising:
    (e) measuring the at least one biomarker after subject management.

17. The method of claim 1 or 2, wherein Alzheimer's disease status is selected from Alzheimer's disease and non-dementia, wherein decreased levels of the biomarker in said CSF sample relative to said diagnostic cut-off level are indicative of non-dementia.

18. The method of claim 17, wherein, if the measurement correlates with Alzheimer's disease, then managing subject treatment comprises administering a choline esterase inhibitor to the subject.

19. The method of claim 1 or 2, wherein Alzheimer's disease status is selected from Alzheimer's disease, non-dementia, and non-Alzheimer's dementia, wherein decreased levels of the biomarker in said CSF sample relative to said diagnostic cut-off level are indicative of non-dementia or non-Alzheimer's dementia.

20. The method of claim 1 or 2, wherein Alzheimer's disease status is selected from Alzheimer's disease and non-Alzheimer's dementia, wherein decreased levels of the biomarker in said CSF sample relative to said diagnostic cut-off level are indicative non-Alzheimer's dementia.

21. The method of claim 20 wherein non-Alzheimer's dementia is selected from dementia with Lewy bodies and frontotemporal dementia.

* * * * *